(12) United States Patent
Zhang et al.

(10) Patent No.: US 11,760,806 B2
(45) Date of Patent: Sep. 19, 2023

(54) CD-38 DIRECTED CHIMERIC ANTIGEN RECEPTOR CONSTRUCTS

(71) Applicant: Sorrento Therapeutics, Inc., San Diego, CA (US)

(72) Inventors: Yanliang Zhang, San Diego, CA (US); Heyue Zhou, San Diego, CA (US); Qianzhong Ma, San Diego, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 211 days.

(21) Appl. No.: 16/179,850

(22) Filed: Nov. 2, 2018

(65) Prior Publication Data
US 2019/0135937 A1  May 9, 2019

Related U.S. Application Data

(60) Provisional application No. 62/581,466, filed on Nov. 3, 2017.

(51) Int. Cl.
| | |
|---|---|
| *C07K 16/28* | (2006.01) |
| *A61K 39/00* | (2006.01) |
| *C07K 14/725* | (2006.01) |
| *C07K 14/705* | (2006.01) |

(52) U.S. Cl.
CPC ...... *C07K 16/2896* (2013.01); *A61K 39/0011* (2013.01); *C07K 14/7051* (2013.01); *C07K 14/70517* (2013.01); *C07K 14/70521* (2013.01); *A61K 2039/505* (2013.01); *A61K 2039/5156* (2013.01); *A61K 2039/5158* (2013.01); *C07K 2317/73* (2013.01); *C07K 2319/00* (2013.01); *C07K 2319/03* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 7,446,190 B2 | 11/2008 | Sadelain et al. | |
| 7,829,673 B2 | 11/2010 | Weers et al. | |
| 8,486,394 B2 | 7/2013 | Tesar et al. | |
| 8,926,969 B2 | 1/2015 | Elias et al. | |
| 10,059,774 B2 | 8/2018 | Zhou et al. | |
| 2015/0118251 A1 | 4/2015 | Deslandes et al. | |
| 2016/0237161 A1 | 8/2016 | Weers et al. | |
| 2016/0297888 A1* | 10/2016 | Zhou | A61K 39/39558 |
| 2016/0340649 A1* | 11/2016 | Brown | C07K 14/7051 |
| 2020/0399393 A1* | 12/2020 | Ji | A61K 35/17 |
| 2021/0228696 A1* | 7/2021 | Boitano | A61K 47/65 |
| 2021/0260212 A1* | 8/2021 | Boitano | A61K 47/6849 |

FOREIGN PATENT DOCUMENTS

| | | |
|---|---|---|
| CN | 105802975 A | 7/2016 |
| JP | 2017506636 A | 3/2017 |
| WO | WO-9402610 A1 * | 2/1994 ............ A61P 31/18 |
| WO | 2015/121454 A1 | 8/2015 |
| WO | 2015121454 A1 | 8/2015 |
| WO | WO-2016109668 A1 * | 7/2016 ........... A61K 31/713 |
| WO | 2016168493 A1 | 10/2016 |
| WO | 2016164669 A3 | 1/2017 |
| WO | 2017025323 A1 | 2/2017 |
| WO | 2017070654 A1 | 4/2017 |
| WO | WO-2017068361 A1 * | 4/2017 ............ A61K 35/17 |
| WO | 2018/154386 A1 | 8/2018 |

OTHER PUBLICATIONS

Almagro & Fransson, Frontiers in Bioscience 2008; 13:1619-33 (Year: 2008).*
Mihara et al. Br. J. Haematol 151(1): 37-46 2009 (Year: 2009).*
NCT03464916 (ClinicalTrials.gov archive Mar. 7, 2018) (Year: 2018).*
Sorrento Therapeutics (Globe Newswire Nov. 1, 2018) (Year: 2018).*
Prazma and Tedder (Immunology Letters 2008, 115: 1-8) (Year: 2008).*
CD3Z_Human P20963 (Uniprot, T-cell surface glycoprotein CD3 zeta chain precursor, Jun. 15, 2002) (Year: 2002).*
International Search Report and Written Opinion relating to International Application No. PCT/IB18/058642 completed Dec. 4, 2018 and dated Dec. 19, 2018.
Drent, E., et al., "CD38 Chimeric Antigen Receptor Engineered T Cells as Therapeutic Tools for Multiple Myeloma," Blood, American Society of Hematology, 124:21, p. 4759 (2014), Abstract.
Sorrento Therapeutics, Inc., "Sorrento's TNK Therapeutics Provides Progress Update for its Anti-CD38 and CD123 CAR-T Programs for Treatment of Hematological Malignancies," PRNewsire, Dec. 2016.
Atanackovic, D., et al. "Immunotherapies Targeting CD38 in Multiple Myeloma," Oncoimmunology 2016, vol. 5, No. 11, e1217374 (11 pages).
Drent, E. et al., "Pre-clinical evaluation of CD38 chimeric antigen receptor engineered T cells for the treatment of multiple myeloma," 2016 Haematologica 101(5):616-625 Article.
Drent, E. et al., "Pre-clinical evaluation of CD38 chimeric antigen receptor engineered T cells for the treatment of multiple myeloma," 2016 Haematologica 101(5):616-625, Supplemental Data.
Emtage, P. et al., "Second-Generation Anti-Carcinoembryonic Antigen Designer T Cells Resist Activation-Induced Cell Death, Proliferate on Tumor Contact, Secrete Cytokines, and Exhibit Superior Antitumor Activity In vivo: A Preclinical Evaluation." 2008 Clinical Cancer Research 14(24):8112-8122.

(Continued)

*Primary Examiner* — Peter J Reddig
(74) *Attorney, Agent, or Firm* — McNeill Baur PLLC

(57) ABSTRACT

There is disclosed compositions and methods relating to or derived from anti-CD38 antibodies. More specifically, there is disclosed fully human antibodies that bind CD38, CD38-antibody binding fragments and derivatives of such antibodies, and CD38-binding polypeptides comprising such fragments. Further still, there is disclosed nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating a disease.

18 Claims, 8 Drawing Sheets

Specification includes a Sequence Listing.

(56) References Cited

OTHER PUBLICATIONS

Eshar Z., et al., "Specific activation and targeting of cytotoxic lymphocytes through chimeric single chains consisting of antibody-binding domains and the gamma or zeta subunits of the immunoglobulin and T-cell receptors," 1993 Proc. Nat'l. Acad. of Sci. USA 90(2):720-724.
Finney H. et al., "Chimeic receptors providing both primary and costimulatory signaling in T cells from a single gene product." 1998 Journal of Immunology 161(6):2791-2797.
Gross, G. et al., "Expression of immunoglobulin T-cell receptor chimeric molecules as functional receptors with antibody-type specificity," Proc. Natl. Acad. of Sci. USA 86(24):10024-10028, 1989.
Haynes, NM et al., "Redirecting mouse CTL against colon carcinoma: superior signaling efficacy of single-chain variable domain chimeras containing TCR-zeta vs FcRl-gamma," 2001 The Journal of Immunology 166(1):182-187.
Hombach A., et al., "Tumor-specific T cell activation by recombinant immunoreceptors: CD3? signaling and CD28 costimulation are simultaneously required for efficient IL-2 secretion and can be integrated into one combined CD28/CD3? signaling receptor molecule." 2001 Journal of Immunology 167(11):6123-6131.
Lo, A. et al., "Anti-GD3 Chimeric sFv-CD28/T-Cell Receptor Zeta Designer T Cells for Treatment of Metastatic Melanoma and Other Neuroectodermal Tumors," 2010 Clinical Cancer Research 16(10):2769-2780.
Ma, Q. et al., "Advanced Generation Anti-Prostate Specific Membrane Antigen Designer T Cells for Prostate Cancer Immunotherapy," 2014 The Prostate 74:286-296.
Ma, Q. et al., "Anti-Prostate Specific Membrane Antigen Designer T Cells for Prostate Cancer Therapy," 2004 The Prostate 61:12-25.
Maher, J. et al., "Human T-lymphocyte cytotoxicity and proliferation directed by a single chimeric TCRzeta/CD28 receptor." 2002 Nature Biotechnology 20(1):70-75.
Mihara, K. et al., "Activated T-cell mediated immunotherapy with a chimeric receptor against CD38 in B-cell non-Hodgkin lymphoma," 2009 Journal of Immunology 32:737-743.
Ma et al., "Genetically engineered T cells as adoptive immunotherapy of cancer," Cancer Chemother. Biol Response Modif. 20: 319-345, 2002.
Bhattacharyya et al., "T-cell immunotherapy with a chimeric receptor against CD38 is effective in eradicating chemotherapy-resistant B-cell lymphoma cells overexpressing survivin induced by BMI-1," Blood Cancer J. 2(6): e75, 2012.
Deaglio et al., "Human CD38 (ADP-ribosyl cyclase) is a counter-receptor of CD31, an Ig superfamily member," J. Immunol. 160(1):395-402, 1998.
Ferlay et al., "Cancer incidence and mortality worldwide: sources, methods and major patterns in GLOBOCAN 2012," Int. J. Cancer 136(5): E359-386. 2015.
Genty et al., "Phenotypical alterations induced by glucocorticoids resistance in RPMI 8226 human myeloma cells," Leuk Res 28(3): 307-313 2004.
Gregorini et al., "CD38 expression enhances sensitivity of lymphoma T and B cell lines to biochemical and receptor-mediated apoptosis," 2006 Cell Biology International 30(9):727-732.
Kharfan-Dabaja et al., "Comparative efficacy of tandem autologous versus autologous followed by allogeneic hematopoietic cell transplantation in patients with newly diagnosed multiple myeloma: a systematic review and meta-analysis of randomized controlled trials," J. Hematol. Oncol. 6:2, 2013.
Kumar et al., "Improved survival in multiple myeloma and the impact of novel therapies," Blood 111(5): 2516-2520, 2008.
Leisegang, M. et al., "MHC-restricted fratricide of human lymphocytes expressing survivin-specific transgenic T cell receptors," Nov. 2010;120(11):3869-77.
Mihara et al., "T-cell immunotherapy with a chimeric receptor against CD38 is effective in eliminating myeloma cells," Leukemia (2012) 26, 365-367.
Sandoval-Montes et al., "CD38 is expressed selectively during the activation of a subset of mature T cells with reduced proliferation but improved potential to produce cytokines," J. Leukocyte Biol. 77(4): 513-521, 2005.
Schendel et al., "Limitations for TCR gene therapy by MHC-restricted fratricide and TCR-mediated hematopoietic stem cell toxicity," Oncoimmunology Jan. 1, 2013; 2(1): e22410.
Taniguchi et al., "2B4 inhibits NK-cell fratricide," (2007) Blood 110, 2020-2023.
Drent et al., "A Rational Strategy for Reducing On-Target Off-Tumor Effects of CD38-Chimeric Antigen Receptors by Affinity Optimization," Molecular Therapy 25(8): 1946-1958 (2017).
Konen et al., "The Good, the Bad and the Unknown of CD38 in the Metabolic Microenvironment and Immune Cell Functionality of Solid Tumors," Cells 9(1):52, pp. 1-20 (2020).
Communication pursuant to Rule 114(2) EPC in European Patent Application No. 18801058.1, dated Jul. 29, 2022 (4 pages).

\* cited by examiner

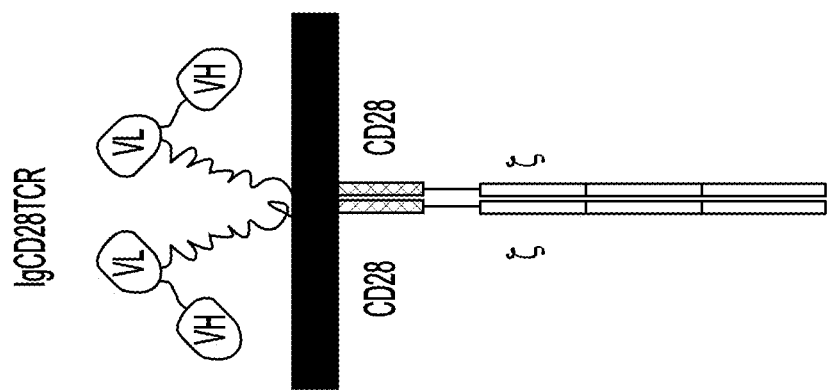
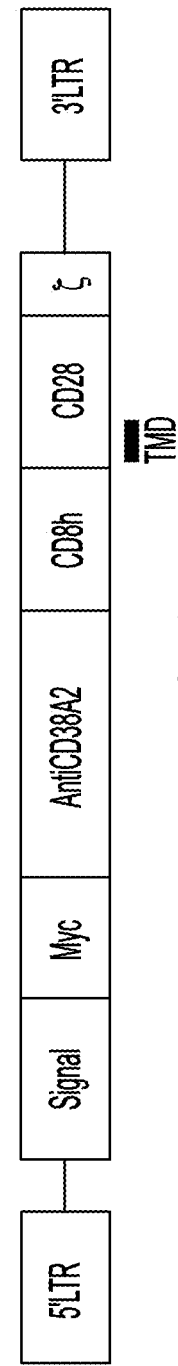
FIG. 1A
FIG. 1B

SEQUENCE LISTING

<160> NUMBER OF SEQ ID NOS: 22

<210> SEQ ID NO 1
<211> LENGTH: 118
<212> TYPE: PRT
<213> ORGANISM: Homo sapiens

<400> SEQUENCE: 1

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asp
            20                  25                  30

Tyr Met Ser Trp Ile Arg Gln Ala Pro Gly Lys Gly Leu Glu Trp Val
        35                  40                  45

Ala Ser Val Ser Asn Gly Arg Pro Thr Thr Tyr Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Trp Gly Gly Glu Phe Thr Asp Trp Gly Arg Gly Thr
            100                 105                 110

Leu Val Thr Val Ser Ser
        115

<210> SEQ ID NO 2
<211> LENGTH: 124
<212> TYPE: PRT
<213> ORGANISM: Homo sapiens

<400> SEQUENCE: 2

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Ile Val Ser Thr Asn
            20                  25                  30

Tyr Val His Trp Val Arg Gln Ala Pro Gly Lys Gly Leu Glu Trp Val
        35                  40                  45

Ser Gly Ile Tyr Ser Asp Pro Tyr Thr Ser Tyr Ala Tyr Ser Asp Ser
    50                  55                  60

Val Lys Gly Arg Phe Thr Ile Ser Arg Asp Met Ser Lys Asn Thr Val
65                  70                  75                  80

Tyr Leu Gln Met Asn Arg Leu Arg Ala Glu Asp Thr Ala Val Tyr Tyr
                85                  90                  95

Cys Ala Arg Glu Thr Asn Thr Gly Phe Ser Asn Ser Trp Tyr Leu Asp
            100                 105                 110

Phe Trp Gly Gln Gly Thr Leu Val Thr Val Ser Ser
        115                 120

<210> SEQ ID NO 3
<211> LENGTH: 110
<212> TYPE: PRT
<213> ORGANISM: Homo sapiens

<400> SEQUENCE: 3

Gln Ala Gly Leu Thr Gln Pro Pro Ser Ala Ser Gly Thr Ser Gly Gln
1               5                   10                  15

Arg Val Thr Ile Ser Cys Ser Gly Ser Ser Ser Asn Ile Gly Ile Asn
            20                  25                  30

```
Phe Val Tyr Trp Tyr Gln His Leu Pro Gly Thr Ala Pro Lys Leu Leu
        35                  40                  45

Ile Tyr Lys Asn Asn Gln Arg Pro Ser Gly Val Pro Asp Arg Phe Ser
    50                  55                  60

Gly Ser Lys Ser Gly Asn Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Ser Gly Thr Lys Val Thr Val Leu
                100                 105                 110

<210> SEQ ID NO 4
<211> LENGTH: 110
<212> TYPE: PRT
<213> ORGANISM: Homo sapiens

<400> SEQUENCE: 4

Gln Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Arg Asn
            20                  25                  30

Ile Val Asn Trp Tyr Gln Gln Leu Pro Gly Thr Thr Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu His
65                  70                  75                  80

Ser Glu Asp Glu Ala Asp Tyr Tyr Cys Ala Thr Trp Asp Asp Ser Leu
                85                  90                  95

Asn Gly Trp Val Phe Gly Gly Gly Thr Lys Leu Thr Val Leu
                100                 105                 110

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Gly Ser Gly Gly Gly Ser Gly Gly Gly Ser
1               5                   10                  15

<210> SEQ ID NO 6
<211> LENGTH: 46
<212> TYPE: PRT
<213> ORGANISM: Homo sapiens

<400> SEQUENCE: 6

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala
        35                  40                  45

<210> SEQ ID NO 7
<211> LENGTH: 40
```

```
<212> TYPE: PRT
<213> ORGANISM: Homo sapiens

<400> SEQUENCE: 7

Lys Ile Glu Val Met Tyr Pro Pro Tyr Leu Asp Asn Glu Lys Ser
1               5                   10                  15

Asn Gly Thr Ile Ile His Val Lys Gly Lys His Leu Cys Pro Ser Pro
            20                  25                  30

Leu Phe Pro Gly Pro Ser Lys Pro
            35                  40

<210> SEQ ID NO 8
<211> LENGTH: 27
<212> TYPE: PRT
<213> ORGANISM: Homo sapiens

<400> SEQUENCE: 8

Phe Trp Val Leu Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 9
<211> LENGTH: 41
<212> TYPE: PRT
<213> ORGANISM: Homo sapiens

<400> SEQUENCE: 9

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 10
<211> LENGTH: 113
<212> TYPE: PRT
<213> ORGANISM: Homo sapiens

<400> SEQUENCE: 10

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 11
<211> LENGTH: 10
```

<212> TYPE: PRT
<213> ORGANISM: Homo sapiens

<400> SEQUENCE: 11

Glu Gln Lys Leu Ile Ser Glu Glu Asp Leu
1               5                   10

<210> SEQ ID NO 12
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asp
            20                  25                  30

Tyr Met Ser Trp Ile Arg Gln Ala Pro Gly Lys Gly Leu Glu Trp Val
        35                  40                  45

Ala Ser Val Ser Asn Gly Arg Pro Thr Thr Tyr Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Trp Gly Glu Phe Thr Asp Trp Gly Arg Gly Thr
            100                 105                 110

Leu Val Thr Val Ser Ser Gly Gly Gly Ser Gly Gly Gly Gly Ser
        115                 120                 125

Gly Gly Gly Gly Ser Gln Ala Gly Leu Thr Gln Pro Pro Ser Ala Ser
    130                 135                 140

Gly Thr Ser Gly Gln Arg Val Thr Ile Ser Cys Ser Gly Ser Ser Ser
145                 150                 155                 160

Asn Ile Gly Ile Asn Phe Val Tyr Trp Tyr Gln His Leu Pro Gly Thr
                165                 170                 175

Ala Pro Lys Leu Leu Ile Tyr Lys Asn Asn Gln Arg Pro Ser Gly Val
            180                 185                 190

Pro Asp Arg Phe Ser Gly Ser Lys Ser Gly Asn Ser Ala Ser Leu Ala
        195                 200                 205

Ile Ser Gly Leu Arg Ser Glu Asp Glu Ala Asp Tyr Tyr Cys Ala Ala
    210                 215                 220

Trp Asp Asp Ser Leu Ser Gly Tyr Val Phe Gly Ser Gly Thr Lys Val
225                 230                 235                 240

Thr Val Leu

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
acacagtcct gctgacca                                                 18

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gggagtcatg ttcatgtag                                                   19

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tggtgatatt gttgagt                                                     17

<210> SEQ ID NO 16
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Ile Val Ser Thr Asn
            20                  25                  30

Tyr Val His Trp Val Arg Gln Ala Pro Gly Lys Gly Leu Glu Trp Val
        35                  40                  45

Ser Gly Ile Tyr Ser Asp Pro Tyr Thr Ser Tyr Ala Tyr Ser Asp Ser
    50                  55                  60

Val Lys Gly Arg Phe Thr Ile Ser Arg Asp Met Ser Lys Asn Thr Val
65                  70                  75                  80

Tyr Leu Gln Met Asn Arg Leu Arg Ala Glu Asp Thr Ala Val Tyr Tyr
                85                  90                  95

Cys Ala Arg Glu Thr Asn Thr Gly Phe Ser Asn Ser Trp Tyr Leu Asp
            100                 105                 110

Phe Trp Gly Gln Gly Thr Leu Val Thr Val Ser Ser Gly Gly Gly Gly
        115                 120                 125

Ser Gly Gly Gly Gly Ser Gly Gly Gly Gly Ser Gln Pro Val Leu Thr
    130                 135                 140

Gln Pro Pro Ser Ala Ser Gly Thr Pro Gly Gln Arg Val Thr Ile Ser
145                 150                 155                 160

Cys Ser Gly Ser Ser Ser Asn Ile Gly Arg Asn Ile Val Asn Trp Tyr
                165                 170                 175

Gln Gln Leu Pro Gly Thr Thr Pro Lys Leu Leu Ile Tyr Ser Asn Asn
            180                 185                 190

Gln Arg Pro Ser Gly Val Pro Asp Arg Phe Ser Gly Ser Lys Ser Gly
        195                 200                 205

Thr Ser Ala Ser Leu Ala Ile Ser Gly Leu His Ser Glu Asp Glu Ala
    210                 215                 220

-continued

Asp Tyr Tyr Cys Ala Thr Trp Asp Asp Ser Leu Asn Gly Trp Val Phe
225                 230                 235                 240

Gly Gly Gly Thr Lys Leu Thr Val Leu
                245

<210> SEQ ID NO 17
<211> LENGTH: 88
<212> TYPE: PRT
<213> ORGANISM: Homo sapiens

<400> SEQUENCE: 17

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Pro Arg
        35                  40                  45

Lys Ile Glu Val Met Tyr Pro Pro Pro Tyr Leu Asp Asn Glu Lys Ser
    50                  55                  60

Asn Gly Thr Ile Ile His Val Lys Gly Lys His Leu Cys Pro Ser Pro
65                  70                  75                  80

Leu Phe Pro Gly Pro Ser Lys Pro
                85

<210> SEQ ID NO 18
<211> LENGTH: 108
<212> TYPE: PRT
<213> ORGANISM: Homo sapiens

<400> SEQUENCE: 18

Lys Ile Glu Val Met Tyr Pro Pro Pro Tyr Leu Asp Asn Glu Lys Ser
1               5                   10                  15

Asn Gly Thr Ile Ile His Val Lys Gly Lys His Leu Cys Pro Ser Pro
            20                  25                  30

Leu Phe Pro Gly Pro Ser Lys Pro Phe Trp Val Leu Val Val Val Gly
        35                  40                  45

Gly Val Leu Ala Cys Tyr Ser Leu Leu Val Thr Val Ala Phe Ile Ile
    50                  55                  60

Phe Trp Val Arg Ser Lys Arg Ser Arg Leu Leu His Ser Asp Tyr Met
65                  70                  75                  80

Asn Met Thr Pro Arg Arg Pro Gly Pro Thr Arg Lys His Tyr Gln Pro
                85                  90                  95

Tyr Ala Pro Pro Arg Asp Phe Ala Ala Tyr Arg Ser
            100                 105

<210> SEQ ID NO 19
<211> LENGTH: 19
<212> TYPE: PRT
<213> ORGANISM: Mus sp.

<400> SEQUENCE: 19

Met Glu Trp Ser Trp Val Phe Leu Phe Phe Leu Ser Val Thr Thr Gly
1               5                   10                  15

Val His Ser

<210> SEQ ID NO 20
<211> LENGTH: 541
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Glu Trp Ser Trp Val Phe Leu Phe Phe Leu Ser Val Thr Thr Gly
1               5                   10                  15

Val His Ser Asp Ile Glu Gln Lys Leu Ile Ser Glu Glu Asp Leu Gln
            20                  25                  30

Val Gln Leu Val Glu Ser Gly Gly Leu Val Lys Pro Gly Gly Ser
        35                  40                  45

Leu Arg Leu Ser Cys Ala Ala Ser Gly Phe Thr Phe Ser Asp Asp Tyr
    50                  55                  60

Met Ser Trp Ile Arg Gln Ala Pro Gly Lys Gly Leu Glu Trp Val Ala
65                  70                  75                  80

Ser Val Ser Asn Gly Arg Pro Thr Thr Tyr Tyr Ala Asp Ser Val Arg
                85                  90                  95

Gly Arg Phe Thr Ile Ser Arg Asp Asn Ala Lys Asn Ser Leu Tyr Leu
            100                 105                 110

Gln Met Asn Ser Leu Arg Ala Glu Asp Thr Ala Val Tyr Tyr Cys Ala
        115                 120                 125

Arg Glu Asp Trp Gly Gly Glu Phe Thr Asp Trp Gly Arg Gly Thr Leu
    130                 135                 140

Val Thr Val Ser Ser Gly Gly Gly Ser Gly Gly Gly Gly Ser Gly
145                 150                 155                 160

Gly Gly Gly Ser Gln Ala Gly Leu Thr Gln Pro Pro Ser Ala Ser Gly
                165                 170                 175

Thr Ser Gly Gln Arg Val Thr Ile Ser Cys Ser Gly Ser Ser Ser Asn
            180                 185                 190

Ile Gly Ile Asn Phe Val Tyr Trp Tyr Gln His Leu Pro Gly Thr Ala
        195                 200                 205

Pro Lys Leu Leu Ile Tyr Lys Asn Asn Gln Arg Pro Ser Gly Val Pro
    210                 215                 220

Asp Arg Phe Ser Gly Ser Lys Ser Gly Asn Ser Ala Ser Leu Ala Ile
225                 230                 235                 240

Ser Gly Leu Arg Ser Glu Asp Glu Ala Asp Tyr Tyr Cys Ala Ala Trp
                245                 250                 255

Asp Asp Ser Leu Ser Gly Tyr Val Phe Gly Ser Gly Thr Lys Val Thr
            260                 265                 270

Val Leu Ala Lys Pro Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys
    290                 295                 300

Arg Pro Ala Ala Gly Gly Ala Val His Thr Arg Gly Leu Asp Phe Ala
305                 310                 315                 320

Lys Ile Glu Val Met Tyr Pro Pro Pro Tyr Leu Asp Asn Glu Lys Ser
                325                 330                 335

Asn Gly Thr Ile Ile His Val Lys Gly Lys His Leu Cys Pro Ser Pro
            340                 345                 350

Leu Phe Pro Gly Pro Ser Lys Pro Phe Trp Val Leu Val Val Val Gly
        355                 360                 365

Gly Val Leu Ala Cys Tyr Ser Leu Leu Val Thr Val Ala Phe Ile Ile
    370                 375                 380

Phe Trp Val Arg Ser Lys Arg Ser Arg Leu Leu His Ser Asp Tyr Met

```
                385                 390                 395                 400
Asn Met Thr Pro Arg Arg Pro Gly Pro Thr Arg Lys His Tyr Gln Pro
                    405                 410                 415

Tyr Ala Pro Pro Arg Asp Phe Ala Ala Tyr Arg Ser Arg Val Lys Phe
                420                 425                 430

Ser Arg Ser Ala Asp Ala Pro Ala Tyr Gln Gln Gly Gln Asn Gln Leu
            435                 440                 445

Tyr Asn Glu Leu Asn Leu Gly Arg Arg Glu Tyr Asp Val Leu Asp
        450                 455                 460

Lys Arg Arg Gly Arg Asp Pro Glu Met Gly Gly Lys Pro Gln Arg Arg
465                 470                 475                 480

Lys Asn Pro Gln Glu Gly Leu Tyr Asn Glu Leu Gln Lys Asp Lys Met
                    485                 490                 495

Ala Glu Ala Tyr Ser Glu Ile Gly Met Lys Gly Glu Arg Arg Arg Gly
                500                 505                 510

Lys Gly His Asp Gly Leu Tyr Gln Gly Leu Ser Thr Ala Thr Lys Asp
            515                 520                 525

Thr Tyr Asp Ala Leu His Met Gln Ala Leu Pro Pro Arg
        530                 535                 540

<210> SEQ ID NO 21
<211> LENGTH: 547
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Glu Trp Ser Trp Val Phe Leu Phe Phe Leu Ser Val Thr Thr Gly
1               5                   10                  15

Val His Ser Asp Ile Glu Gln Lys Leu Ile Ser Glu Glu Asp Leu Gln
                20                  25                  30

Val Gln Leu Val Glu Ser Gly Gly Gly Val Val Gln Pro Gly Gly Ser
            35                  40                  45

Leu Arg Leu Ser Cys Ala Ala Ser Gly Phe Ile Val Ser Thr Asn Tyr
        50                  55                  60

Val His Trp Val Arg Gln Ala Pro Gly Lys Gly Leu Glu Trp Val Ser
65                  70                  75                  80

Gly Ile Tyr Ser Asp Pro Tyr Thr Ser Tyr Ala Tyr Ser Asp Ser Val
                85                  90                  95

Lys Gly Arg Phe Thr Ile Ser Arg Asp Met Ser Lys Asn Thr Val Tyr
                100                 105                 110

Leu Gln Met Asn Arg Leu Arg Ala Glu Asp Thr Ala Val Tyr Tyr Cys
            115                 120                 125

Ala Arg Glu Thr Asn Thr Gly Phe Ser Asn Ser Trp Tyr Leu Asp Phe
        130                 135                 140

Trp Gly Gln Gly Thr Leu Val Thr Val Ser Ser Gly Gly Gly Gly Ser
145                 150                 155                 160

Gly Gly Gly Gly Ser Gly Gly Gly Ser Gln Pro Val Leu Thr Gln
                165                 170                 175

Pro Pro Ser Ala Ser Gly Thr Pro Gly Gln Arg Val Thr Ile Ser Cys
            180                 185                 190

Ser Gly Ser Ser Ser Asn Ile Gly Arg Asn Ile Val Asn Trp Tyr Gln
        195                 200                 205
```

-continued

```
Gln Leu Pro Gly Thr Thr Pro Lys Leu Leu Ile Tyr Ser Asn Asn Gln
    210                 215                 220

Arg Pro Ser Gly Val Pro Asp Arg Phe Ser Gly Ser Lys Ser Gly Thr
225                 230                 235                 240

Ser Ala Ser Leu Ala Ile Ser Gly Leu His Ser Glu Asp Glu Ala Asp
                245                 250                 255

Tyr Tyr Cys Ala Thr Trp Asp Asp Ser Leu Asn Gly Trp Val Phe Gly
            260                 265                 270

Gly Gly Thr Lys Leu Thr Val Leu Ala Lys Pro Thr Thr Thr Pro Ala
        275                 280                 285

Pro Arg Pro Pro Thr Pro Ala Pro Thr Ile Ala Ser Gln Pro Leu Ser
    290                 295                 300

Leu Arg Pro Glu Ala Cys Arg Pro Ala Ala Gly Gly Ala Val His Thr
305                 310                 315                 320

Arg Gly Leu Asp Phe Ala Lys Ile Glu Val Met Tyr Pro Pro Pro Tyr
                325                 330                 335

Leu Asp Asn Glu Lys Ser Asn Gly Thr Ile Ile His Val Lys Gly Lys
            340                 345                 350

His Leu Cys Pro Ser Pro Leu Phe Pro Gly Pro Ser Lys Pro Phe Trp
        355                 360                 365

Val Leu Val Val Val Gly Gly Val Leu Ala Cys Tyr Ser Leu Leu Val
    370                 375                 380

Thr Val Ala Phe Ile Ile Phe Trp Val Arg Ser Lys Arg Ser Arg Leu
385                 390                 395                 400

Leu His Ser Asp Tyr Met Asn Met Thr Pro Arg Arg Pro Gly Pro Thr
                405                 410                 415

Arg Lys His Tyr Gln Pro Tyr Ala Pro Pro Arg Asp Phe Ala Ala Tyr
            420                 425                 430

Arg Ser Arg Val Lys Phe Ser Arg Ser Ala Asp Ala Pro Ala Tyr Gln
        435                 440                 445

Gln Gly Gln Asn Gln Leu Tyr Asn Glu Leu Asn Leu Gly Arg Arg Glu
    450                 455                 460

Glu Tyr Asp Val Leu Asp Lys Arg Arg Gly Arg Asp Pro Glu Met Gly
465                 470                 475                 480

Gly Lys Pro Gln Arg Arg Lys Asn Pro Gln Glu Gly Leu Tyr Asn Glu
                485                 490                 495

Leu Gln Lys Asp Lys Met Ala Glu Ala Tyr Ser Glu Ile Gly Met Lys
            500                 505                 510

Gly Glu Arg Arg Arg Gly Lys Gly His Asp Gly Leu Tyr Gln Gly Leu
        515                 520                 525

Ser Thr Ala Thr Lys Asp Thr Tyr Asp Ala Leu His Met Gln Ala Leu
    530                 535                 540

Pro Pro Arg
545

<210> SEQ ID NO 22
<211> LENGTH: 30
<212> TYPE: DNA
<213> ORGANISM: Homo sapiens

<400> SEQUENCE: 22
gagcagaagc ttatctccga ggaagatctg                                      30
```

CD-38 DIRECTED CHIMERIC ANTIGEN RECEPTOR CONSTRUCTS

This application claims the benefit of priority under 35 U.S.C. § 119 to U.S. provisional application No. 62/581,466, filed Nov. 3, 2017, and entitled "CD38-Directed CAR Constructs", the contents of which is incorporated by reference herein in its entirety.

Throughout this application various publications, patents, and/or patent applications are referenced. The disclosures of the publications, patents and/or patent applications are hereby incorporated by reference in their entireties into this application in order to more fully describe the state of the art to which this disclosure pertains.

SEQUENCE LISTING

The instant application contains a Sequence Listing which has been filed electronically in ASCII format and is hereby incorporated by reference in its entirety. Said ASCII copy, created on Oct. 31, 2018, is named T103019_1210US_1_SL.txt and is 24,386 bytes in size.

TECHNICAL FIELD

The present disclosure provides a solution to a problem of T cell fratricide when making a CD38 CAR transduction by providing a CAR (chimeric antigen receptor) construct directed by an scFv antibody having a heavy chain variable (VH) domain comprising an amino acid sequence that is at least 95% homologous to the amino acid sequence of SEQ ID NO: 1 and a light chain variable (VL) domain having an amino acid sequence that is at least 95% homologous to the amino acid sequence of SEQ ID NO: 3. More specifically, the present disclosure provides a CD38-directed CAR construct that demonstrates higher safety by preferentially binding to higher CD38-expressing tumor cells and not targeting lower-CD38 expressing normal T cells, including CAR-transduced T cells.

BACKGROUND

Novel specificities in T-cells have been generated through the genetic transfer of transgenic T-cell receptors or chimeric antigen receptors (CARs). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and heavy variable fragments of a monoclonal antibody joined by a flexible linker. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), and 4-1BB (CD137) have been added alone (second generation) or in combination (third generation) to enhance survival and increase proliferation of CAR modified T cells. CARs have successfully allowed T cells to be redirected against antigens expressed at the surface of tumor cells from various malignancies including lymphomas and solid tumors.

The current protocol for treatment of patients using adoptive immunotherapy is based on autologous cell transfer. In this approach, T lymphocytes are recovered from patients, genetically modified or selected ex vivo, cultivated in vitro in order to amplify the number of cells if necessary and finally infused into the patient. In addition to lymphocyte infusion, the host (patient) may be manipulated in other ways that support the engraftment of the T cells or their participation in an immune response, for example preconditioning (with radiation or chemotherapy) and administration of lymphocyte growth factors (such as IL-2). Each patient receives an individually fabricated treatment, using the patient's own lymphocytes (i.e. an autologous therapy). Autologous therapies face substantial technical and logistic hurdles to practical application, their generation requires expensive dedicated facilities and expert personnel, they must be generated in a short time following a patient's diagnosis, and in many cases, pretreatment of the patient has resulted in degraded immune function, such that the patient's lymphocytes may be poorly functional and present in very low numbers. Because of these hurdles, each patient's autologous cell preparation is effectively a new product, resulting in substantial variations in efficacy and safety.

For engineered T cells expressing a CAR or a transgenic TCR on-target off-tumor side effects can also include "T cell fratricide", if the target antigen is expressed by the T cells themselves. For a CD38 CAR-T, T cell fratricide was observed during in vitro culture. This was mitigated to some extent using an anti-CD38 antibody that blocked the CAR-target interaction. Such approach, however, has not been tested in vivo. Antibody mediated blocking of fratricide in vivo has only been shown for NK cells in a murine model using a monoclonal antibody against CD244 (Taniguchi et al., (2007) *Blood* 110, 2020-2023).

For T cells expressing a transgenic TCR, fratricide can potentially be circumvented, if an allogeneic T cell donor negative for the targeted HLA-type is used (Leisegang, M., Wilde, S., Spranger, S., Milosevic, S., Frankenberger, B., Uckert, W., and Schendel, D. J. (2010). MHC-restricted fratricide of human lymphocytes expressing surviving-specific transgenic T cell receptors. *The Journal of Clinical Investigation* 120, 3869-3877. Schendel, D. J., and Frankenberger, B. (2013). Limitations for TCR gene therapy by MHC-restricted fratricide and TCR-mediated hematopoietic stem cell toxicity. *Oncoimmunology* 2, e22410).

CD38 is a 45 kD type II transmembrane glycoprotein with a long C-terminal extracellular domain and a short N-terminal cytoplasmic domain. The CD38 protein is a bifunctional ectoenzyme that can catalyze the conversion of NAD into cyclic ADP-ribose (cADPR) and also hydrolyze cADPR into ADP-ribose. During ontogeny, CD38 appears on $CD34^+$ committed stem cells and lineage-committed progenitors of lymphoid, erythroid and myeloid cells. CD38 expression persists mostly in the lymphoid lineage with varying expression levels at different stages of T and B cell development.

CD38 is upregulated in many hematopoietic malignancies and in cell lines derived from various hematopoietic malignancies, including non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML). On the other hand, most primitive pluripotent stem cells of the hematopoietic system are $CD38^-$. CD38 expression in hematopoietic malignancies and its correlation with disease progression makes CD38 an attractive target for anti-CD38 antibody therapy.

Multiple myeloma (MM) is a malignancy of antibody-producing plasma cells and is the third most common hematological cancer worldwide after lymphoma and leukemia (Ferlay et al., *Int. J. Cancer* 136(5): E359-386. 2015). In 2016, the estimated new cases of MM are 30,330 with an estimated death of 12,650 in the U.S. (Howlader et al., "SEER Cancer Statistics Review, 1975-2013, National Cancer Institute. Bethesda, Md., http://seer.cancer.gov/csr/1975_2013/, based on November 2015 SEER data submission, posted to the SEER web site." 2016). Currently there is no cure for this disease and its five-year survival rate is only 45%, despite significant advances in treating MM, including novel immunomodulatory agents, proteasome inhibitors, and autologous hematopoietic stem cell transplantation (Kumar et al., *Blood* 111(5): 2516-2520, 2008; and Kharfan-Dabaja et al. *J. Hematol. Oncol.* 6:2, 2013). The development of novel and effective therapeutic options remains a critical need for MM patients. The present disclosure is provided to address this need.

T cells can penetrate virtually every biologic space and have the power to dispose of normal or malignant cells as seen in viral and autoimmune diseases and are also seen in the rare spontaneous remissions of cancer. However, T cells are easily tolerized to self or tumor antigens, and "immune surveillance" has manifestly failed in every cancer that is clinically apparent. It is the goal of CAR-T studies to supply the specificities and affinities to a patient's T cells, without regard for their "endogenous" T cell receptor (TCR) repertoire, by providing an antibody-defined, anti-malignant cell marker recognition to kill malignant cells based on their expression of antigens recognized by the CAR.

Adoptive immunotherapy by infusion of T cells engineered CARs for redirected tumoricidal activity has been explored for the treating of metastatic cancer. CARs are constructed by joining the antigen recognition domains of an antibody with the signaling domains of receptors from T cells. Modification of T cells with CAR genes equips T cells with retargeted antibody-type antitumor cytotoxicity. Because killing is Major Histocompatibility Complex (MHC)-unrestricted, the approach offers a general therapy for all patients bearing the same antigen. T cells engineered with antigen specific CARs are called "T cells", "CAR-T cells," or "T-bodies" (Eshar, et al., 1993 Proc. Nat'l. Acad. of Sci. USA 90(2):720-724). First-generation CAR, immunoglobulin-T cell receptor (IgTCR), was engineered to contain a signaling domain (TCR-CD3) that delivers an activation stimulus (signal 1) only (Gross, et al., 1989 Proc. Nat'l. Acad. of Sci. USA 86(24):10024-10028; Eshar, et al., 1993 Proc. Nat'l. Acad. of Sci. USA 90(2):720-724; Haynes, et al., 2001 The Journal of Immunology 166(1):182-187). T cells grafted with the first-generation CARs alone exhibit limited anti-tumor efficacy due to suboptimal activation. The 2nd generation CAR, immunoglobulinCD28-CD3ξ-T cell receptor (IgCD28TCR), incorporated a costimulatory CD28 (signal 2) into the first-generation receptor that render the CAR-T cells a greater anti-tumor capacity (Finney, et al., 1998 Journal of Immunology 161(6):2791-2797; Hombach, et al., 2001 Journal of Immunology 167(11):6123-6131; Maher, et al., 2002 Nature Biotechnology 20(1):70-7; Emtage, et al., 2008 Clinical Cancer Research 14(24):8112-812; Lo, et al., 2010 Clinical Cancer Research 16(10):2769-2780).

SUMMARY

The present disclosure provides a chimeric antigen receptor (CAR) construct comprising an anti-CD38 antibody that provides CD38 binding kinetics capable of preferentially targeting tumor cells that are high expressers of CD38 while avoiding lower CD38 expression cells. More specifically, the present disclosure provides a nucleic acid sequence encoding an anti-CD38 chimeric antigen receptor (CAR) construct A2, wherein the CAR construct comprises an scFv antibody having a heavy chain variable (VH) domain comprising an amino acid sequence that is at least 95% homologous to the amino acid sequence of SEQ ID NO: 1 and a light chain variable (VL) domain having an amino acid sequence that is at least 95% homologous to the amino acid sequence of SEQ ID NO: 3; a transmembrane domain; and an intracellular signaling domain. Preferably, the scFv antibody further comprises a peptide linker between the VH and VL comprising the amino acid sequence selected from the group consisting of SEQ ID NO: 5. An anti-CD38 chimeric antigen receptor (CAR) construct can have an scFv antibody region which comprises the amino acid sequence of SEQ ID NO: 12. Preferably, the CAR construct further comprises a hinge region between the antigen binding protein and the transmembrane domain, comprising a CD8 hinge region of SEQ ID NO: 6. Preferably, the CAR construct further comprises a CD28 extracellular domain between the antigen binding protein and the trans membrane domain comprising a CD28 extracellular domain of SEQ ID NO: 7. Preferably, the transmembrane domain is a CD28 transmembrane domain of SEQ ID NO: 8. Preferably, there are two signaling domains. More preferably, a first signaling domain is a CD28 signaling domain having an amino acid sequence of SEQ ID NO: 9. More preferably, a second signaling domain is a CD3-t signaling domain having an amino acid sequence of SEQ ID NO: 10. Preferably, the CAR construct further comprises a signal peptide at the N-terminus.

In another specific embodiment, a nucleic acid sequence encodes an anti-CD38 chimeric antigen receptor (CAR) construct D8, wherein the CAR construct comprises an scFv antibody having a heavy chain variable (VH) domain comprising an amino acid sequence that is at least 95% homologous to the amino acid sequence of SEQ ID NO: 2 and a light chain variable (VL) domain having an amino acid sequence that is at least 95% homologous to the amino acid sequence of SEQ ID NO: 4; a transmembrane domain; and an intracellular signaling domain. Preferably, the scFv antibody further comprises a peptide linker between the VH and VL comprising the amino acid sequence selected from the group consisting of SEQ ID NO: 5. An anti-CD38 chimeric antigen receptor (CAR) construct can have an scFv antibody region which comprises the amino acid sequence of SEQ ID NO: 16. Preferably, the CAR construct further comprises a hinge region between the antigen binding protein and the transmembrane domain, comprising a CD8 hinge region of SEQ ID NO: 6. Preferably, the CAR construct further comprises a CD28 extracellular domain between the antigen binding protein and the trans membrane domain comprising a CD28 extracellular domain of SEQ ID NO: 7. Preferably, the transmembrane domain is a CD28 transmembrane domain of SEQ ID NO: 8. Preferably, there are two signaling domains. More preferably, a first signaling domain is a CD28 signaling domain having an amino acid sequence of SEQ ID NO: 9. More preferably, a second signaling domain is a CD3-ξ signaling domain having an amino acid sequence of SEQ ID NO: 10. Preferably, the CAR construct further comprises a signal peptide at the N-terminus.

The present disclosure further provides a nucleic acid sequence encoding an anti-CD38 CAR, comprising a single chain antibody that binds to CD38, wherein the antigen binding protein comprises a heavy chain variable (VH)

domain comprising an amino acid sequence that is at least 95% identical to, at least 96% identical to, at least 97% identical to, at least 98% identical to, or at least 99% identical to, the amino acid sequence of SEQ ID NO: 1 and comprises a light chain variable (VL) domain comprising an amino acid sequence that is at least 95% identical, at least 96% identical to, at least 97% identical to, at least 98% identical to, or at least 99% identical to the amino acid sequence of SEQ ID NO: 3; a transmembrane domain; and an intracellular domain.

The present disclosure provides a nucleic acid sequence encoding an anti-CD38 CAR comprising an antigen binding protein that binds to CD38, wherein the antigen binding protein comprises a heavy chain variable (VH) domain comprising an amino acid sequence that is at least 95% identical to, at least 96% identical to, at least 97% identical to, at least 98% identical to, or at least 99% identical to the amino acid sequence of SEQ ID NO: 2 and comprises a light chain variable (VL) domain comprising an amino acid sequence that is at least 95% identical to, at least 96% identical to, at least 97% identical to, at least 98% identical to, or at least 99% identical to the amino acid sequence of SEQ ID NO: 4; a transmembrane domain; and an intracellular domain.

The present disclosure further provides methods for conducting adoptive cell therapy by administering to a subject genetically engineered cells expressing the provided anti-CD38 CAR constructs.

The present disclosure further provides a method of treating a human subject having a disorder associated with detrimental CD38 expression. Such a method includes, for example, administering to a human subject a host cell which expresses an anti-CD38 CAR described herein (or a host cell transduced with a nucleic acid sequence encoding an anti-CD38 CAR as described herein). Preferably, the disorder is cancer, including, but not limited to hematologic, breast cancer, ovarian cancer, prostate cancer, head and neck cancer, lung cancer, bladder cancer, melanoma, colorectal cancer, pancreatic cancer, lung cancer, liver cancer, renal cancer, esophageal cancer, leiomyoma, leiomyosarcoma, glioma, and glioblastoma.

Preferably, the cancer is a hematologic cancer selected from the group consisting of non-Hodgkin's lymphoma (NHL), Burkitt's lymphoma (BL), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML). Most preferably, the cancer is multiple myeloma (MM).

The present disclosure provides a nucleic acid sequence encoding an anti-CD38 chimeric antigen receptor (CAR) construct, wherein the encoded construct comprises: (i) an antigen binding protein that binds to CD38, wherein the antigen binding protein comprises a heavy chain variable (VH) domain comprising an amino acid sequence that is at least 95% identical to the amino acid sequence of SEQ ID NO: 1, and wherein the antigen binding protein that binds to CD38 comprises a light chain variable (VL) domain comprising an amino acid sequence that is at least 95% identical to the amino acid sequence of SEQ ID NO: 3; (ii) a transmembrane domain; and (iii) an intracellular domain. In one embodiment, the nucleic acid that encodes the anti-CD38 chimeric antigen receptor (CAR) construct is an isolated nucleic acid.

The present disclosure provides a nucleic acid sequence encoding an anti-CD38 chimeric antigen receptor (CAR) construct, wherein the encoded construct comprises: (i) an antigen binding protein that binds to CD38, wherein the antigen binding protein comprises a heavy chain variable (VH) domain comprising an amino acid sequence that is at least 95% identical to the amino acid sequence of SEQ ID NO: 2, and wherein the antigen binding protein that binds to CD38 comprises a light chain variable (VL) domain comprising an amino acid sequence that is at least 95% identical to the amino acid sequence of SEQ ID NO: 4; (ii) a transmembrane domain; and (iii) an intracellular domain. In one embodiment, the nucleic acid that encodes the anti-CD38 chimeric antigen receptor (CAR) construct is an isolated nucleic acid.

The present disclosure further provides encoded anti-CD38 chimeric antigen receptor (CAR) constructs which further comprise a peptide linker between the heavy chain variable (VH) domain and the light chain variable (VL) domain, wherein the peptide linker comprises the amino acid sequence of SEQ ID NO: 5.

The present disclosure further provides encoded anti-CD38 chimeric antigen receptor (CAR) constructs, wherein the antigen binding protein comprising the amino acid sequence of SEQ ID NO: 12 or 16.

The present disclosure further provides encoded anti-CD38 chimeric antigen receptor (CAR) constructs which further comprises a hinge region between the antigen binding protein and the transmembrane domain, wherein the hinge region is a CD8 hinge region comprising the amino acid sequence of SEQ ID NO. 6, or a functional portion thereof.

The present disclosure further provides encoded anti-CD38 chimeric antigen receptor (CAR) constructs which further comprises a CD28 extracellular domain between the antigen binding protein and the transmembrane domain, wherein the CD28 extracellular domain comprises the amino acid sequence of SEQ ID NO: 7, or a functional portion thereof.

The present disclosure further provides encoded anti-CD38 chimeric antigen receptor (CAR) constructs wherein the transmembrane domain comprises a CD28 transmembrane domain which comprises the amino acid sequence of SEQ ID NO: 8, or a functional portion thereof.

The present disclosure further provides encoded anti-CD38 chimeric antigen receptor (CAR) constructs wherein the intracellular domain comprises a CD28 intracellular domain which comprises the amino acid sequence of SEQ ID NO:9. In one embodiment, the intracellular domain further comprises a CD3-zeta intracellular domain which comprises the amino acid sequence of SEQ ID NO:10. In one embodiment, the intracellular domain further comprises any one or any combination of intracellular domain(s) or co-stimulatory domains from CD28, CD3-zeta, OX-40 (CD134) or 4-1BB (CD137). In one embodiment, the intracellular domain comprises any one or any combination of a CD28 intracellular domain, CD3-zeta, OX-40 and/or 4-1BB. In one embodiment, the nucleic acid encodes a first generation anti-CD38 chimeric antigen receptor (CAR) construct where the intracellular domain comprises CD3-zeta. In one embodiment, the nucleic acid encodes a second generation anti-CD38 chimeric antigen receptor (CAR) construct where the intracellular domain comprises CD3-zeta, and CD28 intracellular domain or 4-1BB. In one embodiment, the nucleic acid encodes a third generation anti-CD38 chimeric antigen receptor (CAR) construct where the intracellular domain comprises CD3-zeta, and CD28 intracellular domain, and 4-1BB or OX-40.

The present disclosure further provides a nucleic acid sequence encoding an anti-CD38 chimeric antigen receptor (CAR) construct comprising an amino acid sequence that is at least 95% identical to the amino acid sequence of SEQ ID NO: 20 or 21. In one embodiment, the nucleic acid that encodes the anti-CD38 chimeric antigen receptor (CAR) construct is an isolated nucleic acid.

The present disclosure further provides an expression vector operably linked to a nucleic acid sequence encoding an anti-CD38 chimeric antigen receptor (CAR) construct, wherein the encoded construct comprises: (i) an antigen binding protein that binds to CD38, wherein the antigen binding protein comprises a heavy chain variable (VH) domain comprising an amino acid sequence that is at least 95% identical to the amino acid sequence of SEQ ID NO: 1, and wherein the antigen binding protein that binds to CD38 comprises a light chain variable (VL) domain comprising an amino acid sequence that is at least 95% identical to the amino acid sequence of SEQ ID NO: 3; (ii) a transmembrane domain; and (iii) an intracellular domain. In one embodiment, the expression vector directs expression of the anti-CD38 chimeric antigen receptor (CAR) construct in a host cell or in a population of host cells. In one embodiment, the expression vector comprises a retroviral or lentiviral expression vector. In one embodiment, the expression vector is part of an expression vector system having one or more additional vectors for host cell transducing and/or packaging.

The present disclosure further provides an expression vector operably linked to a nucleic acid sequence encoding an anti-CD38 chimeric antigen receptor (CAR) construct, wherein the encoded construct comprises: (i) an antigen binding protein that binds to CD38, wherein the antigen binding protein comprises a heavy chain variable (VH) domain comprising an amino acid sequence that is at least 95% identical to the amino acid sequence of SEQ ID NO: 2, and wherein the antigen binding protein that binds to CD38 comprises a light chain variable (VL) domain comprising an amino acid sequence that is at least 95% identical to the amino acid sequence of SEQ ID NO: 4; (ii) a transmembrane domain; and (iii) an intracellular domain. In one embodiment, the expression vector directs expression of the anti-CD38 chimeric antigen receptor (CAR) construct in a host cell or in a population of host cells. In one embodiment, the expression vector comprises a retroviral or lentiviral expression vector. In one embodiment, the expression vector is part of an expression vector system having one or more additional vectors for host cell transducing and/or packaging.

In one embodiment, the expression vector directs expression of the anti-CD38 chimeric antigen receptor (CAR) construct in a host cell or a population of host cells. In one embodiment, the expression vector comprises nucleic acid backbone sequences derived from a retrovirus or lentivirus. In one embodiment, the expression vector is a part of a viral transducing system that includes one or more packaging vectors and/or envelope vectors, and together, the these vectors direct expression of the transgene in the host cell.

The present disclosure further provides an expression vector that is part of a first or second generation retroviral expression vector system. In one embodiment, a first generation expression vector system comprises a retroviral expression vector (transfer vector) operably linked to a nucleic acid encoding an anti-CD38 chimeric antigen receptor (CAR) construct, an envelope vector carrying retroviral env sequences, and a packaging vector carrying retroviral gag and pol sequences. In one embodiment, a second generation expression vector system comprises an expression vector operably linked to a nucleic acid encoding an anti-CD38 chimeric antigen receptor (CAR) construct, and retroviral gag, pol and env sequences stably expressed in a packaging cell line.

The present disclosure further provide an expression vector that is part of a first, second or third generation lentiviral expression vector system. In one embodiment, a first generation expression vector system comprises lentiviral expression vector (transfer vector) operably linked to a nucleic acid encoding an anti-CD38 chimeric antigen receptor (CAR) construct, an envelope vector carrying lentiviral env sequences, and a lentiviral packaging vector carrying gag, pol, tat and rev sequences. In one embodiment, a second generation expression vector system comprises a lentiviral expression vector operably linked to a nucleic acid encoding an anti-CD38 chimeric antigen receptor (CAR) construct, an envelope vector carrying a non-lentiviral env sequence (heterologous env sequence), and a packaging vector carrying lentiviral gag, pol, tat and rev sequences. In one embodiment, a third generation expression vector system comprises a lentiviral expression vector operably linked to a nucleic acid encoding an anti-CD38 chimeric antigen receptor (CAR) construct and having a lentiviral tat sequence removed from the 3' LTR, a first packaging plasmid (gag and pol), a second packaging plasmid (rev), and envelope plasmid (carrying a heterologous env sequence).

The present disclosure further provides an expression vector, and one or more packaging vectors, that can direct transient introduction of the transgene into the host cells or stable insertion of the transgene into the host cells' genome. The expression vector, and one or more packaging vectors, can direct transcription and/or translation of the transgene in the host cell. The expression vector, which is operably linked to the nucleic acid encoding the anti-CD38 chimeric antigen receptor (CAR) construct, along with the one or more packaging vectors, can direct production of the anti-CD38 chimeric antigen receptor (CAR) construct which can be displayed on the surface of the transduced host cell.

The present disclosure further provides an expression vector operably linked to a nucleic acid sequence encoding an anti-CD38 chimeric antigen receptor (CAR) construct, wherein the CAR construct further comprises a peptide linker between the heavy chain variable (VH) domain and the light chain variable (VL) domain, wherein the peptide linker comprises the amino acid sequence of SEQ ID NO: 5.

The present disclosure further provides an expression vector operably linked to a nucleic acid sequence encoding an anti-CD38 chimeric antigen receptor (CAR) construct, wherein the antigen binding protein comprising the amino acid sequence of SEQ ID NO: 12 or 16.

The present disclosure further provides an expression vector operably linked to a nucleic acid sequence encoding an anti-CD38 chimeric antigen receptor (CAR) construct, wherein the CAR construct further comprises a hinge region between the antigen binding protein and the transmembrane domain, wherein the hinge region is a CD8 hinge region comprising the amino acid sequence of SEQ ID NO. 6, or a functional portion thereof.

The present disclosure further provides an expression vector operably linked to a nucleic acid sequence encoding an anti-CD38 chimeric antigen receptor (CAR) construct, wherein the CAR construct further comprises a CD28 extracellular domain between the antigen binding protein and the transmembrane domain, wherein the CD28 extracellular domain comprises the amino acid sequence of SEQ ID NO: 7, or a functional portion thereof.

The present disclosure further provides an expression vector operably linked to a nucleic acid sequence encoding an anti-CD38 chimeric antigen receptor (CAR) construct, wherein the transmembrane domain comprises a CD28 transmembrane domain which comprises the amino acid sequence of SEQ ID NO: 8, or a functional portion thereof.

The present disclosure further provides an expression vector operably linked to a nucleic acid sequence encoding an anti-CD38 chimeric antigen receptor (CAR) construct, wherein the intracellular domain comprises a CD28 intracellular domain which comprises the amino acid sequence of SEQ ID NO:9. In one embodiment, the intracellular domain further comprises a CD3-zeta intracellular domain which comprises the amino acid sequence of SEQ ID NO:10. In one embodiment, the intracellular domain further comprises any one or any combination of intracellular domain(s) or co-stimulatory domains from CD28, CD3-zeta, OX-40 (CD134) or 4-1BB (CD137). In one embodiment, the intracellular domain comprises any one or any combination of a CD28 intracellular domain, CD3-zeta, OX-40 and/or 4-1BB. In one embodiment, the nucleic acid encodes a first generation anti-CD38 chimeric antigen receptor (CAR) construct where the intracellular domain comprises CD3-zeta. In one embodiment, the nucleic acid encodes a second generation anti-CD38 chimeric antigen receptor (CAR) construct where the intracellular domain comprises CD3-zeta, and CD28 intracellular domain or 4-1BB. In one embodiment, the nucleic acid encodes a third generation anti-CD38 chimeric antigen receptor (CAR) construct where the intracellular domain comprises CD3-zeta, and CD28 intracellular domain, and 4-1BB or OX-40.

The present disclosure further provides an expression vector operably linked to a nucleic acid sequence encoding an anti-CD38 chimeric antigen receptor (CAR) construct, wherein the CAR construct comprises an amino acid sequence that is at least 95% identical to the amino acid sequence of SEQ ID NO: 20 or 21. In one embodiment, the nucleic acid that encodes the anti-CD38 chimeric antigen receptor (CAR) construct is an isolated nucleic acid.

The present disclosure further provides an anti-CD38 chimeric antigen receptor (CAR) construct that preferentially binds cells (e.g., target cells) exhibiting high expression of CD38 compared to cells exhibiting lower CD38 expression.

The present disclosure further provides an anti-CD38 chimeric antigen receptor (CAR) construct comprising: (i) an antigen binding protein that binds to CD38, wherein the antigen binding protein comprises a heavy chain variable (VH) domain comprising an amino acid sequence that is at least 95% identical to the amino acid sequence of SEQ ID NO: 1, and the antigen binding protein that binds to CD38 comprises a light chain variable (VL) domain comprising an amino acid sequence that is at least 95% identical to the amino acid sequence of SEQ ID NO: 3; (ii) a transmembrane domain; and (iii) an intracellular domain. In one embodiment, the anti-CD38 chimeric antigen receptor (CAR) construct is an isolated polypeptide.

The present disclosure further provides an anti-CD38 chimeric antigen receptor (CAR) construct comprising: (i) an antigen binding protein that binds to CD38, wherein the antigen binding protein comprises a heavy chain variable (VH) domain comprising an amino acid sequence that is at least 95% identical to the amino acid sequence of SEQ ID NO: 2, and the antigen binding protein that binds to CD38 comprises a light chain variable (VL) domain comprising an amino acid sequence that is at least 95% identical to the amino acid sequence of SEQ ID NO: 4; (ii) a transmembrane domain; and (iii) an intracellular domain. In one embodiment, the anti-CD38 chimeric antigen receptor (CAR) construct is an isolated polypeptide.

The present disclosure further provides an antigen binding protein which further comprises a peptide linker between the heavy chain variable (VH) domain and the light chain variable (VL) domain, and wherein the peptide linker comprises the amino acid sequence of SEQ ID NO: 5.

The present disclosure further provides encoded anti-CD38 chimeric antigen receptor (CAR) constructs, wherein the antigen binding protein comprising the amino acid sequence of SEQ ID NO: 12 or 16.

The present disclosure further provides an anti-CD38 chimeric antigen receptor (CAR) construct which further comprises a hinge region between the antigen binding protein and the transmembrane domain, wherein the hinge region is a CD8 hinge region comprising the amino acid sequence of SEQ ID NO: 6, or a functional portion thereof.

The present disclosure further provides an anti-CD38 chimeric antigen receptor (CAR) construct which further comprises a CD28 extracellular domain between the antigen binding protein and the transmembrane domain, wherein the CD28 extracellular domain comprises the amino acid sequence of SEQ ID NO: 7, or a functional portion thereof.

The present disclosure further provides an anti-CD38 chimeric antigen receptor (CAR) construct, wherein the transmembrane domain comprises a CD28 transmembrane domain which comprises the amino acid sequence of SEQ ID NO: 8, or a functional portion thereof.

The present disclosure further provides an anti-CD38 chimeric antigen receptor (CAR) construct, wherein the intracellular domain comprises a CD28 intracellular domain which comprises the amino acid sequence of SEQ ID NO:9. In one embodiment, the intracellular domain further comprises a CD3-zeta intracellular domain which comprises the amino acid sequence of SEQ ID NO:10. In one embodiment, the intracellular domain further comprises any one or any combination of intracellular domain(s) or co-stimulatory domains from CD28, CD3-zeta, OX-40 (CD134) or 4-1BB (CD137). In one embodiment, the intracellular domain comprises any one or any combination of a CD28 intracellular domain, CD3-zeta, OX-40 and/or 4-1BB. In one embodiment, the nucleic acid encodes a first generation anti-CD38 chimeric antigen receptor (CAR) construct where the intracellular domain comprises CD3-zeta. In one embodiment, the nucleic acid encodes a second generation anti-CD38 chimeric antigen receptor (CAR) construct where the intracellular domain comprises CD3-zeta, and CD28 intracellular domain or 4-1BB. In one embodiment, the nucleic acid encodes a third generation anti-CD38 chimeric antigen receptor (CAR) construct where the intracellular domain comprises CD3-zeta, and CD28 intracellular domain, and 4-1BB or OX-40.

The present disclosure further provides an anti-CD38 chimeric antigen receptor (CAR) construct comprising an amino acid sequence that is at least 95% identical to the amino acid sequence of SEQ ID NO:20 or 21. In one embodiment, the anti-CD38 chimeric antigen receptor (CAR) construct is an isolated polypeptide.

The present disclosure further provides a host cell, or a population of host cells, transduced with a nucleic acid sequence encoding an anti-CD38 chimeric antigen receptor (CAR) construct, wherein the encoded anti-CD38 chimeric antigen receptor (CAR) construct comprises: (i) an antigen binding protein that binds to CD38, wherein the antigen binding protein comprises a heavy chain variable (VH) domain comprising an amino acid sequence that is at least 95% identical to the amino acid sequence of SEQ ID NO: 1, and wherein the antigen binding protein comprises a light chain variable (VL) domain comprising an amino acid sequence that is at least 95% identical to the amino acid sequence of SEQ ID NO: 3; (ii) a transmembrane domain; and (iii) an intracellular domain. In one embodiment, the host cell or the population of host cells are selected from a group consisting of T host cells, placental derived natural killer host cells (or a population thereof), and cord blood derived natural killer host cells (or a population thereof). In one embodiment, in the transduced host cell or in the population of transduced cells, the nucleic acid sequence encoding the anti-CD38 chimeric antigen receptor (CAR) construct is operably linked to an expression vector which directs expression of the anti-CD38 chimeric antigen receptor (CAR) construct in the host cell or the population of host cells.

The present disclosure further provides a host cell, or a population of host cells, transduced with a nucleic acid sequence encoding an anti-CD38 chimeric antigen receptor (CAR) construct, wherein the encoded anti-CD38 chimeric antigen receptor (CAR) construct comprises: (i) an antigen binding protein that binds to CD38, wherein the antigen binding protein comprises a heavy chain variable (VH) domain comprising an amino acid sequence that is at least 95% identical to the amino acid sequence of SEQ ID NO: 2, and wherein the antigen binding protein comprises a light chain variable (VL) domain comprising an amino acid sequence that is at least 95% identical to the amino acid sequence of SEQ ID NO: 4; (ii) a transmembrane domain; and (iii) an intracellular domain. In one embodiment, the host cell or the population of host cells are selected from a group consisting of T host cells, placental derived natural killer host cells (or a population thereof), and cord blood derived natural killer host cells (or a population thereof). In one embodiment, in the transduced host cell or in the population of transduced cells, the nucleic acid sequence encoding the anti-CD38 chimeric antigen receptor (CAR) construct is operably linked to an expression vector which directs expression of the anti-CD38 chimeric antigen receptor (CAR) construct in the host cell or the population of host cells.

The present disclosure further provides a host cell, or a population of host cells, transduced with a nucleic acid sequence encoding an anti-CD38 chimeric antigen receptor (CAR) construct which further comprises a peptide linker between the heavy chain variable (VH) domain and the light chain variable (VL) domain, and wherein the peptide linker comprises the amino acid sequence of SEQ ID NO: 5.

The present disclosure further provides a host cell, or a population of host cells, transduced with a nucleic acid sequence encoding an anti-CD38 chimeric antigen receptor (CAR) construct, wherein the antigen binding protein comprising the amino acid sequence of SEQ ID NO: 12 or 16.

The present disclosure further provides a host cell, or a population of host cells, transduced with a nucleic acid sequence encoding an anti-CD38 chimeric antigen receptor (CAR) construct which further comprises a hinge region between the antigen binding protein and the transmembrane domain, wherein the hinge region is a CD8 hinge region comprising the amino acid sequence of SEQ ID NO. 6, or a functional portion thereof.

The present disclosure further provides a host cell, or a population of host cells, transduced with a nucleic acid sequence encoding an anti-CD38 chimeric antigen receptor (CAR) construct which further comprises a CD28 extracellular domain between the antigen binding protein and the transmembrane domain, wherein the CD28 extracellular domain comprises the amino acid sequence of SEQ ID NO: 7, or a functional portion thereof.

The present disclosure further provides a host cell, or a population of host cells, transduced with a nucleic acid sequence encoding an anti-CD38 chimeric antigen receptor (CAR) construct wherein the transmembrane domain comprises a CD28 transmembrane domain which comprises the amino acid sequence of SEQ ID NO: 8, or a functional portion thereof.

The present disclosure further provides a host cell, or a population of host cells, transduced with a nucleic acid sequence encoding an anti-CD38 chimeric antigen receptor (CAR) construct, wherein the intracellular domain comprises a CD28 intracellular domain which comprises the amino acid sequence of SEQ ID NO:9. In one embodiment, the intracellular domain further comprises a CD3-zeta intracellular domain which comprises the amino acid sequence of SEQ ID NO:10. In one embodiment, the intracellular domain further comprises any one or any combination of intracellular domain(s) or co-stimulatory domains from CD28, CD3-zeta, OX-40 (CD134) or 4-1BB (CD137). In one embodiment, the intracellular domain comprises any one or any combination of a CD28 intracellular domain, CD3-zeta, OX-40 and/or 4-1BB. In one embodiment, the nucleic acid encodes a first generation anti-CD38 chimeric antigen receptor (CAR) construct where the intracellular domain comprises CD3-zeta. In one embodiment, the nucleic acid encodes a second generation anti-CD38 chimeric antigen receptor (CAR) construct where the intracellular domain comprises CD3-zeta, and CD28 intracellular domain or 4-1BB. In one embodiment, the nucleic acid encodes a third generation anti-CD38 chimeric antigen receptor (CAR) construct where the intracellular domain comprises CD3-zeta, and CD28 intracellular domain, and 4-1BB or OX-40.

The present disclosure further provides a host cell, or a population of host cells, transduced with a nucleic acid sequence encoding an anti-CD38 chimeric antigen receptor (CAR) construct, wherein the encoded construct comprises an amino acid sequence that is at least 95% identical to the amino acid sequence of SEQ ID NO:20 or 21.

The present disclosure further provides a host cell or a population of host cells which are transduced with the nucleic acid sequence encoding an anti-CD38 chimeric antigen receptor (CAR) construct, wherein the nucleic acid sequence is operably linked to an expression vector which directs expression of the anti-CD38 chimeric antigen receptor (CAR) in the host cell.

The present disclosure further provides a host cell or a population of host cells that express the anti-CD38 chimeric antigen receptor (CAR) construct, wherein the expressed anti-CD38 chimeric antigen receptor (CAR) construct on the host cell or population of host cells preferentially bind cells (e.g., target cells) exhibiting high expression of CD38 compared to cells exhibiting lower CD38 expression.

The present disclosure further provides a host cell, or a population of host cells, which express an anti-CD38 chimeric antigen receptor (CAR) construct which comprises: (i) an antigen binding protein that binds to CD38, wherein the antigen binding protein comprises a heavy chain variable (VH) domain comprising an amino acid sequence that is at least 95% identical to the amino acid sequence of SEQ ID NO: 1 and comprises a light chain variable (VL) domain comprising an amino acid sequence that is at least 95% identical to the amino acid sequence of SEQ ID NO: 3; (ii) a transmembrane domain; and (iii) an intracellular domain. In one embodiment, the host cell or population of host cells are transduced with an expression vector operably linked to a nucleic acid encoding the anti-CD38 chimeric antigen receptor (CAR) construct. In one embodiment, the expression vector directs expression of the anti-CD38 chimeric antigen receptor (CAR) construct in the host cell or the population of host cells. In one embodiment, the expression vector comprises a retroviral or lentiviral expression vector. In one embodiment, the host cell or the population of host cells are selected from a group consisting of T host cells, placental derived natural killer host cells (or a population thereof), and cord blood derived natural killer host cells (or a population thereof).

The present disclosure further provides a host cell, or a population of host cells, which express an anti-CD38 chimeric antigen receptor (CAR) construct which comprises: (i) an antigen binding protein that binds to CD38, wherein the antigen binding protein comprises a heavy chain variable (VH) domain comprising an amino acid sequence that is at least 95% identical to the amino acid sequence of SEQ ID NO: 2 and comprises a light chain variable (VL) domain comprising an amino acid sequence that is at least 95% identical to the amino acid sequence of SEQ ID NO: 4; (ii) a transmembrane domain; and (iii) an intracellular domain. In one embodiment, the host cell or population of host cells are transduced with an expression vector operably linked to a nucleic acid encoding the anti-CD38 chimeric antigen receptor (CAR) construct. In one embodiment, the expression vector directs expression of the anti-CD38 chimeric antigen receptor (CAR) construct in the host cell or the population of host cells. In one embodiment, the expression vector comprises a retroviral or lentiviral expression vector. In one embodiment, the host cell or the population of host cells are selected from a group consisting of T host cells, placental derived natural killer host cells (or a population thereof), and cord blood derived natural killer host cells (or a population thereof).

In one embodiment, in the host cell or population of host cells that express the anti-CD38 chimeric antigen receptor (CAR) construct, the host cell or population of host cells are selected from a group consisting of a T host cell (or a population thereof), a placental derived natural killer host cell (or a population thereof), and a cord blood derived natural killer host cell (or a population thereof).

In one embodiment, in the host cell or population of host cells that express the anti-CD38 chimeric antigen receptor (CAR) construct, the anti-CD38 chimeric antigen receptor (CAR) construct further comprises a peptide linker between the heavy chain variable (VH) domain and the light chain variable (VL) domain, wherein the peptide linker comprises the amino acid sequence of SEQ ID NO: 5.

In one embodiment, in the host cell or population of host cells that express the anti-CD38 chimeric antigen receptor (CAR) construct, the antigen binding protein comprises the amino acid sequence of SEQ ID NO: 12 or 16.

In one embodiment, in the host cell or population of host cells that express the anti-CD38 chimeric antigen receptor (CAR) construct, the anti-CD38 chimeric antigen receptor (CAR) construct further comprises a hinge region between the antigen binding protein and the transmembrane domain, wherein the hinge region is a CD8 hinge region comprising the amino acid sequence of SEQ ID NO. 6.

In one embodiment, in the host cell or population of host cells that express the anti-CD38 chimeric antigen receptor (CAR) construct, the anti-CD38 chimeric antigen receptor (CAR) construct further comprises a CD28 extracellular domain between the antigen binding protein and the transmembrane domain, wherein the CD28 extracellular domain comprises the amino acid sequence of SEQ ID NO: 7.

In one embodiment, in the host cell or population of host cells that express the anti-CD38 chimeric antigen receptor (CAR) construct, the transmembrane domain is a CD28 transmembrane domain which comprises the amino acid sequence of SEQ ID NO: 8.

In one embodiment, in the host cell or population of host cells that express the anti-CD38 chimeric antigen receptor (CAR) construct, the intracellular domain comprises a CD28 intracellular domain which comprises the amino acid sequence of SEQ ID NO:9. In one embodiment, the intracellular domain further comprises a CD3-zeta intracellular domain which comprises the amino acid sequence of SEQ ID NO:10. In one embodiment, the intracellular domain further comprises any one or any combination of intracellular domain(s) or co-stimulatory domains from CD28, CD3-zeta, OX-40 (CD134) or 4-1BB (CD137). In one embodiment, the intracellular domain comprises any one or any combination of a CD28 intracellular domain, CD3-zeta, OX-40 and/or 4-1BB. In one embodiment, the nucleic acid encodes a first generation anti-CD38 chimeric antigen receptor (CAR) construct where the intracellular domain comprises CD3-zeta. In one embodiment, the nucleic acid encodes a second generation anti-CD38 chimeric antigen receptor (CAR) construct where the intracellular domain comprises CD3-zeta, and CD28 intracellular domain or 4-1BB. In one embodiment, the nucleic acid encodes a third generation anti-CD38 chimeric antigen receptor (CAR) construct where the intracellular domain comprises CD3-zeta, and CD28 intracellular domain, and 4-1BB or OX-40.

In one embodiment, in the host cell or population of host cells that express the anti-CD38 chimeric antigen receptor (CAR) construct, the anti-CD38 chimeric antigen receptor (CAR) construct comprises an amino acid sequence that is at least 95% identical to the amino acid sequence of SEQ ID NO: 20 or 21.

In one embodiment, in the host cell or population of host cells that express the anti-CD38 chimeric antigen receptor (CAR) construct, the expression vector is operably linked to a nucleic acid sequence encoding any of the anti-CD38 chimeric antigen receptor (CAR) constructs of the present disclosure. In one embodiment, the expression vector comprises an expression vector which directs expression of the anti-CD38 chimeric antigen receptor (CAR) construct in a host cell or a population of host cells. In one embodiment, the expression vector comprises nucleic acid backbone sequences derived a retrovirus or lentivirus. In one embodiment, the expression vector is a part of a viral transducing system that includes one or more packaging vectors, and together, the expression vector and packaging vector(s) direct expression of the transgene in the host cell. The expression vector, and one or more packaging vectors, can direct transient introduction of the transgene into the host cells or stable insertion of the transgene into the host cells' genome. The expression vector, and one or more packaging vectors, can direct transcription and/or translation of the transgene in the host cell. The expression vector, which is operably linked to the nucleic acid encoding the anti-CD38 chimeric antigen receptor (CAR) construct, along with the one or more packaging vectors, can direct production of the anti-CD38 chimeric antigen receptor (CAR) construct which can be displayed on the surface of the transduced host cell.

The present disclosure further provides a method for preparing a transduced host cell or a population of transduced cells comprising: transducing under suitable conditions host cell or a population of host cells with a nucleic acid sequence encoding an anti-CD38 chimeric antigen receptor (CAR) construct, wherein the encoded construct comprises (i) an antigen binding protein that binds to CD38, wherein the antigen binding protein comprises a heavy chain variable (VH) domain comprising an amino acid sequence that is at least 95% identical to the amino acid sequence of SEQ ID NO: 1, and wherein the antigen binding protein that binds to CD38 comprises a light chain variable (VL) domain comprising an amino acid sequence that is at least 95% identical to the amino acid sequence of SEQ ID NO: 3; (ii) a transmembrane domain; and (iii) an intracellular domain. In one embodiment, the nucleic acid sequence encoding an anti-CD38 chimeric antigen receptor (CAR) construct is operably linked to an expression vector which directs expression of the anti-CD38 chimeric antigen receptor (CAR) construct in a host cell or a population of host cells. In one embodiment, the host cell or the population of host cells are selected from a group consisting of T host cells, placental derived natural killer host cells (or a population thereof), and cord blood derived natural killer host cells (or a population thereof).

The present disclosure further provides a method for preparing a transduced host cell or a population of transduced cells comprising: transducing under suitable conditions host cell or a population of host cells with a nucleic acid sequence encoding an anti-CD38 chimeric antigen receptor (CAR) construct, wherein the encoded construct comprises (i) an antigen binding protein that binds to CD38, wherein the antigen binding protein comprises a heavy chain variable (VH) domain comprising an amino acid sequence that is at least 95% identical to the amino acid sequence of SEQ ID NO: 2, and wherein the antigen binding protein that binds to CD38 comprises a light chain variable (VL) domain comprising an amino acid sequence that is at least 95% identical to the amino acid sequence of SEQ ID NO: 4; (ii) a transmembrane domain; and (iii) an intracellular domain. In one embodiment, the nucleic acid sequence encoding an anti-CD38 chimeric antigen receptor (CAR) construct is operably linked to an expression vector which directs expression of the anti-CD38 chimeric antigen receptor (CAR) construct in the host cell or population of host cells. In one embodiment, the host cell or the population of host cells are selected from a group consisting of T host cells, placental derived natural killer host cells (or a population thereof), and cord blood derived natural killer host cells (or a population thereof).

In one embodiment, in the methods for preparing a transduced host cell or population of host cells, the encoded anti-CD38 chimeric antigen receptor (CAR) construct further comprises a peptide linker between the heavy chain variable (VH) domain and the light chain variable (VL) domain, and wherein the peptide linker comprises the amino acid sequence of SEQ ID NO: 5.

In one embodiment, in the methods for preparing a transduced host cell or population of host cells, the encoded anti-CD38 chimeric antigen receptor (CAR) construct comprises an antigen binding protein comprising the amino acid sequence of SEQ ID NO: 12 or 16.

In one embodiment, in the methods for preparing a transduced host cell or population of host cells, the encoded anti-CD38 chimeric antigen receptor (CAR) construct further comprises a a hinge region between the antigen binding protein and the transmembrane domain, wherein the hinge region is a CD8 hinge region comprising the amino acid sequence of SEQ ID NO. 6, or a functional portion thereof.

In one embodiment, in the methods for preparing a transduced host cell or population of host cells, the encoded anti-CD38 chimeric antigen receptor (CAR) construct further comprises a CD28 extracellular domain between the antigen binding protein and the transmembrane domain, wherein the CD28 extracellular domain comprises the amino acid sequence of SEQ ID NO: 7, or a functional portion thereof.

In one embodiment, in the methods for preparing a transduced host cell or population of host cells, the transmembrane domain comprises a CD28 transmembrane domain which comprises the amino acid sequence of SEQ ID NO: 8, or a functional portion thereof.

In one embodiment, in the methods for preparing a transduced host cell or population of host cells, the intracellular domain comprises a CD28 intracellular domain which comprises the amino acid sequence of SEQ ID NO:9. In one embodiment, the intracellular domain further comprises a CD3-zeta intracellular domain which comprises the amino acid sequence of SEQ ID NO:10. In one embodiment, the intracellular domain further comprises any one or any combination of intracellular domain(s) or co-stimulatory domains from CD28, CD3-zeta, OX-40 (CD134) or 4-1BB (CD137). In one embodiment, the intracellular domain comprises any one or any combination of a CD28 intracellular domain, CD3-zeta, OX-40 and/or 4-1BB. In one embodiment, the nucleic acid encodes a first generation anti-CD38 chimeric antigen receptor (CAR) construct where the intracellular domain comprises CD3-zeta. In one embodiment, the nucleic acid encodes a second generation anti-CD38 chimeric antigen receptor (CAR) construct where the intracellular domain comprises CD3-zeta, and CD28 intracellular domain or 4-1BB. In one embodiment, the nucleic acid encodes a third generation anti-CD38 chimeric antigen receptor (CAR) construct where the intracellular domain comprises CD3-zeta, and CD28 intracellular domain, and 4-1BB or OX-40.

The present disclosure further provides a method for preparing a transduced host cell or a population of transduced cells comprising: transducing under suitable conditions a host cell or a population of host cells with a nucleic acid sequence encoding an anti-CD38 chimeric antigen receptor (CAR) construct, wherein the encoded construct is at least 95% identical to the amino acid sequence of SEQ ID NO: 21 or 22. In one embodiment, the nucleic acid sequence encoding an anti-CD38 chimeric antigen receptor (CAR) construct is operably linked to an expression vector which directs expression of the anti-CD38 chimeric antigen receptor (CAR) construct in the host cell or population of host cells. In one embodiment, the host cell or the population of host cells are selected from a group consisting of T host cells, placental derived natural killer host cells (or a population thereof), and cord blood derived natural killer host cells (or a population thereof).

In one embodiment, in the methods for preparing a transduced host cell or population of host cells, the expression vector is operably linked to a nucleic acid sequence encoding any of the anti-CD38 chimeric antigen receptor (CAR) constructs of the present disclosure. In one embodiment, the expression vector comprises an expression vector which directs expression of the anti-CD38 chimeric antigen receptor (CAR) construct in a host cell or a population of host cells. In one embodiment, the expression vector comprises nucleic acid backbone sequences derived from the viral family Retroviridae which includes retroviral and lentiviral vectors. In one embodiment, the expression vector is a part of a viral transducing system that includes one or more packaging vectors, and together, the expression vector and packaging vector(s) direct expression of the transgene in the host cell. The expression vector, and one or more packaging vectors, can direct transient introduction of the transgene into the host cells or stable insertion of the transgene into the host cells' genome. The expression vector, and one or more packaging vectors, can direct transcription and/or translation of the transgene in the host cell. The expression vector, which is operably linked to the nucleic acid encoding the anti-CD38 chimeric antigen receptor (CAR) construct, along with the one or more packaging vectors, can direct production of the anti-CD38 chimeric antigen receptor (CAR) construct which can be displayed on the surface of the transduced host cell.

The present disclosure further provides a method for long-term stable culturing a population of host cells, comprising culturing a population of host cells transduced with a nucleic acid sequence encoding an anti-CD38 chimeric antigen receptor (CAR) construct under conditions suitable to expand the number of host cells carrying the nucleic acid sequence, wherein the cultured host cells exhibit reduced T-cell fratricide in vitro, and wherein the host cells preferentially bind and kill cells that exhibit high expression of CD38 compared to cells exhibiting lower CD38 expression.

The present disclosure further provides a method for culturing a population of host cells comprising: culturing a population of host cells transduced with a nucleic acid sequence encoding an anti-CD38 chimeric antigen receptor (CAR) construct under conditions suitable to expand the number of host cells carrying the nucleic acid sequence, wherein the encoded construct comprises (i) an antigen binding protein that binds to CD38, wherein the antigen binding protein comprises a heavy chain variable (VH) domain comprising an amino acid sequence that is at least 95% identical to the amino acid sequence of SEQ ID NO: 1, and the antigen binding protein that bind to CD38 comprises a light chain variable (VL) domain comprising an amino acid sequence that is at least 95% identical to the amino acid sequence of SEQ ID NO: 3; (ii) a transmembrane domain; and (iii) an intracellular domain.

The present disclosure further provides a method for culturing a population of host cells comprising: culturing a population of host cells transduced with a nucleic acid sequence encoding an anti-CD38 chimeric antigen receptor (CAR) construct under conditions suitable to expand the number of host cells carrying the nucleic acid sequence, wherein the encoded construct comprises (i) an antigen binding protein that binds to CD38, wherein the antigen binding protein comprises a heavy chain variable (VH) domain comprising an amino acid sequence that is at least 95% identical to the amino acid sequence of SEQ ID NO: 2, and the antigen binding protein that bind to CD38 comprises a light chain variable (VL) domain comprising an amino acid sequence that is at least 95% identical to the amino acid sequence of SEQ ID NO: 4; (ii) a transmembrane domain; and (iii) an intracellular domain.

In one embodiment, in the methods for culturing a population of host cells, the encoded anti-CD38 chimeric antigen receptor (CAR) construct further comprises a peptide linker between the heavy chain variable (VH) domain and the light chain variable (VL) domain, and wherein the peptide linker comprises the amino acid sequence of SEQ ID NO: 5.

In one embodiment, in the methods for culturing a population of host cells, the encoded anti-CD38 chimeric antigen receptor (CAR) construct comprises the antigen binding protein comprising the amino acid sequence of SEQ ID NO: 12 or 16.

In one embodiment, in the methods for culturing a population of host cells, the encoded anti-CD38 chimeric antigen receptor (CAR) construct further comprises a hinge region between the antigen binding protein and the transmembrane domain, wherein the hinge region is a CD8 hinge region comprising the amino acid sequence of SEQ ID NO. 6, or a functional portion thereof.

In one embodiment, in the methods for culturing a population of host cells, the encoded anti-CD38 chimeric antigen receptor (CAR) construct further comprises a CD28 extracellular domain between the antigen binding protein and the transmembrane domain, wherein the CD28 extracellular domain comprises the amino acid sequence of SEQ ID NO: 7, or a functional portion thereof.

In one embodiment, in the methods for culturing a population of host cells, the transmembrane domain comprises a CD28 transmembrane domain which comprises the amino acid sequence of SEQ ID NO: 8, or a functional portion thereof.

In one embodiment, in the methods for culturing a population of host cells, the intracellular domain comprises a CD28 intracellular domain which comprises the amino acid sequence of SEQ ID NO:9. In one embodiment, the intracellular domain further comprises a CD3-zeta intracellular domain which comprises the amino acid sequence of SEQ ID NO:10. In one embodiment, the intracellular domain further comprises any one or any combination of intracellular domain(s) or co-stimulatory domains from CD28, CD3-zeta, OX-40 (CD134) or 4-1BB (CD137). In one embodiment, the intracellular domain comprises any one or any combination of a CD28 intracellular domain, CD3-zeta, OX-40 and/or 4-1BB. In one embodiment, the nucleic acid encodes a first generation anti-CD38 chimeric antigen receptor (CAR) construct where the intracellular domain comprises CD3-zeta. In one embodiment, the nucleic acid encodes a second generation anti-CD38 chimeric antigen receptor (CAR) construct where the intracellular domain comprises CD3-zeta, and CD28 intracellular domain or 4-1BB. In one embodiment, the nucleic acid encodes a third generation anti-CD38 chimeric antigen receptor (CAR) construct where the intracellular domain comprises CD3-zeta, and CD28 intracellular domain, and 4-1BB or OX-40.

The present disclosure further provides a method for culturing a population of host cells comprising: culturing a population of host cells transduced with a nucleic acid sequence encoding an anti-CD38 chimeric antigen receptor (CAR) construct under conditions suitable to expand the number of host cells carrying the nucleic acid sequence, wherein the encoded construct is at least 95% identical to the amino acid sequence of SEQ ID NO: 21 or 22.

In one embodiment, in the methods for culturing a population of host cells, the population of host cells is selected from a group consisting of a population of host T cells, a population of placental derived natural killer host cells, and a population cord blood derived natural killer host cells. In one embodiment, the nucleic acid sequence encoding an anti-CD38 chimeric antigen receptor (CAR) construct is operably linked to an expression vector. In one embodiment, the expression vector directs expression of the anti-CD38 chimeric antigen receptor (CAR) construct in the population of host cells.

The present disclosure further provides a method for expressing an anti-CD38 chimeric antigen receptor (CAR) construct comprising: subjecting a population of host cells to conditions suitable to express the anti-CD38 chimeric antigen receptor (CAR) construct, wherein the population of host cells are transduced with an expression vector which comprises a nucleic acid sequence encoding the anti-CD38 chimeric antigen receptor (CAR) construct, wherein the encoded construct comprises (i) an antigen binding protein that binds to CD38, wherein the antigen binding protein comprises a heavy chain variable (VH) domain comprising an amino acid sequence that is at least 95% identical to the amino acid sequence of SEQ ID NO: 1, and the antigen binding protein that bind to CD38 comprises a light chain variable (VL) domain comprising an amino acid sequence that is at least 95% identical to the amino acid sequence of SEQ ID NO: 3; (ii) a transmembrane domain; and (iii) an intracellular domain. In one embodiment, the expression vector is operably linked to a nucleic acid sequence encoding the anti-CD38 chimeric antigen receptor (CAR) construct, where the expression vector directs expression of the anti-CD38 chimeric antigen receptor (CAR) construct in the population of host cells. In one embodiment, the population of host cells that express the anti-CD38 chimeric antigen receptor (CAR) construct preferentially bind cells (e.g., target cells) exhibiting high expression of CD38 compared to cells exhibiting lower CD38 expression.

The present disclosure further provides a method for expressing an anti-CD38 chimeric antigen receptor (CAR) construct comprising: subjecting a population of host cells to conditions suitable to express the anti-CD38 chimeric antigen receptor (CAR) construct, wherein the population of host cells are transduced with an expression vector which comprises a nucleic acid sequence encoding the anti-CD38 chimeric antigen receptor (CAR) construct, wherein the encoded construct comprises (i) an antigen binding protein that binds to CD38, wherein the antigen binding protein comprises a heavy chain variable (VH) domain comprising an amino acid sequence that is at least 95% identical to the amino acid sequence of SEQ ID NO: 2, and the antigen binding protein that bind to CD38 comprises a light chain variable (VL) domain comprising an amino acid sequence that is at least 95% identical to the amino acid sequence of SEQ ID NO: 4; (ii) a transmembrane domain; and (iii) an intracellular domain. In one embodiment, the expression vector is operably linked to a nucleic acid sequence encoding the anti-CD38 chimeric antigen receptor (CAR) construct, where the expression vector directs expression of the anti-CD38 chimeric antigen receptor (CAR) construct in the population of host cells. In one embodiment, the population of host cells that express the anti-CD38 chimeric antigen receptor (CAR) construct preferentially bind cells (e.g., target cells) exhibiting high expression of CD38 compared to cells exhibiting lower CD38 expression.

In one embodiment, in the methods for expressing an anti-CD38 chimeric antigen receptor (CAR) construct, the encoded anti-CD38 chimeric antigen receptor (CAR) construct further comprises a peptide linker between the heavy chain variable (VH) domain and the light chain variable (VL) domain, and wherein the peptide linker comprises the amino acid sequence of SEQ ID NO: 5.

In one embodiment, in the methods for expressing an anti-CD38 chimeric antigen receptor (CAR) construct, the encoded anti-CD38 chimeric antigen receptor (CAR) construct comprises the antigen binding protein comprising the amino acid sequence of SEQ ID NO: 12 or 16.

In one embodiment, in the methods for expressing an anti-CD38 chimeric antigen receptor (CAR) construct, the encoded anti-CD38 chimeric antigen receptor (CAR) construct further comprises a hinge region between the antigen binding protein and the transmembrane domain, wherein the hinge region is a CD8 hinge region comprising the amino acid sequence of SEQ ID NO. 6, or a functional portion thereof.

In one embodiment, in the methods for expressing an anti-CD38 chimeric antigen receptor (CAR) construct, the encoded anti-CD38 chimeric antigen receptor (CAR) construct further comprises a CD28 extracellular domain between the antigen binding protein and the transmembrane domain, wherein the CD28 extracellular domain comprises the amino acid sequence of SEQ ID NO: 7, or a functional portion thereof.

In one embodiment, in the methods for expressing an anti-CD38 chimeric antigen receptor (CAR) construct, the transmembrane domain comprises a CD28 transmembrane domain which comprises the amino acid sequence of SEQ ID NO: 8, or a functional portion thereof.

In one embodiment, in the methods for expressing an anti-CD38 chimeric antigen receptor (CAR) construct, the intracellular domain comprises a CD28 intracellular domain which comprises the amino acid sequence of SEQ ID NO:9. In one embodiment, the intracellular domain further comprises a CD3-zeta intracellular domain which comprises the amino acid sequence of SEQ ID NO:10. In one embodiment, the intracellular domain further comprises any one or any combination of intracellular domain(s) or co-stimulatory domains from CD28, CD3-zeta, OX-40 (CD134) or 4-1BB (CD137). In one embodiment, the intracellular domain comprises any one or any combination of a CD28 intracellular domain, CD3-zeta, OX-40 and/or 4-1BB. In one embodiment, the nucleic acid encodes a first generation anti-CD38 chimeric antigen receptor (CAR) construct where the intracellular domain comprises CD3-zeta. In one embodiment, the nucleic acid encodes a second generation anti-CD38 chimeric antigen receptor (CAR) construct where the intracellular domain comprises CD3-zeta, and CD28 intracellular domain or 4-1BB. In one embodiment, the nucleic acid encodes a third generation anti-CD38 chimeric antigen receptor (CAR) construct where the intracellular domain comprises CD3-zeta, and CD28 intracellular domain, and 4-1BB or OX-40.

The present disclosure further provides a method for expressing an anti-CD38 chimeric antigen receptor (CAR) construct comprising: subjecting a population of host cells to conditions suitable to express the anti-CD38 chimeric antigen receptor (CAR) construct, wherein the population of host cells are transduced with an expression vector which comprises a nucleic acid sequence encoding the anti-CD38 chimeric antigen receptor (CAR) construct, wherein the encoded construct is at least 95% identical to the amino acid sequence of SEQ ID NO: 21 or 22.

In one embodiment, in the methods for expressing the anti-CD38 chimeric antigen receptor (CAR) construct in a population of host cells, the population of host cells is selected from a group consisting of a population of host T cells, a population of placental derived natural killer host cells, and a population cord blood derived natural killer host cells. In one embodiment, the nucleic acid sequence encoding an anti-CD38 chimeric antigen receptor (CAR) construct is operably linked to an expression vector. In one embodiment, the expression vector directs expression of the anti-CD38 chimeric antigen receptor (CAR) construct in the population of host cells.

In one embodiment, in the methods for expressing the anti-CD38 chimeric antigen receptor (CAR) construct in a population of host cells, the expression vector is operably linked to a nucleic acid sequence encoding any of the anti-CD38 chimeric antigen receptor (CAR) constructs of the present disclosure. In one embodiment, the expression vector comprises an expression vector which directs expression of the anti-CD38 chimeric antigen receptor (CAR) construct in a host cell or a population of host cells. In one embodiment, the expression vector comprises nucleic acid backbone sequences derived from the viral family Retroviridae which includes retroviral and lentiviral vectors. In one embodiment, the expression vector is a part of a viral transducing system that includes one or more packaging vectors, and together, the expression vector and packaging vector(s) direct expression of the transgene in the host cell. The expression vector, and one or more packaging vectors, can direct transient introduction of the transgene into the host cells or stable insertion of the transgene into the host cells' genome. The expression vector, and one or more packaging vectors, can direct transcription and/or translation of the transgene in the host cell. The expression vector, which is operably linked to the nucleic acid encoding the anti-CD38 chimeric antigen receptor (CAR) construct, along with the one or more packaging vectors, can direct production of the anti-CD38 chimeric antigen receptor (CAR) construct which can be displayed on the surface of the transduced host cell.

The present disclosure further provides a method for inducing cytokine release comprising: contacting a population of host cells expressing an anti-CD38 chimeric antigen receptor (CAR) construct with target cells expressing CD38 under conditions suitable to induce cytokine release, wherein the anti-CD38 chimeric antigen receptor (CAR) construct comprises (i) an antigen binding protein that binds to CD38, wherein the antigen binding protein comprises a heavy chain variable (VH) domain comprising an amino acid sequence that is at least 95% identical to the amino acid sequence of SEQ ID NO: 1, and the antigen binding protein that bind to CD38 comprises a light chain variable (VL) domain comprising an amino acid sequence that is at least 95% identical to the amino acid sequence of SEQ ID NO: 3; (ii) a transmembrane domain; and (iii) an intracellular domain. In one embodiment, the cytokine comprises interferon-γ or IL-2. In one embodiment, the host cells expressing an anti-CD38 chimeric antigen receptor (CAR) construct preferentially bind cells (e.g., target cells) exhibiting high expression of CD38 compared to cells exhibiting lower CD38 expression.

The present disclosure further provides a method for inducing cytokine release comprising: contacting a population of host cells expressing an anti-CD38 chimeric antigen receptor (CAR) construct with target cells expressing CD38 under conditions suitable to induce cytokine release, wherein the anti-CD38 chimeric antigen receptor (CAR) construct comprises (i) an antigen binding protein that binds to CD38, wherein the antigen binding protein comprises a heavy chain variable (VH) domain comprising an amino acid sequence that is at least 95% identical to the amino acid sequence of SEQ ID NO: 2, and the antigen binding protein that bind to CD38 comprises a light chain variable (VL) domain comprising an amino acid sequence that is at least 95% identical to the amino acid sequence of SEQ ID NO: 4; (ii) a transmembrane domain; and (iii) an intracellular domain. In one embodiment, the cytokine comprises interferon-γ or IL-2. In one embodiment, the host cells expressing an anti-CD38 chimeric antigen receptor (CAR) construct preferentially bind cells (e.g., target cells) exhibiting high expression of CD38 compared to cells exhibiting lower CD38 expression.

In one embodiment, in the methods for inducing cytokine release, the encoded anti-CD38 chimeric antigen receptor (CAR) construct further comprises a peptide linker between the heavy chain variable (VH) domain and the light chain variable (VL) domain, and wherein the peptide linker comprises the amino acid sequence of SEQ ID NO: 5.

In one embodiment, in the methods for inducing cytokine release, the encoded anti-CD38 chimeric antigen receptor (CAR) construct comprises antigen binding protein comprising the amino acid sequence of SEQ ID NO: 12 or 16.

In one embodiment, in the methods for inducing cytokine release, the encoded anti-CD38 chimeric antigen receptor (CAR) construct further comprises a hinge region between the antigen binding protein and the transmembrane domain, wherein the hinge region is a CD8 hinge region comprising the amino acid sequence of SEQ ID NO. 6, or a functional portion thereof.

In one embodiment, in the methods for inducing cytokine release, the encoded anti-CD38 chimeric antigen receptor (CAR) construct further comprises a CD28 extracellular domain between the antigen binding protein and the transmembrane domain, wherein the CD28 extracellular domain comprises the amino acid sequence of SEQ ID NO: 7, or a functional portion thereof.

In one embodiment, in the methods for inducing cytokine release, the transmembrane domain comprises a CD28 transmembrane domain which comprises the amino acid sequence of SEQ ID NO: 8, or a functional portion thereof.

In one embodiment, in the methods for inducing cytokine release, the intracellular domain comprises a CD28 intracellular domain which comprises the amino acid sequence of SEQ ID NO:9. In one embodiment, the intracellular domain further comprises a CD3-zeta intracellular domain which comprises the amino acid sequence of SEQ ID NO:10. In one embodiment, the intracellular domain further comprises any one or any combination of intracellular domain(s) or co-stimulatory domains from CD28, CD3-zeta, OX-40 (CD134) or 4-1BB (CD137). In one embodiment, the intracellular domain comprises any one or any combination of a CD28 intracellular domain, CD3-zeta, OX-40 and/or 4-1BB. In one embodiment, the nucleic acid encodes a first generation anti-CD38 chimeric antigen receptor (CAR) construct where the intracellular domain comprises CD3-zeta. In one embodiment, the nucleic acid encodes a second generation anti-CD38 chimeric antigen receptor (CAR) construct where the intracellular domain comprises CD3-zeta, and CD28 intracellular domain or 4-1BB. In one embodiment, the nucleic acid encodes a third generation anti-CD38 chimeric antigen receptor (CAR) construct where the intracellular domain comprises CD3-zeta, and CD28 intracellular domain, and 4-1BB or OX-40.

The present disclosure further provides a method for inducing cytokine release comprising: contacting a population of T host cells expressing an anti-CD38 chimeric antigen receptor (CAR) construct with target cells expressing CD38 under conditions suitable to induce cytokine release, wherein the anti-CD38 chimeric antigen receptor (CAR) construct is at least 95% identical to the amino acid sequence of SEQ ID NO: 21 or 22. In one embodiment, the cytokine comprises interferon-γ or IL-2.

In one embodiment, in the methods for inducing cytokine release, the population of host cells is selected from a group consisting of a population of host T cells, a population of placental derived natural killer host cells, and a population cord blood derived natural killer host cells.

The present disclosure further provides a method for inducing T cell cytotoxicity comprising: contacting a population of T host cells expressing an anti-CD38 chimeric antigen receptor (CAR) construct with target cells expressing CD38 under conditions suitable to induce target cell killing, wherein the population of T host cells are transduced with a nucleic acid sequence encoding an anti-CD38 chimeric antigen receptor (CAR) construct, wherein the encoded construct comprises (i) an antigen binding protein that binds to CD38, wherein the antigen binding protein comprises a heavy chain variable (VH) domain comprising an amino acid sequence that is at least 95% identical to the amino acid sequence of SEQ ID NO: 1, and the antigen binding protein that bind to CD38 comprises a light chain variable (VL) domain comprising an amino acid sequence that is at least 95% identical to the amino acid sequence of SEQ ID NO: 3; (ii) a transmembrane domain; and (iii) an intracellular domain. In one embodiment, the population of host cells that express the anti-CD38 chimeric antigen receptor (CAR) construct preferentially bind cells (e.g., target cells) exhibiting high expression of CD38 compared to cells exhibiting lower CD38 expression.

The present disclosure further provides a method for inducing T cell cytotoxicity comprising: contacting a population of T host cells expressing an anti-CD38 chimeric antigen receptor (CAR) construct with target cells expressing CD38 under conditions suitable to induce target cell killing, wherein the population of T host cells are transduced with a nucleic acid sequence encoding an anti-CD38 chimeric antigen receptor (CAR) construct, wherein the encoded construct comprises (i) an antigen binding protein that binds to CD38, wherein the antigen binding protein comprises a heavy chain variable (VH) domain comprising an amino acid sequence that is at least 95% identical to the amino acid sequence of SEQ ID NO: 2, and the antigen binding protein that bind to CD38 comprises a light chain variable (VL) domain comprising an amino acid sequence that is at least 95% identical to the amino acid sequence of SEQ ID NO: 4; (ii) a transmembrane domain; and (iii) an intracellular domain. In one embodiment, the population of host cells that express the anti-CD38 chimeric antigen receptor (CAR) construct preferentially bind cells (e.g., target cells) exhibiting high expression of CD38 compared to cells exhibiting lower CD38 expression.

In one embodiment, in the methods for inducing T cell cytotoxicity, the encoded anti-CD38 chimeric antigen receptor (CAR) construct further comprises a peptide linker between the heavy chain variable (VH) domain and the light chain variable (VL) domain, and wherein the peptide linker comprises the amino acid sequence of SEQ ID NO: 5.

In one embodiment, in the methods for inducing T cell cytotoxicity, the encoded anti-CD38 chimeric antigen receptor (CAR) construct comprises the antigen binding protein comprising the amino acid sequence of SEQ ID NO: 12 or 16.

In one embodiment, in the methods for inducing T cell cytotoxicity, the encoded anti-CD38 chimeric antigen receptor (CAR) construct further comprises a hinge region between the antigen binding protein and the transmembrane domain, wherein the hinge region is a CD8 hinge region comprising the amino acid sequence of SEQ ID NO. 6, or a functional portion thereof.

In one embodiment, in the methods for inducing T cell cytotoxicity, the encoded anti-CD38 chimeric antigen receptor (CAR) construct further comprises a CD28 extracellular domain between the antigen binding protein and the transmembrane domain, wherein the CD28 extracellular domain comprises the amino acid sequence of SEQ ID NO: 7, or a functional portion thereof.

In one embodiment, in the methods for inducing T cell cytotoxicity, the transmembrane domain comprises a CD28 transmembrane domain which comprises the amino acid sequence of SEQ ID NO: 8, or a functional portion thereof.

In one embodiment, in the methods for inducing T cell cytotoxicity, the intracellular domain comprises a CD28 intracellular domain which comprises the amino acid sequence of SEQ ID NO:9. In one embodiment, the intracellular domain further comprises a CD3-zeta intracellular domain which comprises the amino acid sequence of SEQ ID NO:10. In one embodiment, the intracellular domain further comprises any one or any combination of intracellular domain(s) or co-stimulatory domains from CD28, CD3-zeta, OX-40 (CD134) or 4-1BB (CD137). In one embodiment, the intracellular domain comprises any one or any combination of a CD28 intracellular domain, CD3-zeta, OX-40 and/or 4-1BB. In one embodiment, the nucleic acid encodes a first generation anti-CD38 chimeric antigen receptor (CAR) construct where the intracellular domain comprises CD3-zeta. In one embodiment, the nucleic acid encodes a second generation anti-CD38 chimeric antigen receptor (CAR) construct where the intracellular domain comprises CD3-zeta, and CD28 intracellular domain or 4-1BB. In one embodiment, the nucleic acid encodes a third generation anti-CD38 chimeric antigen receptor (CAR) construct where the intracellular domain comprises CD3-zeta, and CD28 intracellular domain, and 4-1BB or OX-40.

The present disclosure further provides a method for inducing T cell cytotoxicity comprising: contacting a population of T host cells expressing an anti-CD38 chimeric antigen receptor (CAR) construct with target cells expressing CD38 under conditions suitable to induce target cell killing, wherein the population of T host cells are transduced with a nucleic acid sequence encoding an anti-CD38 chimeric antigen receptor (CAR) construct, wherein the encoded construct is at least 95% identical to the amino acid sequence of SEQ ID NO: 21 or 22.

In one embodiment, in the methods for inducing T cell cytotoxicity, the target cells comprise cancer target cells expressing CD38.

The present disclosure further provides a method for treating a cancer or inhibiting tumor growth in a subject in need of a treatment comprising: administering to the subject a population of T host cells expressing an anti-CD38 chimeric antigen receptor (CAR) construct, wherein the construct comprises (i) an antigen binding protein that binds to CD38, wherein the antigen binding protein comprises a heavy chain variable (VH) domain comprising an amino acid sequence that is at least 95% identical to the amino acid sequence of SEQ ID NO: 1, and the antigen binding protein that bind to CD38 comprises a light chain variable (VL) domain comprising an amino acid sequence that is at least 95% identical to the amino acid sequence of SEQ ID NO: 3; (ii) a transmembrane domain; and (iii) an intracellular domain. In one embodiment, the cancer or tumor growth in the subject exhibits upregulated CD38 expression. In one embodiment, the population of T host cells that express the anti-CD38 chimeric antigen receptor (CAR) construct preferentially bind cells (e.g., target tumor cells) exhibiting high expression of CD38 compared to cells exhibiting lower CD38 expression.

The present disclosure further provides a method for treating a cancer or inhibiting tumor growth in a subject in need of a treatment comprising: administering to the subject a population of T host cells expressing an anti-CD38 chimeric antigen receptor (CAR) construct, wherein the construct comprises (i) an antigen binding protein that binds to CD38, wherein the antigen binding protein comprises a heavy chain variable (VH) domain comprising an amino acid sequence that is at least 95% identical to the amino acid sequence of SEQ ID NO: 2, and the antigen binding protein that bind to CD38 comprises a light chain variable (VL) domain comprising an amino acid sequence that is at least 95% identical to the amino acid sequence of SEQ ID NO: 4; (ii) a transmembrane domain; and (iii) an intracellular domain. In one embodiment, the cancer or tumor growth in the subject exhibits upregulated CD38 expression. In one embodiment, the population of host cells that express the anti-CD38 chimeric antigen receptor (CAR) construct preferentially bind cells (e.g., target tumor cells) exhibiting high expression of CD38 compared to cells exhibiting lower CD38 expression.

In one embodiment, in the methods for treating a cancer or inhibiting tumor growth in a subject in need of a treatment, the encoded anti-CD38 chimeric antigen receptor (CAR) construct further comprises a peptide linker between the heavy chain variable (VH) domain and the light chain variable (VL) domain, and wherein the peptide linker comprises the amino acid sequence of SEQ ID NO: 5.

In one embodiment, in the methods for treating a cancer or inhibiting tumor growth in a subject in need of a treatment, the encoded anti-CD38 chimeric antigen receptor (CAR) construct comprises the antigen binding protein comprising the amino acid sequence of SEQ ID NO: 12 or 16.

In one embodiment, in the methods for treating a cancer or inhibiting tumor growth in a subject in need of a treatment, the encoded anti-CD38 chimeric antigen receptor (CAR) construct further comprises a hinge region between the antigen binding protein and the transmembrane domain, wherein the hinge region is a CD8 hinge region comprising the amino acid sequence of SEQ ID NO. 6, or a functional portion thereof.

In one embodiment, in the methods for treating a cancer or inhibiting tumor growth in a subject in need of a treatment, the encoded anti-CD38 chimeric antigen receptor (CAR) construct further comprises a CD28 extracellular domain between the antigen binding protein and the transmembrane domain, wherein the CD28 extracellular domain comprises the amino acid sequence of SEQ ID NO: 7, or a functional portion thereof.

In one embodiment, in the methods for treating a cancer or inhibiting tumor growth in a subject in need of a treatment, the transmembrane domain comprises a CD28 transmembrane domain which comprises the amino acid sequence of SEQ ID NO: 8, or a functional portion thereof.

In one embodiment, in the methods for treating a cancer or inhibiting tumor growth in a subject in need of a treatment, the intracellular domain comprises a CD28 intracellular domain which comprises the amino acid sequence of SEQ ID NO:9. In one embodiment, the intracellular domain further comprises a CD3-zeta intracellular domain which comprises the amino acid sequence of SEQ ID NO:10. In one embodiment, the intracellular domain further comprises any one or any combination of intracellular domain(s) or co-stimulatory domains from CD28, CD3-zeta, OX-40 (CD134) or 4-1BB (CD137). In one embodiment, the intracellular domain comprises any one or any combination of a CD28 intracellular domain, CD3-zeta, OX-40 and/or 4-1BB. In one embodiment, the nucleic acid encodes a first generation anti-CD38 chimeric antigen receptor (CAR) construct where the intracellular domain comprises CD3-zeta. In one embodiment, the nucleic acid encodes a second generation anti-CD38 chimeric antigen receptor (CAR) construct where the intracellular domain comprises CD3-zeta, and CD28 intracellular domain or 4-1BB. In one embodiment, the nucleic acid encodes a third generation anti-CD38 chimeric antigen receptor (CAR) construct where the intracellular domain comprises CD3-zeta, and CD28 intracellular domain, and 4-1BB or OX-40.

The present disclosure further provides a method for treating a cancer or inhibiting tumor growth in a subject in need of treatment comprising: administering to the subject a population of T host cells expressing an anti-CD38 chimeric antigen receptor (CAR) construct, wherein the construct is at least 95% identical to the amino acid sequence of SEQ ID NO: 21 or 22.

In one embodiment, in the methods for treating a cancer or inhibiting tumor growth in a subject, the subject in need of treatment has a disorder associated with over-expression or detrimental expression of CD38.

The present disclosure further provides a method for treating a cancer or inhibiting tumor growth in a subject in need of treatment, wherein the cancer comprises a hematologic cancer which is selected from a group consisting of non-Hodgkin's lymphoma (NHL), Burkitt's lymphoma (BL), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML).

DESCRIPTION OF THE DRAWINGS

FIG. 1A is a schematic representation of Anti-CD38 A2 CAR, which is a structure of the disclosed "Anti-CD38 A2 CAR".

FIG. 1B is a schematic representation of retroviral vector expressing Anti-CD38 A2 CAR. Anti-CD38 A2 CAR was created by linking scFv of anti-CD38 antibody clone A2 to the CD28 transmembrane domain (TMD) and intracellular signaling domain and the CD3ξ intracellular signaling domain, with an intervening spacer derived from the hinge portion of CD8α. A signal peptide from human antibody heavy chain and a myc tag for identifying the expressing of CAR were added to the N-terminus.

DETAILED DESCRIPTION

Figures 2A, 2B:
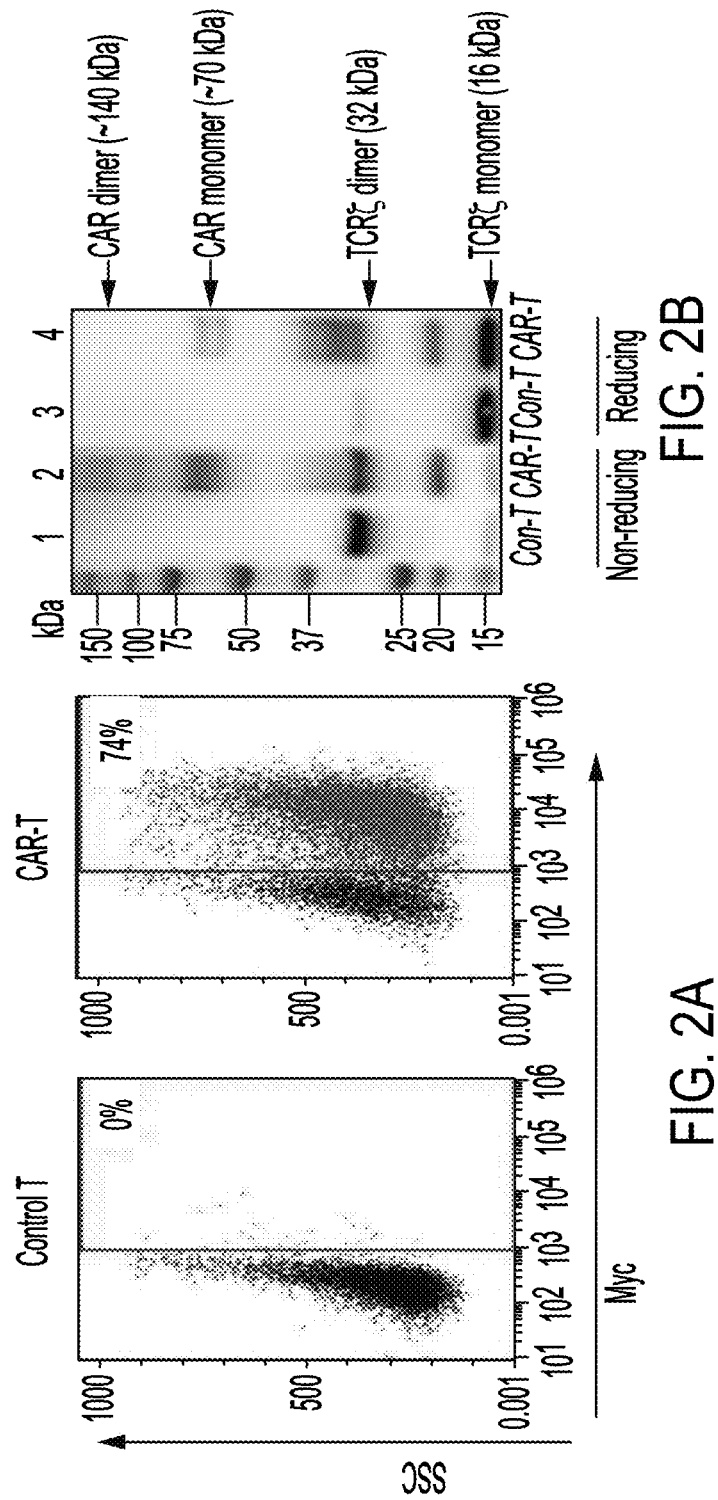
FIG. 2A shows data of non-transduced control T cells and Anti-CD38 A2 CAR transduced T cells which were analyzed after transduction by flow cytometry. The data verify that the transduced T cells express the Anti-CD38 A2 construct.
FIG. 2B is a Western blot showing homodimer formation of CAR2-AntiCD38A2 CAR in CAR-T cells. Membrane fractions of non-transduced control and CAR2-AntiCD38A2 CAR transduced activated T cells under non-reducing and reducing conditions were detected by Western blot using CD3ξ antibody. Positions of monomer and dimer of CAR and TCR ξ are indicated on the right. Molecular mass markers (kDa) are indicated on the left. The CAR2-AntiCD38A2 CAR was detected as monomer with molecular weight of ~70 kDa under reducing conditions and homodimer with molecular weight of 140 kDa in non-reducing conditions. These results show that CAR2-AntiCD38A2 CAR forms homodimers on the CAR-T cell surface.

The disclosed chimeric antigen receptor (CAR) constructs preferentially bind to tumor cells that have high expression of CD38 and not normal cells that exhibit lower CD38 expression levels. It is this differential binding that addresses an issue of auto-lysis. Without being bound by theory, the disclosed CARs exhibit superior side effect profiles and are able to be grown up in culture because the disclosed CAR constructs, when transduced, appear to avoid auto-lysis in cells with lower CD38 expression and moderate CD38 expression while lysing those cells with higher CD38 expression. Stated otherwise, the binding characteristics of the antibody component of the CAR construct achieves a lower and more favorable binding characteristic to CD38.

Definitions

The term "isolated" refers to a protein (e.g., an antibody) or polynucleotide that is substantially free of other cellular material. A protein may be rendered substantially free of naturally associated components (or components associated with the cellular expression system used to produce the antibody) by isolation, using protein purification techniques well known in the art. In one embodiment, the anti-CD38 chimeric antigen receptors, antibodies, or antigen binding fragments, of the disclosure are isolated.

The terms "nucleic acid", "polynucleotide" and "oligonucleotide" and are used interchangeably and refers to polymers of nucleotides. Nucleic acids include naturally-occurring and recombinant forms. Nucleic acids include DNA molecules (cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. Nucleic acid molecule can be single-stranded or double-stranded. In one embodiment, the nucleic acid molecules of the disclosure comprise a contiguous open reading frame encoding an antibody, or a fragment or scFv, derivative, mutein, or variant thereof.

The terms "peptide", "polypeptide" and "protein" are used interchangeably and refer to a polymer of amino acids and are not limited to any particular length. Polypeptides comprise natural and non-natural amino acids. Polypeptides can be naturally-occurring or recombinant forms. These terms encompass native and artificial proteins, protein fragments and polypeptide analogs (such as muteins, variants, chimeric proteins and fusion proteins) of a protein sequence as well as post-translationally, or otherwise covalently or non-covalently, modified proteins. A peptide, polypeptide, or protein may be monomeric or polymeric. Polypeptides includes antibodies, antibody chains, scFv and chimeric antigen receptor constructs.

The "percent identity" or "percent homology" refers to a quantitative measurement of the similarity between two polypeptide or between two polynucleotide sequences. The percent identity between two polypeptide sequences is a function of the number of identical amino acids at aligned positions that are shared between the two polypeptide sequences, taking into account the number of gaps, and the length of each gap, which may need to be introduced to optimize alignment of the two polypeptide sequences. In a similar manner, the percent identity between two polynucleotide sequences is a function of the number of identical nucleotides at aligned positions that are shared between the two polynucleotide sequences, taking into account the number of gaps, and the length of each gap, which may need to be introduced to optimize alignment of the two polynucleotide sequences. A comparison of the sequences and determination of the percent identity between two polypeptide sequences, or between two polynucleotide sequences, may be accomplished using a mathematical algorithm. For example, the "percent identity" or "percent homology" of two polypeptide or two polynucleotide sequences may be determined by comparing the sequences using the GAP computer program (a part of the GCG Wisconsin Package, version 10.3 (Accelrys, San Diego, Calif.)) using its default parameters.

The terms "Chimeric Antigen Receptor" or "CAR" describes a fusion protein comprising an extracellular antigen-binding protein, preferably a single chain variable fragment (scFv or sFv) derived from fusing the variable heavy and light regions of a monoclonal antibody, that is fused to an intracellular signaling domain capable of activating or stimulating an immune cell. Alternatively, scFvs may be used that are derived from Fab's (instead of from an antibody, e.g., obtained from Fab libraries).

The term "antibody" describes an immunoglobulin (Ig) molecule comprised of four polypeptide chains, two heavy (H) chains and two light (L) chains, or any functional fragment, mutant, variant, or derivation thereof, which retains the essential epitope binding features of an Ig molecule.

The terms "anti-CD38 antibody" and "an antibody that binds to CD38" refer to an antibody that is capable of binding CD38.

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634 and 6,696,245).

A "vector" refers to a nucleic acid molecule (e.g., DNA or RNA) which can be operably linked to foreign genetic material (e.g., nucleic acid transgene). Vectors can be single-stranded or double-stranded nucleic acid molecules. Vectors can be linear or circular nucleic acid molecules. Vectors can be used as a vehicle to introduce foreign genetic material into a cell (e.g., host cell). One type of vector is a "plasmid," which refers to a linear or circular double stranded extrachromosomal DNA molecule which can be linked to a transgene, and is capable of replicating in a host cell, and transcribing and translating the transgene. A viral vector typically contains viral RNA or DNA backbone sequences which can be linked to the transgene. The viral backbone sequences can be modified to disable infection but retain insertion of the viral backbone and the co-linked transgene into a host cell genome. Examples of viral vectors include retroviral, lentiviral and adenoviral vectors. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can contain one or more regulatory sequences, such as inducible and/or constitutive promoters, or ribosomal binding sites, which directs transcription, or transcription and translation, of a transgene linked to the expression vector which is transduced into a host cell.

A transgene is "operably linked" to a vector when there is linkage between the transgene and the vector to permit functioning or expression of the vector sequences contained in the vector. Vector sequences can any one or any combination of an original-of-replication sequence, an inducible or constitutive promoter or enhancer sequence, at least one selectable marker sequence, 5' and 3' LTR sequences, and optionally viral env, pol and/or gag sequences.

A transgene is "operably linked" to a regulatory sequence when the regulatory sequence affects the expression (e.g., the level, timing, or location of expression) of the transgene. A "regulatory sequence" is a nucleic acid sequence that affects the expression (e.g., the level, timing, or location of expression) of a transgene to which it is operably linked. The regulatory sequence can, for example, exert its effects directly on the regulated nucleic acid, or through the action of one or more other molecules (e.g., polypeptides that bind to the regulatory sequence and/or the nucleic acid). Regulatory sequences can be part of a vector. Examples of regulatory sequences include promoters, enhancers, ribosomal binding sites and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, *Nucleic Acids Res.* 23:3605-3606.

A "host cell" or "or a population of host cells" refers to a cell (or a population thereof) into which foreign (exogenous) nucleic acids have been introduced. The foreign nucleic acids can include an expression vector operably linked to a transgene, and the host cell can be used to express the foreign nucleic acid (transgene). In one example, the host cell (or population thereof) can be introduced with an expression vector operably linked to a nucleic acid encoding the chimeric antigen receptors (CAR) described herein. A host cell (or a population thereof) can be a cultured cell or can be extracted from a subject. The host cell (or a population thereof) includes the primary subject cell and its progeny without any regard for the number of passages. Progeny cells may or may not harbor identical genetic material compared to the parent cell. Host cells encompass progeny cells.

A host cell can be a prokaryotic cell, for example, *E. coli*, or it can be a eukaryotic cell, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include RPMI8226 (Gentry et al., 2004 *Leuk. Res.* 28(3): 307-313), and human chronic myelogenous leukemia cell line K562. Other examples include the COS-7 line of monkey kidney cells (ATCC CRL 1651) (Gluzman et al., 1981, Cell 23:175), L cells, C127 cells, 3T3 cells (ATCC CCL 163), Chinese hamster ovary (CHO) cells or their derivatives such as Veggie CHO and related cell lines which grow in serum-free media (Rasmussen et al., 1998, *Cytotechnology* 28:31) or CHO strain DX-B 11, which is deficient in DHFR (Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. In one embodiment, a host cell is a mammalian host cell, for example a human host cell. Typically, a host cell is primary cell or a cultured cell that can be introduced with an exogenous polypeptide-encoding nucleic acid which can then be expressed in the host cell. It is understood that the term host cell refers to the particular subject cell and also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

A host cell describes any cell (including its progeny) that has been modified, transfected, transduced, transformed, and/or manipulated in any way to express an anti-CD38-CAR construct, as disclosed herein. Preferably, the host cell is a human T cell, placenta cell or NK cell.

The terms "transfected" or "transformed" or "transduced" refer to a process by which exogenous nucleic acid (e.g., transgene) is transferred or introduced into a host cell. A "transfected" or "transformed" or "transduced" host cell is one which has been transfected, transformed or transduced with exogenous nucleic acid. The host cell includes the primary subject cell and its progeny.

Transgenes, such as the disclosed nucleic acid sequences encoding anti-CD38 chimeric antigen receptors (CAR) constructs can be operably linked to a vector, including a viral vector, which is used as a vehicle to introduce a transgene into a host cell. Transgenes introduced (e.g., via transduction, transfection or transformation) into host cells can be transiently introduced or preferably stably integrated into the host cell's genome. Transgenes introduced into host cells can be propagated in progeny cells. Vectors can be single- or double-stranded DNA or RNA vectors. Vectors include expression vectors which direct expression of transgenes in a host cell. Suitable vectors include expression vectors which can contain an original of replication sequence, an inducible or constitutive promoter sequence, and at least one selectable marker sequence, where these sequences are functional in a packaging cell and/or host cell. Viral vectors used to introduce transgene into a host cell include vectors derived from the viral family Retroviridae which includes retroviral and lentiviral vectors. Retroviral vectors can be used to transduce dividing host cells, and lentiviral vectors can be used to transduce non-dividing host cells. Host cells transduced with the desired transgene linked to an expression vector include T cells, placental derived natural killer host cells, and cord blood derived natural killer host cells.

Retroviral vectors can be derived from any avian or mammalian source. Retroviral vectors can be capable of infecting host cells of several different species (e.g., amphotropic), including mice, rats and humans, or can have limited host range (e.g., ecotropic). Retroviral vectors can be derived from Moloney murine leukemia virus (MoMLV), myeloproliferative sarcoma virus (MPSV), murine embryonic stem cell virus (MESV), murine stem cell virus (MSCV), spleen focus forming virus (SFFV).

In a typical first generation retroviral transfer vector (e.g., gamma retroviral vector) system, sequences that encode retroviral gag, pol and env can be replaced with a desired transgene, and the transgene can be flanked on both sides by cis-acting long terminal repeat (LTR) sequences. The gag and pol sequences can be carried on a packaging plasmid, the env sequence can be carried separately on an envelope plasmid, and expression of these three viral sequences act in-trans. The transfer vector (containing the transgene) along with the packaging and envelope plasmids, are reacted with packaging cells in the presence of a transfection reagent to transduce the vector and plasmids into the packaging cells. The transduced packaging cells produce cell culture supernatant containing infectious virions harboring the transfer vector carrying the transgene. Transduced host cells are generated by reacting the host cells with the virion supernatant. Upon transduction the retroviral transfer vector (carrying the transgene) integrates into the host cell's genome (Morgan and Boyerinas 2016 *Biomedicines* 4(2):9 "Review: Genetic Modification of T Cells"). Retroviral transfer vectors can also contain a promoter that directs inducible or constitutive transcription of the transgene. A second generation retroviral vector system typically includes gag, pol and env sequence stably expressed in a packaging cell line which obviates the need for separate packaging and envelope plasmids. The packaging cell line is reacted with the packaging vector (carrying the transgene) to generate transduced packaging cells and virion supernatant. Phoenix helper-free retroviral packaging cell lines is an example of a second generation retroviral system. Retroviral vectors are used for host cell transduction (WO2014/055668).

Lentivirus vectors derived from HIV, SIV or FIV, can be used to introduce a transgene into a host cell. Several generations of lentivirus vectors have been developed. First generation lentiviral systems are similar to first generation retroviral systems in that they employ a transfer vector (carrying the transgene), packaging plasmid (carrying gag, pol, tat, rev and accessory sequences), and envelope plasmid (carrying a heterologous env sequence). Second generation lentiviral systems employ a transfer vector (transgene), packaging plasmid (gag, pol, tat and rev, and accessory sequences removed), and envelope plasmid (carrying a heterologous env sequence). Third generation lentiviral systems, sometimes called self-inactivating (SIN) systems, employ a transfer vector (transgene and 3' LTR having tat removed), a first packaging plasmid (gag and pol), a second packaging plasmid (rev), and envelope plasmid (carrying a heterologous env sequence). Similar to retroviral systems, any of these lentiviral systems involves reacting the vector/plasmids with packaging cells and a transduction reagent to produce cell culture supernatant containing virions which is in turn used to transduce host cells. Lentivirus vectors are used to transduce host cells (WO2012/031744; U.S. Pat. No. 8,802,374; and U.S. 2016/0152723).

Other viral vectors used to introduce transgenes into host cells include simian virus 40 (SV40), herpes simplex virus 1, adenovirus, adeno-associated virus (AAV) and Rous sarcoma virus (RSV) (Gross 1989 *Proc. Natl. Acad. Sci. USA* 86:10024-10028).

Expression vectors typically include a promoter and/or enhancer sequence that directs inducible or constitutive expression (e.g., transcription) in packaging cells and/or host cells to be introduced with a transgene. Constitutive promoters include retroviral LTR, immediate early cytomegalovirus (CMV) promoter, elongation growth factor 1 alpha (EF-1α), simian virus 40 (SV40) early promoter, mouse mammary tumor virus (MMTV) promoter, human immunodeficiency virus (HIV) long terminal repeat (LTR) promoter, Moloney murine leukemia virus (MoMuLV) promoter, avian leukemia virus promoter, Epstein-Barr virus immediate early promoter, Rous sarcoma virus promoter, PGK (phosphoglycerate kinase), UbC (Ubiquitin C), MLV (Moloney leukemia virus) and CAG (cytomegalovirus early enhancer element, promoter from first exon and intron of chicken beta-actin, and splice acceptor of rabbit beta-globin) enhancer sequence. Inducible promoter sequences include tetracycline operator (TetO) sites (Sakemura 2016 *Cancer Immunology Research* 4(8):658-668) and lac repressor system from *E. coli*. Promoters suitable for high expression from lentiviral vectors include human ubiquitin, MHC class I, MHC class II, and (32 microglobulin promoters (WO 2016/012623). Retroviral and lentiviral expression vectors are commercially-available from several sources including Applied Biological Materials (ABM) (Vancouver, Canada) and Addgene (Watertown, Mass.).

The term "target cells" are cells expressing one or more target polypeptides which renders them recognizable by an antibody or antibody derivative. In one embodiment, target cells include cancer target cells expressing CD38 polypeptides which are recognized for binding by chimeric antigen receptor (CAR) constructs of the present disclosure.

The term "about" or "approximately" means an acceptable error for a particular value as determined by one of ordinary skill in the art, which depends, in part, on how the value is measured or determined. For example, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

Anti-CD38 Chimeric Antigen Receptors (CARs)

The present disclosure describes a new CAR construct comprising a known anti-CD38 fully human antibody A2 (described in U.S. 2016/0297888 the disclosure of which is incorporated by reference herein) onto a second generation CAR construct scaffold and generally with different component transmembrane domains and intracellular domains. The compilation of the foregoing components into the disclosed CAR construct has produced a surprising result by avoiding "T cell fratricide" in an elegant manner. More specifically, the disclosed CD38-directed chimeric antigen receptors (CARs) can avoid self-lysis due to T cell display of CD38 targets. More specifically, the present disclosure provides, a nucleic acid sequence encoding an anti-CD38 CAR for transduction into T cells, cultured NK cells or placental-derived NK cells, wherein the CAR is directed by an antibody binding region of somewhat lower binding affinity. This lower binding affinity enables the disclosed CAR transduced host cell to avoid substantial lysis of T or NK cells having moderate or lower displays of surface CD38. Therefore, the disclosed CAR constructs with the disclosed targeting antibody achieve superior safety profiles and are able to be grown up without self-lysis as an improved characteristic CAR construct.

A CAR construct generally contains an extracellular region, e.g., a single chain variable fragment (scFv) of an antibody recognizing a tumor antigen (such as CD38), and an intracellular region, e.g., a T-cell receptor such as (TCR) zeta chain that mimics TCR activation and a signaling domain derived from CD28 or 4-ABB to mimic co-stimulation. CARs are generally constructed by joining the antigen recognition domains of an antibody with the signaling domains of receptors from T cells. Modification of T cells with nucleic acid sequences encoding CARs equips T cells with retargeted antibody-type antitumor cytotoxicity. Because killing is MHC-unrestricted, the approach offers a general therapy for all patients bearing the same antigen. These T cells engineered with CARs are often called "designer T cells", "CAR-T cells," or "T-bodies" (Eshhar et al. *Proc. Natl. Acad. Sci. USA* 90(2): 720-724,1993; Ma et al., *Cancer Chemother. Bio. l Response Modif.* 20: 315-341, 2002).

Specifically, the anti-CD38 A2 antibody heavy chain comprises amino acid sequence of SEQ ID NO: 1 and the light chain comprises amino acid sequence SEQ ID NO: 3. An anti-CD38 scFv A2 antibody comprises the amino acid sequence SEQ ID NO: 12.

Alternatively, the antigen binding region of the anti-CD38 CAR comprises an scFv comprising the CDR sequences corresponding to the light and heavy chain variable region of anti-CD38 antibody D8. The anti-CD38 D8 antibody heavy chain comprises amino acid sequence of SEQ ID NO: 2 and the light chain comprises amino acid sequence SEQ ID NO: 4. An anti-CD38 scFv comprises the amino acid sequence SEQ ID NO: 16.

The disclosed anti-CD38 CAR further comprises a hinge region, preferably a CD8 hinge region (SEQ ID NO: 6 or 17), or a functional fragment thereof. The disclosed the anti-CD38 CAR further comprises an extracellular domain, preferably a CD28 extracellular domain (SEQ ID NO: 7), or a functional fragment thereof. The disclosed anti-CD38 CAR further comprises a transmembrane domain, preferably a transmembrane domain from the transmembrane domains of the protein selected from the group consisting of alpha chain of T-cell receptor, beta chain of T-cell receptor, zeta chain of T-cell receptor, CD28, CD3 epsilon, CD45, CD4, CD5, CD8, CD9, CD16, CD22, CD33, CD37, CD64, CD80, CD86, CD134, CD137, CD154, LFA-1 T-cell co-receptor, CD2 T-cell co-receptor/adhesion molecule, CD8 alpha, and combinations thereof. Preferably, the transmembrane domain is from CD28 transmembrane domain (SEQ ID NO: 8), or a functional fragment thereof.

The disclosed anti-CD38 CAR further comprises an intracellular signaling domain comprising signaling domains from the group consisting of a CD3-zeta chain, 4-1BB, CD28, and combination thereof. If there are two signaling domains, the second one is called a co-stimulatory signaling domain. Preferably, the co-stimulatory signaling domain comprises an intracellular domain, or fragment thereof, of, but not limited to, the following proteins: CD27, CD28, 4-1BB, OX40, CD30, CD40, PD-1, ICOS, lymphocyte function-associated antigen-1 (LFA-1), CD2, CD7, LIGHT, NKG2C, B7-H3, a CD83 ligand, and any combination thereof. In some embodiments, the intracellular signaling domain comprises a CD28 signaling domain. In further embodiments, the CD28 signaling domain comprises the amino acid sequence of SEQ ID NO: 9, or a functional fragment thereof. In some embodiments, the intracellular signaling domain comprises a CD3-ξ signaling domain. In further embodiments, the CD3-ξ signaling domain comprises the amino acid sequence of SEQ ID NO: 10, or a functional fragment thereof.

Thus, the present disclosure encompasses isolated nucleic acid molecules comprising sequences encoding the disclosed anti-CD38 CAR construct. It should be noted that where an amino acid sequence is described, also included is a nucleic acid sequence that encodes the amino acid sequence.

1. Extracellular Anti-CD38 Binding Protein

The present disclosure provides an anti-CD38 CAR comprising an antigen binding protein that binds to CD38, wherein the antigen binding protein comprises a heavy chain variable (VH) domain comprising an amino acid sequence that is at least 95% identical to the amino acid sequence of SEQ ID NO: 1. Preferably, the VH domain comprises an amino acid sequence that is at least 96% homologous to the amino acid sequence of SEQ ID NO: 1, or the VH domain comprises an amino acid sequence that is at least 97% identical to the amino acid sequence of SEQ ID NO: 1, or the VH domain comprises an amino acid sequence that is at least 98% identical to the amino acid sequence of SEQ ID NO: 1, or the VH domain comprises an amino acid sequence that is at least 99% identical to the amino acid sequence of SEQ ID NO: 1.

Further, the present disclosure provides a CAR comprising an antigen binding protein that binds to CD38, wherein the antigen binding protein comprises a light chain variable (VL) domain comprising an amino acid sequence that is at least 95% identical to the amino acid sequence of SEQ ID NO: 3, or VL domain comprises an amino acid sequence that is at least 96% identical to the amino acid sequence of SEQ ID NO: 3, or the VL domain comprises an amino acid sequence that is at least 97% identical to the amino acid sequence of SEQ ID NO: 3, or the VL domain comprises an amino acid sequence that is at least 98% identical to the amino acid sequence of SEQ ID NO: 3, or the VL domain comprises an amino acid sequence that is at least 99% identical to the amino acid sequence of SEQ ID NO: 3.

Preferably, the disclosed anti-CD38 CAR comprises an scFv, comprising a light chain having a variable domain comprising an amino acid sequence of SEQ ID NO: 3; and a heavy chain having a variable domain comprising an amino acid sequence of SEQ ID NO: 1.

The present disclosure provides an anti-CD38 CAR comprising an antigen binding protein that binds to CD38, wherein the antigen binding protein comprises a heavy chain variable (VH) domain comprising an amino acid sequence that is at least 95% identical to the amino acid sequence of SEQ ID NO: 2. Preferably, the VH domain comprises an amino acid sequence that is at least 96% homologous to the amino acid sequence of SEQ ID NO: 2, or the VH domain comprises an amino acid sequence that is at least 97% identical to the amino acid sequence of SEQ ID NO: 2, or the VH domain comprises an amino acid sequence that is at least 98% identical to the amino acid sequence of SEQ ID NO: 2, or the VH domain comprises an amino acid sequence that is at least 99% identical to the amino acid sequence of SEQ ID NO: 2.

Further, the present disclosure provides a CAR comprising an antigen binding protein that binds to CD38, wherein the antigen binding protein comprises a light chain variable (VL) domain comprising an amino acid sequence that is at least 95% identical to the amino acid sequence of SEQ ID NO: 4, or VL domain comprises an amino acid sequence that is at least 96% identical to the amino acid sequence of SEQ ID NO: 4, or the VL domain comprises an amino acid sequence that is at least 97% identical to the amino acid sequence of SEQ ID NO: 4, or the VL domain comprises an amino acid sequence that is at least 98% identical to the amino acid sequence of SEQ ID NO: 4, or the VL domain comprises an amino acid sequence that is at least 99% identical to the amino acid sequence of SEQ ID NO: 4.

The present disclosure provides anti-CD38 chimeric antigen receptor (CAR) constructs having one or more variations, including amino acid substitutions, deletions and/or insertions, compared to the amino acid sequence of the CAR constructs described herein, so long as the variant CAR constructs comprise an amino acid sequence that is at least 95% identical to SEQ ID NO: 20 or 21.

Preferably, the disclosed anti-CD38 CAR comprises an scFv, comprising a light chain having a variable domain comprising an amino acid sequence of SEQ ID NO: 4; and a heavy chain having a variable domain comprising an amino acid sequence of SEQ ID NO: 2.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides (VL and VH). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different VL- and VH-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879; Ward et al., 1989, *Nature* 334:544, and de Graaf et al., 2002, *Methods Mol. Biol.* 178:379-87.

2. Transmembrane Domains

A transmembrane domain of the disclosed anti-CD38 CAR construct describes any polypeptide structure that is thermodynamically stable in a cell membrane, preferably a mammalian cell membrane. Transmembrane domains compatible for use in the disclosed anti-CD38 CAR construct may be obtained from any natural transmembrane protein, or a fragment thereof. Alternatively, the transmembrane domain can be a synthetic, non-naturally occurring transmembrane protein, or a fragment thereof, e.g., a hydrophobic protein segment that is thermodynamically stable in a cell membrane (e.g., a mammalian cell membrane).

Preferably, the transmembrane domain used in a CAR is derived from a membrane protein selected from the group consisting of CD8α, CD8β, 4-1BB/CD137, CD28, CD34, CD4, FcϵRIγ, CD16, OX40/CD134, CD3ξ, CD3ε, CD3γ, CD3δ, TCRα, TCRβ, TCRξ, CD32, CD64, CD64, CD45, CD5, CD9, CD22, CD33, CD37, CD64, CD80, CD86, CD137, CD154, LFA-1 T cell co-receptor, CD2 T cell co-receptor/adhesion molecule, CD40, CD4OL/CD154, VEGFR2, FAS, and FGFR2B. Preferably, the transmembrane domain is derived from CD8α, 4-1BB/CD137, CD28 or CD34.

Preferably the transmembrane domain of an anti-CD38 CAR comprises an amino acid sequence that is at least 95% identical to the amino acid sequence of SEQ ID NO: 8, or the transmembrane domain comprises an amino acid sequence that is at least 96% identical to the amino acid sequence of SEQ ID NO: 8, or the transmembrane domain comprises an amino acid sequence that is at least 97% identical to the amino acid sequence of SEQ ID NO: 8, or the transmembrane domain comprises an amino acid sequence that is at least 98% identical to the amino acid sequence of SEQ ID NO: 8, or the transmembrane domain comprises an amino acid sequence that is at least 99% identical to the amino acid sequence of SEQ ID NO: 8.

3. Intracellular Domains

The anti-CD38 CARs disclosed herein comprise an intracellular signaling domain. A signaling domain is generally responsible for activation of at least one of the normal effector functions of a cell. The term "effector function" describes a specialized function of a cell. For example, the effector function of a T cell or an NK cell includes a cytolytic activity or helper activity. "Signaling domain" describes the portion of a protein which transduces the effector function signal and directs the cell to perform its specialized function. While usually the entire intracellular signaling domain can be employed, in many cases it is not necessary to use an entire chain or domain. To the extent that a truncated portion of the intracellular signaling domain is used, such truncated portion may be used in place of the intact domain as long as it transduces the effector function signal.

A primary signaling domain regulates primary activation of the TCR complex either in a stimulatory way, or in an inhibitory way. Primary signaling domains that act in a stimulatory manner may contain signaling motifs which are known as immunoreceptor tyrosine-based activation motifs (ITAMs). Primary signaling domains containing ITAMs for use in the anti-CD38 CARs include the signaling domains of TCR zeta, FcR gamma, FcR beta, CD3 gamma, CD3 delta, CD3 epsilon, CD5, CD22, CD79a, CD79b, and CD66d. Preferably, a primary signaling domain is CD3ξ or CD28.

Preferably the primary signaling domain of the anti-CD38 CAR comprises an amino acid sequence that is at least 95% identical to the amino acid sequence of SEQ ID NO: 9, or the primary signaling domain comprises an amino acid sequence that is at least 96% identical to the amino acid sequence of SEQ ID NO: 9, or the primary signaling domain comprises an amino acid sequence that is at least 97% identical to the amino acid sequence of SEQ ID NO: 9, or the primary signaling domain comprises an amino acid sequence that is at least 98% identical to the amino acid sequence of SEQ ID NO: 9, or the primary signaling domain comprises an amino acid sequence that is at least 99% identical to the amino acid sequence of SEQ ID NO: 9.

Preferably the primary signaling domain of the anti-CD38 CAR comprises an amino acid sequence that is at least 95% identical to the amino acid sequence of SEQ ID NO: 10, or the primary signaling domain comprises an amino acid sequence that is at least 96% identical to the amino acid sequence of SEQ ID NO: 10, or the primary signaling domain comprises an amino acid sequence that is at least 97% identical to the amino acid sequence of SEQ ID NO: 10, or the primary signaling domain comprises an amino acid sequence that is at least 98% identical to the amino acid sequence of SEQ ID NO: 10, or the primary signaling domain comprises an amino acid sequence that is at least 99% identical to the amino acid sequence of SEQ ID NO: 10.

Moreover, the disclosed anti-CD38 CAR constructs further comprise a co-stimulatory signaling domain. Examples of co-stimulatory signaling domains for use in the chimeric receptors are cytoplasmic signaling domain of co-stimulatory proteins selected from the group consisting of members of the B7/CD28 family (B7-1/CD80, B7-2/CD86, B7-H1/PD-L1, B7-H2, B7-H3, B7-H4, B7-H6, B7-H7, BTLA/CD272, CD28, CTLA-4, Gi24/VISTA/B7-H5, ICOS/CD278, PD-1, PD-L2/B7-DC, and PDCD6); members of the TNF superfamily (4-1BB/TNFSF9/CD137, 4-1BB ligand/TNFSF9, BAFF/BLyS/TNFSF13B, BAFF R/TNFRSF13C, CD27/TNFRSF7, CD27 ligand/TNFSF7, CD30/TNFRSF8, CD30 ligand/TNFSF8, CD40/TNFRSF5, CD40/TNFSF5, CD40 ligand/TNFSF5, DR3/TNFRSF25, GITR/TNFRSF18, GITR ligand/TNFSF18, HVEM/TNFRSF14, LIGHT/TNFSF14, lymphotoxin-alpha/TNF-beta, OX40/TNFRSF4, OX40 ligand/TNFSF4, RELT/TNFRSF19L, TACI/TNFRSF13B, TL1A/TNFSF15, TNF-α, and TNF RII/TNFRSF1B); members of the interleukin-1 receptor/toll-like receptor (TLR) superfamily (TLR1, TLR2, TLR3, TLR4, TLR5, TLR6, TLR7, TLR8, TLR9, and TLR10); members of the SLAM family (2B4/CD244/SLAMF4, BLAME/SLAMF8, CD2, CD2F-10/SLAMF9, CD48/SLAMF2, CD58/LFA-3, CD84/SLAMF5, CD229/SLAMF3, CRACC/SLAMF7, NTB-A/SLAMF6, and SLAM/CD150); CD2, CD7, CD53, CD82/Kai-1, CD90/Thy1, CD96, CD160, CD200, CD300a/LMIR1, HLA Class I, HLA-DR, ikaros, integrin alpha 4/CD49d, integrin alpha 4 beta 1, integrin alpha 4 beta 7/LPAM-1, LAG-3, TCL1A, TCL1B, CRTAM, DAP10, DAP12, MYD88, TRIF, TIRAP, TRAF, Dectin-1/CLEC7A, DPPIV/CD26, EphB6, TIM-1/KIM-1/HAVCR, TIM-4, TSLP, TSLP R, lymphocyte function associated antigen-1 (LFA-1), and NKG2C. Preferably, the co-stimulatory domain comprises an intracellular domain of an activating receptor protein selected from the group consisting of α$_4$β$_1$ integrin, β$_2$ integrins (CD11a-CD18, CD11b-CD18, CD11b-CD18), CD226, CRTAM, CD27, NKp46, CD16, NKp30, NKp44, NKp80, NKG2D, KIR-S, CD100, CD94/NKG2C, CD94/NKG2E, NKG2D, PENS, CEACAM1, BY55, CRACC, Ly9, CD84, NTBA, 2B4, SAP, DAP10, DAP12, EAT2, FcRγ, CD3ξ, and ERT. Preferably, the co-stimulatory domain comprises an intracellular domain of an inhibitory receptor protein selected from the group consisting of KIR-L, LILRB1, CD94/NKG2A, KLRG-1, NKR-P1A, TIGIT, CEACAM, SIGLEC 3, SIGLEC 7, SIGLEC9, and LAIR-1. Preferably, the co-stimulatory domain comprises an intracellular domain of a protein selected from the group consisting of CD27, CD28, 4-1BB (CD137), OX40, CD30, CD40, PD1, ICOS, lymphocyte function-associated antigen-1 (LFA-1), CD2, CD7, LIGHT, NKG2C, B7-H3, and a ligand that specifically binds with CD83.

4. Hinge Regions

The anti-CD38 CAR further comprises a hinge region. The hinge region is located between the scFv antibody region and the transmembrane domain. A hinge region is an amino acid segment that is generally found between two domains of a protein and allows for flexibility of the anti-CD38 CAR and movement of one or both of the domains relative to one another. Preferably, the hinge region comprises from about 10 to about 100 amino acids, e.g., from about 15 to about 75 amino acids, from about 20 to about 50 amino acids, or from about 30 to about 60 amino acids. Or the hinge region is a hinge region of a naturally-occurring protein. Preferably, the hinge region is a CD8a hinge region selected from the group consisting of CD8 hinge region and CD8α hinge region. Preferably, the hinge region is disposed between the C-terminus of the scFv and the N-terminus of the transmembrane domain of the CAR.

Preferably the hinge region of the anti-CD38 CAR comprises an amino acid sequence that is at least 95% identical to the amino acid sequence of SEQ ID NO: 6, or the hinge region comprises an amino acid sequence that is at least 96% identical to the amino acid sequence of SEQ ID NO: 6, or the hinge region comprises an amino acid sequence that is at least 97% identical to the amino acid sequence of SEQ ID NO: 6, or the hinge region comprises an amino acid sequence that is at least 98% identical to the amino acid sequence of SEQ ID NO: 6, or the hinge region comprises an amino acid sequence that is at least 99% identical to the amino acid sequence of SEQ ID NO: 6.

Preferably the hinge region of the anti-CD38 CAR comprises an amino acid sequence that is at least 95% identical to the amino acid sequence of SEQ ID NO: 17, or the hinge region comprises an amino acid sequence that is at least 96% identical to the amino acid sequence of SEQ ID NO: 17, or the hinge region comprises an amino acid sequence that is at least 97% identical to the amino acid sequence of SEQ ID NO: 17, or the hinge region comprises an amino acid sequence that is at least 98% identical to the amino acid sequence of SEQ ID NO: 17, or the hinge region comprises an amino acid sequence that is at least 99% identical to the amino acid sequence of SEQ ID NO: 17.

5. Signal Peptides

Signal sequences are peptide sequences that target a polypeptide to the desired site in a cell, such as the secretory pathway of the cell and will allow for integration and anchoring of the anti-CD38 CAR into the lipid bilayer of the cellular membrane. Preferably, the signal is the signal sequence of from the group consisting of CD8α, CD28, and CD16.

Preferably the signal sequence of the anti-CD38 CAR comprises an amino acid sequence that is at least 95% identical to the amino acid sequence of SEQ ID NO: 19, or the signal sequence comprises an amino acid sequence that is at least 96% identical to the amino acid sequence of SEQ ID NO: 19, or the signal sequence comprises an amino acid sequence that is at least 97% identical to the amino acid sequence of SEQ ID NO: 19, or the signal sequence comprises an amino acid sequence that is at least 98% identical to the amino acid sequence of SEQ ID NO: 19, or the signal sequence comprises an amino acid sequence that is at least 99% identical to the amino acid sequence of SEQ ID NO: 19.

Host Cells

Isolated host cells or populations of host cells are transduced with the disclosed anti-CD38 construct to express the anti-CD38 CAR. There are two distinct groups of host cells. The first group are patient derived isolated T cell, also called autologous T cells. Such populations of autologous T cells are obtained from a patient, isolated and expanded. Then the expanded T cells are transduced with the disclosed anti-CD38 CAR construct to achieve as high a population as possible of transduced T cells that are expanded and returned (administered) to the individual patient. The disclosed anti-CD38 CAR construct was able to achieve cell lysis only with high CD38 expressing tumor cells, mostly multiple myeloma (MM) tumor cells.

The second group of host cells are cultured T or NK cells of fetal origin, preferably derived from placenta or chord tissue after pregnancy. This second group of host cells are not autologous but cultured and used universally across all human patients.

The present disclosure provides CAR constructs which can transduce T cells, cultured NK cells or placental-derived NK cells and are able to avoid lysis of T or NK cells having moderate or lower displays of surface CD38.

Therapeutic Methods and Uses of Anti-CD38 CARs

The present disclosure provides methods for treating a cancer or inhibiting tumor growth in a subject in need thereof, the method comprising administering to the subject an isolated host cell comprising an anti-CD38 CAR, or a population of transduced host cells. Hematologic cancer can be treated using the anti-CD38 CARs disclosed herein. Examples of hematologic cancer that can be treated using the methods of the disclosure include non-Hodgkin's lymphoma (NHL), Burkitt's lymphoma (BL), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML). Preferably, the hematologic cancer is multiple myeloma (MM).

Multiple myeloma (MM) is a malignancy of plasma cells and is the second most common hematological cancer worldwide. Currently there is no cure for this disease and its five-year survival rate is only 45%. Over the past decade, there have been significant advances in treating MM, including novel immunomodulatory agents, proteasome inhibitors, and autologous hematopoietic stem cell transplantation (Kumar et al. Blood 111(5): 2516-2520, 2008; Barosi, et al. *Ann. Hematol.* 91(6): 875-888, 2012; Kharfan-Dabaja et al. *J. Hematol. Oncol.* 6: 2, 2013).

The disclosure provides a method of inhibiting growth of a tumor expressing a cancer associated antigen, comprising contacting a cancer cell of the tumor with a transduced host cell comprising an anti-CD38 CAR, or a population of transduced host cells, wherein the host cell is an NK cell, such as placental NK cell.

The transduced host cells may be administered at a dosage of about $10^1$ to about $10^9$ cells/kg body weight. Ranges intermediate to the above recited dosage, e.g., about $10^2$ to about $10^8$ cells/kg body weight, about $10^4$ to about $10^7$ cells/kg body weight, about $10^5$ to about $10^6$ cells/kg body weight, are also intended to be part of this disclosure.

The transduced host cells may be administered daily or preferably less frequently.

Construction of Retroviral Vector Expressing Anti-CD38 A2 CAR

The 2nd generation anti-CD38 A2 CAR was generated by using a human anti-CD38 antibody screened from a proprietary human single chain variable region (scFv) antibody library. A 10-amino acid myc tag (Amino acids: EQKLISEEDL (SEQ ID NO: 12), DNA: GAGCAGAAGCTTATCTCCGAGGAAGATCTG (SEQ ID NO: 22)) from the human cmyc gene was added to the N-terminal region of the scFv for detection of the CAR expression.

This disclosed constructed anti-CD38 CAR, is named "Anti-CD38 A2 CAR." It is a 2nd generation IgCD28TCR CAR that comprises 542 amino acid residues, including 19 amino acid residues of signal peptide from mouse antibody heavy chain followed by 2 additional amino acid residues Asp and Ile, 10 amino acid residues of human myc tag, 118 amino acid residues of VH of the anti-CD38 antibody, 15 amino acid residues of linker in the form of ((G4)S)3, 110 amino acid residues of VL of anti-CD38 antibody, 46 amino acid residues of CD8α hinge, 40 amino acid residues of CD28 extracellular domain (serving as a spacer), 27 amino acid residues of CD28 transmembrane domain, 41 amino acid residues of CD28 intracellular signaling domain, and 112 amino acid residues of TCR intracellular domain (FIG. 1). The mature disclosed Anti-CD38 A2 CAR comprises 523 amino acid residues with a predicated monomeric protein weight of ~57 kDa.

Anti-CD38 A2 CAR-T cells were generated by transduction of anti-CD3 antibody (OKT3) (Miltenyi Biotech) activated T cells with the Anti-CD38 CAR expressing retroviral vector (FIG. 2A). When analyzed by Western blotting, the Anti-CD38 CAR migrated at the molecular weight of ~70 kD under reducing condition and ~140 kD under non-reducing condition (FIG. 2B), confirming homodimer formation on T cell surface. The slower migrating bands may represent glycosylated forms of the molecule. The CAR2-AntiCD38A2 CAR was detected as monomer with molecular weight of ~70 kDa under reducing conditions and homodimer with molecular weight of 140 kDa in non-reducing conditions. These results suggest that CAR2-AntiCD38A2 CAR forms homodimers on the CAR-T cell surface.

Figure 3:
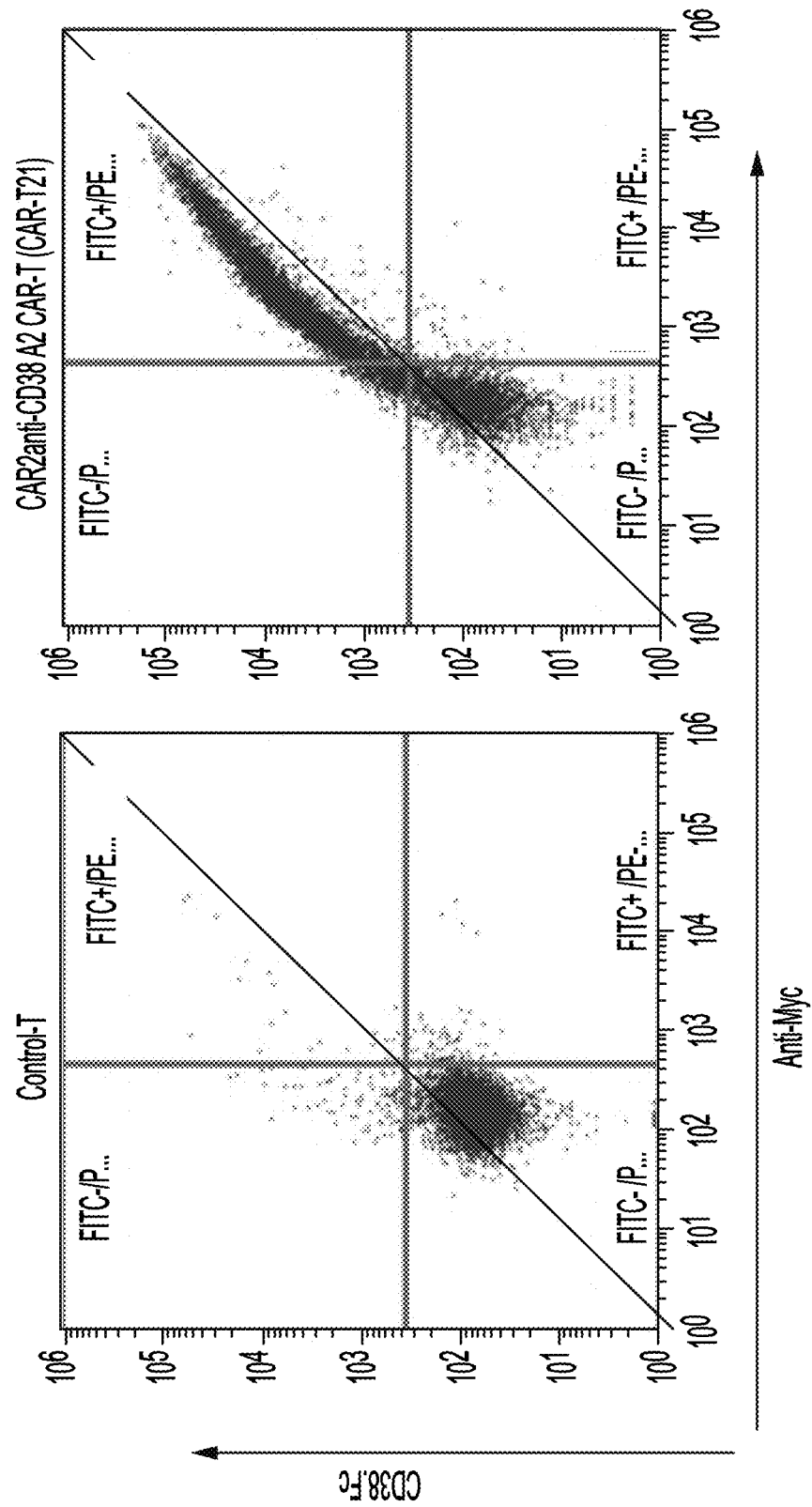
FIG. 3 shows binding data. Non-transduced control and AntiCD38 A2 CAR transduced T cells were incubated with 2 µg/ml CD38-Fc fusion protein and analyzed by flow cytometry with PE-conjugated goat anti-human IgG to detect CD38-Fc binding, and FITC-conjugated goat anti-Myc antibody to detect CAR expression on the T cells. These data confirm that Anti-CD38 A2 CAR T cells can bind their targeted antigen CD38.

When incubated with CD38-Fc fusion protein, the Anti-CD38 A2 CAR-T cells displayed strong CD38 binding activity that was correlated with the CAR expression (FIGS. 3A and 3B). These results confirm that the anti-CD38 A2 CAR-T cells can specifically and efficiently bind with CD38 through the expressed CARs. To confirm that Anti-CD38 A2 CAR T cells can bind their targeted antigen CD38, non-transduced control and AntiCD38 A2 CAR transduced T cells were incubated with 2 µg/ml CD38-Fc fusion protein and analyzed by flow cytometry with PE-conjugated goat anti-human IgG to detect CD38-Fc binding, and FITC-conjugated goat anti-Myc antibody to detect CAR expression on the T cells (FIG. 3).

Anti-CD38 A2 CAR-T Cells selectively kill CD38 upregulated cells. CD38 was found to be expressed on activated T cells and considered as a T cell activation marker (Deaglio et al., *J. Immunol.* 160(1):395-402, 1998 and Sandoval-Montes and Santos-Argumedo, *J. Leukocyte Biol.* 77(4): 513-521, 2005). We examined the CD38-expressing populations in anti-CD38 CAR-T cells and found that only the CD38 upregulated population was eliminated in the Anti-CD38 CAR-T cells (FIG. 3). The remaining CD38 negative and low expression CAR-T cell populations were stable with viability comparable to the control T cells during long-term cell culture. This characteristic of Anti-CD38 CAR-T cells allows the CAR-T cells to survive well in culture, avoid self-lysis and provide a clinical advantage for limited on-target/off-tumor side effects pertaining to CAR-T cells, as the anti-CD38 CAR-T cells will selectively kill CD38 upregulated MM cells but not CD38 normal expression cells.

Figure 4:
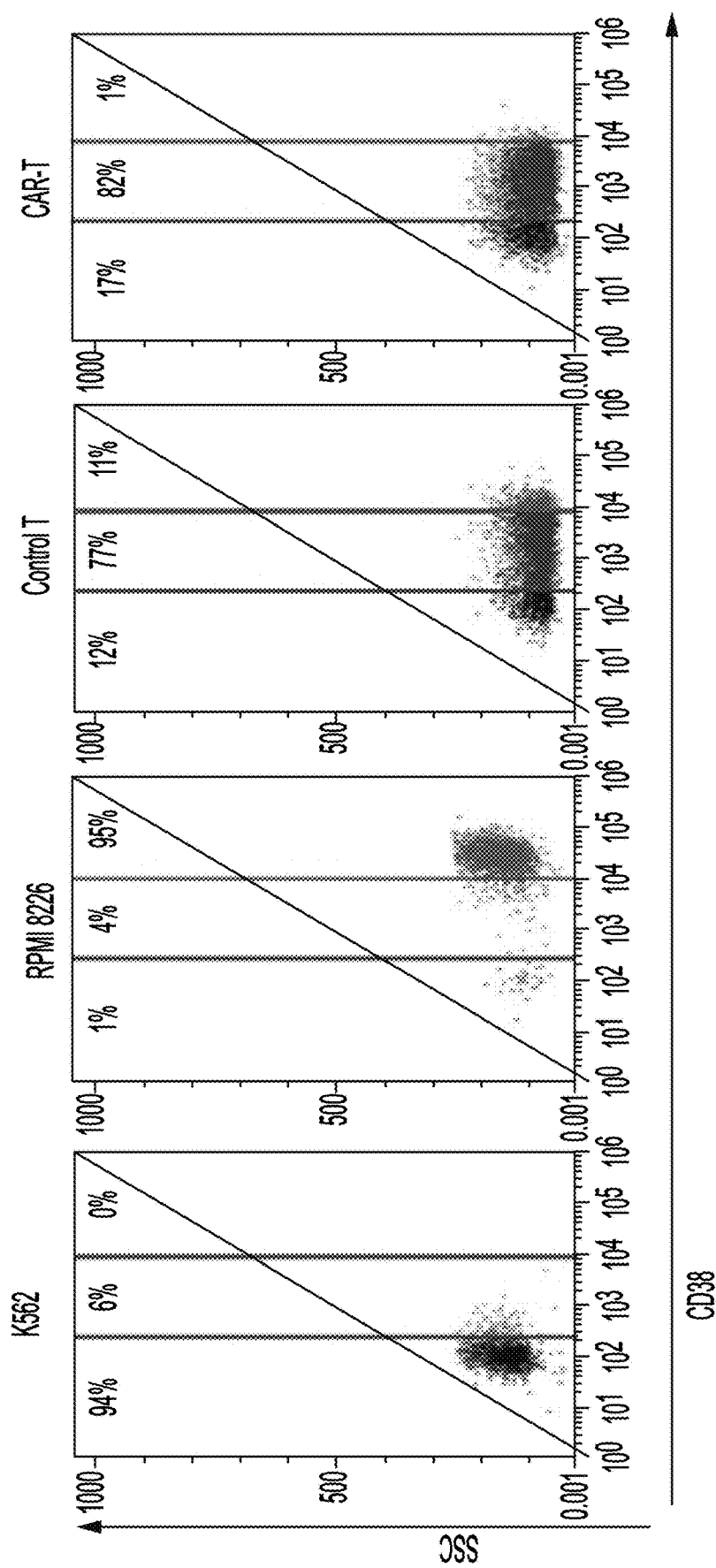
FIG. 4 shows relative CD38 expression on various cell types. Non-transduced control and Anti-CD38 A2 CAR transduced T cells were analyzed by flow cytometry staining with mouse anti-human CD38 mAb followed by staining with APC-conjugated goat anti-mouse IgG antibody. The CD38 expression on anti-CD38 CAR-T cells was assessed to investigate the anti-CD38 A2 CAR-T fratricide activity (shown in FIG. 5).

To investigate the anti-CD38 A2 CAR-T fratricide activity, the CD38 expression on anti-CD38 CAR-T cells was assessed (FIG. 4). Non-transduced control and Anti-CD38 A2 CAR transduced T cells were analyzed by flow cytometry staining with mouse anti-human CD38 mAb followed by staining with APC-conjugated goat anti-mouse IgG antibody.

The ability to avoid fratricide was shown by stability and viability of the disclosed anti-CD38 CAR cells having the A2 antibody in long term cell culture. Non-transduced control and Anti-CD38 A2 CAR transduced T cells were analyzed on day 15 after transduction by flow cytometry for (FIG. 5A) stability of CAR-T cells by staining with PE-conjugated anti-myc antibody and (FIG. 5B) viability of T cells by gating viable cells with forward scatter (FSC) and side scatter (SSC). After 15 days of culture, the percentage of CAR-positive cells among the transduced T cells declined only slightly from 74% on day 4 (FIG. 5A) after transduction to 65% on day 15, and the viability was comparable to the control T cells (85% versus 91%). Similar results were obtained from other donors.

Figure 6:
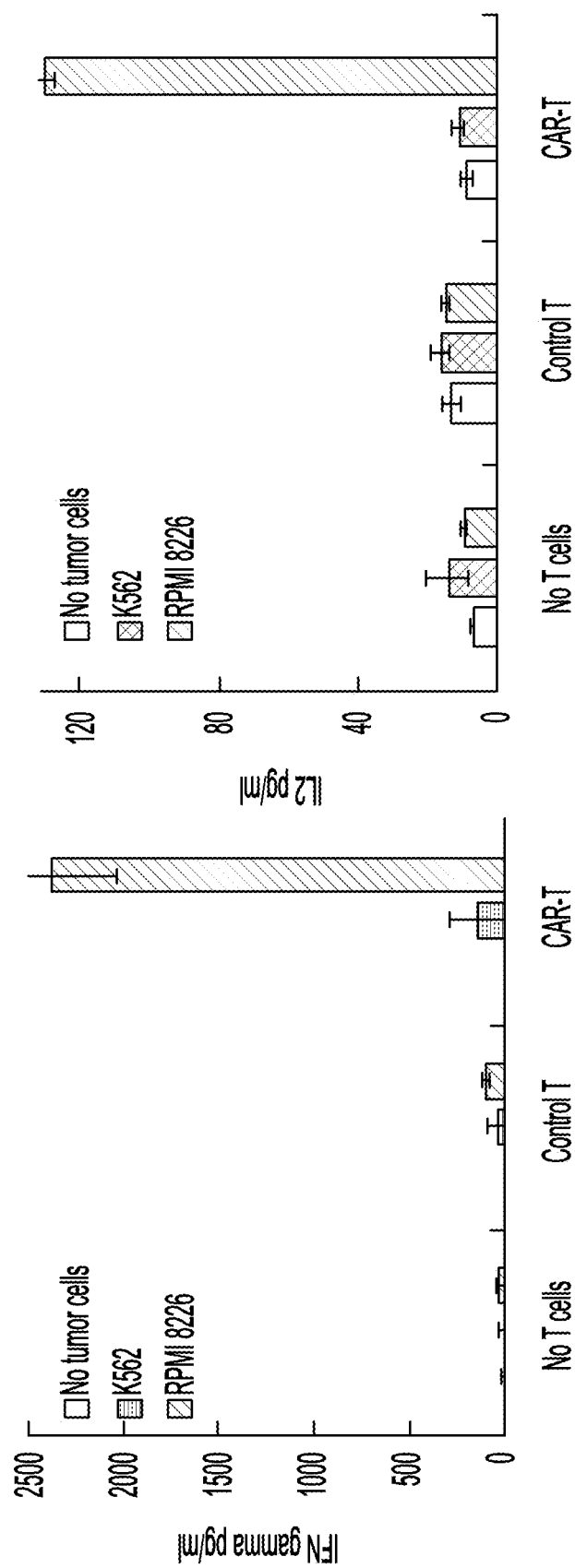
FIG. 6 shows cytokine production from Anti-CD38 CAR A2 transduced T cells. Non-transduced control T cells and Anti-CD38 CAR A2 transduced T cells were incubated with control CD38-negative K562 cells (Control T), or with CD38-expressing RPMI 8226 tumor cells (CAR-T) for 24 hours. The bars depicted in the histograms represent (from left to right) No tumor cells, K562 or RPMI 8226 cells. Supernatants were harvested and assayed for IFNγ (FIG. 6, left) and IL2 (FIG. 6, right) production by ELISA. Upon engaging with their targeted CD38-positive MM tumor cell RMPI8622, but not the CD38-negative control tumor cell K562, Anti-CD38 A2 CAR-T cells produced large amounts of cytokines IFNγ and IL2, indicating that the Anti-CD38 A2 CAR-T cells can be specifically activated upon targeted tumor cell engagement.

To test whether anti-CD38 A2 CAR-T cells could be activated by CD38-expressing tumor cells for cytokine production, non-transduced control T cells and Anti-CD38 A2 CAR transduced T cells were incubated with control CD38-negative K562 cells (Control T), or with CD38expressing RPMI 8226 tumor cells (CAR-T) for 24 hours. Upon engaging with their targeted CD38-positive MM tumor cell RMPI8622, but not the CD38-negative control tumor cell K562, Anti-CD38 A2 CAR-T cells produced large amounts of cytokines IFNγ and IL2, indicating that the Anti-CD38 A2 CAR-T cells can be specifically activated upon targeted tumor cell engagement (FIG. 6). Non-transduced control T cells and Anti-CD38 CAR A2 transduced T cells were incubated with control CD38negative K562 cells (Control T), or with CD38-expressing RPMI 8226 tumor cells (CAR-T) for 24 hours. Supernatants were harvested and assayed for IFNγ and IL2 production by ELISA.

Figure 7:
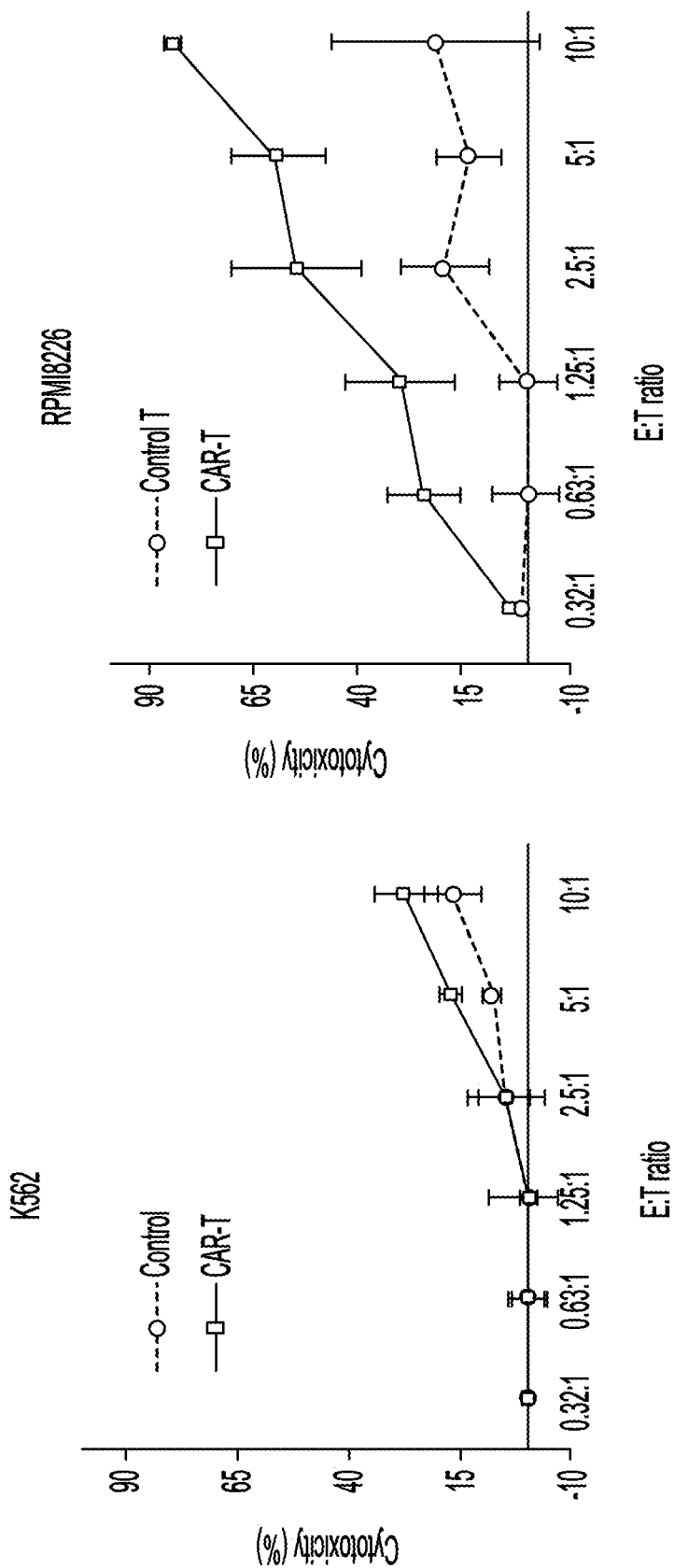
FIG. 7 shows cytotoxicity data from Anti-CD38 CAR A2 transduced T cells. Non-transduced control and AntiCD38 A2 CAR transduced T cells (E) were incubated with fluorescence enhancing ligand-labelled CD38-negative K562 (FIG. 7, left) or CD38-expressing RPMI8226 (FIG. 7, right) tumor cells (T) for 2 hours at the indicated ratio, and processed and analyzed by DELFIA cytotoxicity assay. These data show CD38-specific cytotoxicity of the disclosed anti-CD38 A2 CAR-T cells.

An important functional criterion for CAR-T cells is their ability to specifically kill target antigen-expressing tumor cells. To confirm that the CD38-specific cytotoxicity of Anti-CD38 A2 CAR-T cells, cytotoxicity assays were performed. Non-transduced control and CAR transduced T cells (E) were incubated with CD38-negative K562 or CD38-expressing RPMI8226 tumor cells (T) for 2 hours. There was no cytotoxicity of both the non-transduced control T and transduced CAR-T cells for CD38-negative K562 tumor cells (FIG. 7, left). In contrast, the Anti-CD38 A2 CAR-T cells, but not the non-transduced control T cells, effectively lysed the CD38 expressing RPMI8226 MM tumor cells in a cell-dose dependent manner (FIG. 7 right). These results confirm that the cytolytic activity of Anti-CD38 CAR-T cells was highly potent and specific for CD38-expressing MM tumor cells. FIG. 7 shows non-transduced control and AntiCD38 A2 CAR transduced T cells (E) were incubated with fluorescence enhancing ligand-labelled CD38-negative K562 or CD38-expressing RPMI8226 tumor cells (T) for 2 hours at the indicated ratio, and processed and analyzed by DELFIA cytotoxicity assay. These data show the CD38-specific cytotoxicity of the anti-CD38 A2 CAR-T cells.

Figure 8:
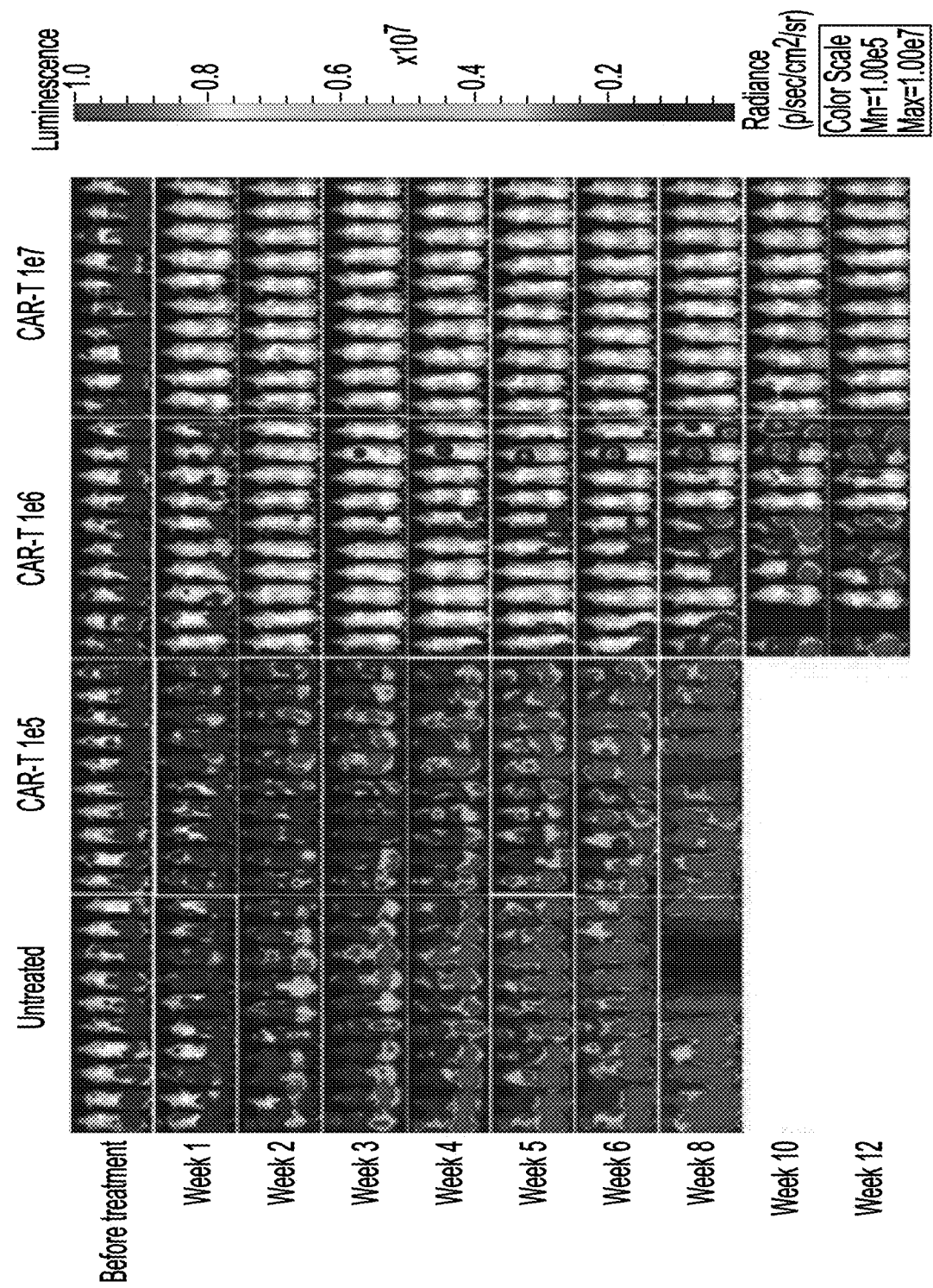
FIG. 8 shows tumoricidal activity of the Anti-CD38 A2 CAR-T cells assessed in a xenograft animal model. Immunocompromised NSG mice were inoculated intravenously with $1 \times 10^7$ Luc-GFP labelled CD38-expressing RPMI8226 MM tumor cells. 3 weeks later, the IVIS measurable systemic tumor formed in all inoculated mice. Mice were intravenously treated with different doses of Anti-CD38 A2 CAR-T cells, untreated mice served as a control. Tumor burden was assessed weekly by bioluminescent imaging (IVIS). In conclusion, these data demonstrate that the Anti-CD38 A2 CAR-T cells exhibit an antibody-type specificity that can recognize CD38 high expression cells in an MHC-nonrestricted fashion, resulting in T-cell activation, target cell lysis in vitro and eradication of MM tumor in vivo.

FIG. 8 shows tumoricidal activity of the Anti-CD38 A2 CAR-T cells assessed in a xenograft animal model. Immunocompromised NSG mice were inoculated intravenously with $1\times10^7$ Luc-GFP labelled CD38-expressing RPMI8226 MM tumor cells. 3 weeks later, the IVIS measurable systemic tumor formed in all inoculated mice. Mice were intravenously treated with different dose of Anti-CD38 A2 CAR-T cells, untreated mice were served as a control. Tumor burden was assessed weekly by bioluminescent imaging (IVIS). In conclusion, these data demonstrate that the Anti-CD38 A2 CAR-T cells exhibit an antibody-type specificity that can recognize CD38 high expression cells in a MHC-nonrestricted fashion, resulting in T-cell activation, target cell lysis in vitro and eradication of MM tumor in vivo. This in vivo study determined dose-dependent eradication of CD38-expressing MM Tumors by Anti-CD38 A2 CAR-T Cells. The objective of this study is to develop CD38-specific CAR-T cells in different doses for adoptive immunotherapy of CD38 high expression MM. Tumoricidal activity of the Anti-CD38 A2 CAR-T cells in a xenograft animal model was tested to mimic the potential therapeutic application of the dose-dependent anti-CD38 A2 CAR-T cells in CD38 upregulated MM patients. Anti-CD38 A2 CAR-T cells were administrated intravenously with different doses to immunodeficient NSG mice with established systemic xenograft human RPMI8226 MM tumors. FIG. 8 depicts the results of this experiment. One week after CAR-T cells treatment, all the established RPMI8226 MM tumors were eradicated from the treated mice at $1\times10^7$ of CAR-T cells, all ten mice were rendered free of tumor at 12 weeks (current). At $1\times10^6$ of CAR-T cells, the average tumor burden was reduced 85% (data on file) one week after CAR-T cell treatment; 2 weeks later, 94% of tumor burden was reduced. However, the tumor gradually grew back beginning at week 3, indicating the tumor recurrence from incomplete treatment. In contrast, the RPMI8226 MM tumors progressively grew in all of the untreated mice and mice treated with $1\times10^5$ CAR-T cells, until all the mice died of tumor in 81±2.7 days. These results demonstrate that anti-CD38 A2 CAR-T cells can effectively eradicate in vivo MM tumors with CD38 upregulation.

In conclusion, the foregoing results demonstrate that the Anti-CD38 A2 CAR-T cells exhibit an antibody-type specificity that can recognize CD38 high expression cells in a MHC-nonrestricted fashion, resulting in T-cell activation, target cell lysis in vitro and eradication of MM tumor in vivo.

To investigate possible fratricide activity of CAR2-AntiCD38 CAR-T cells, two assays were performed. In a first assay, monitored CD38 expression on CAR2-AntiCD38 CAR-T cells. By using K562 and RPMI8226 as CD38 negative and high expression controls respectively, and according to the CD38 expression levels, the activated T cells could be divided into three populations: CD38 negative, CD38 low and CD38 high expression population. In one of the donors, the T cell populations were 12%, 77%, and 11%, respectively in the control non-transduced T cells and were 17%, 82% and 1%, respectively in the CAR-T cells (FIG. 4). Similar results were obtained from other donors.

The disappearance of the CD38 high expression population from the CAR-T cells represents the fratricide activity and the retention of CD38 negative and low expression populations in the CAR-T cells implies that the CAR2-AntiCD38 CAR-T cells selectively lyse the CD38 high expression cells.

Figure 5A:
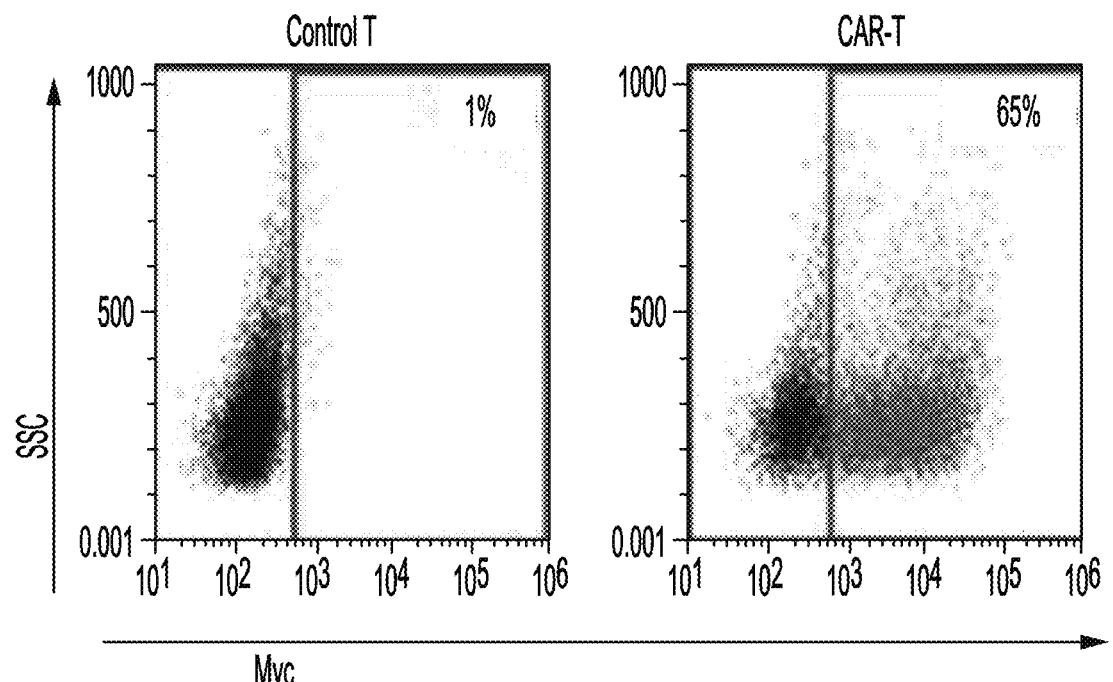
FIG. 5A shows stability of non-transduced control and Anti-CD38 A2 CAR transduced T cells after 15 days of culture, where the percentage of CAR-positive cells among the transduced T cells declined only slightly from 74% on day 4 (FIG. 5A) after transduction to 65% on day 15. The results indicate a reduction of fratricide by the Anti-CD38 A2 CAR transduced T cells. Non-transduced control and Anti-CD38 A2 CAR transduced T cells were analyzed on day 15 after transduction by flow cytometry for stability of CAR-T cells by staining with PE-conjugated anti-myc antibody.
Figure 5B:
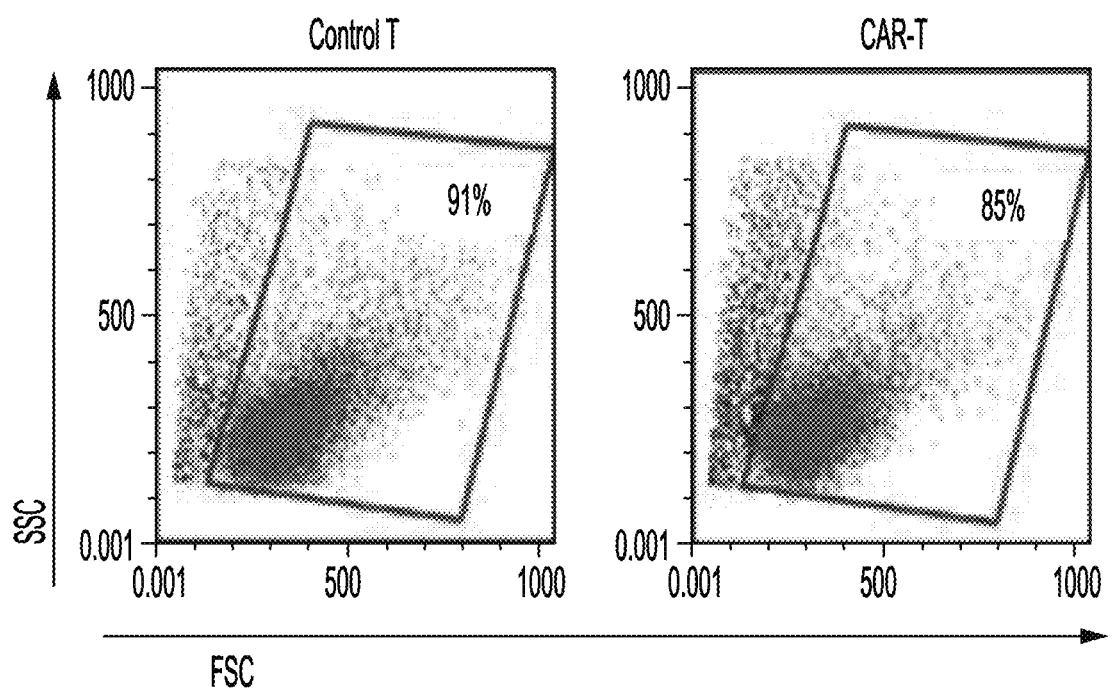
FIG. 5B shows that viability of the transduced T cells (85%) was comparable to the control T cells (91%). Similar results were obtained from other donors. The results indicate a reduction of fratricide by the Anti-CD38 A2 CAR transduced T cells. Non-transduced control and Anti-CD38 A2 CAR transduced T cells were analyzed on day 15 after transduction by flow cytometry for viability of T cells by gating viable cells with forward scatter (FSC) and side scatter (SSC).

In a second assay, stability and viability of the CAR-T cells in long-term cell culture was monitored (FIGS. 5A and B). After 15 days of culture, the percentage of CAR-positive cells among the transduced T cells declined only slightly from 74% on day 4 after transduction to 65% on day 15, and the viability was comparable to the control cells (85% versus 91%). Similar results were obtained from other donors. These results further confirm that the CAR2-AntiCD38 CAR-T cells exhibit limited fratricide activity and remain relatively stable and viable after long-term cell culture.

The second unique property of the CAR2-AntiCD38 CAR-T cells is that the CAR2-AntiCD38 CAR-T cells selectively lyse CD38 high expression cells and leave CD38 low expression cells intact. This characteristic allows the CAR-T cells to survive well in culture with limited fratricide activity and provide a clinical advantage for limited on-target off-tumor side effects pertaining to CAR-T cells, as the CAR2-AntiCD38 CAR-T cells will selectively kill CD38 high expression MM cells but not CD38 low expression normal cells.

Generation of an anti-CD38 CAR based on a mouse anti-CD38 mAb, THB-7 (Mihara et al., *J. Immunother.* 32(7): 737-743, 2009; Mihara et al., Br. *J. Haematol.* 151(1): 37-46; and 2010, Bhattacharyya et al., *Blood Cancer J.* 2(6): e75, 2012) showed that the anti-CD38 CAR-T cells could not survive on their own. This is presumably because of high fratricide activity caused by the association of the anti-CD38 CAR with intrinsic CD38 expressed on the activated T cell surface. Drent et al reported their anti-CD38 CAR-T study based on human anti-CD38 antibodies in which only CD38 negative anti-CD38 CAR-T cells survived in the culture (Drent et al., *Haematologica* 101(5): 616-625, 2016). However, the present foregoing data showed that the disclosed CAR2-AntiCD38 CAR-T cells (based on the A2 and D8 antibodies) only lysed a fraction of CD38 high expression T cells and left the majority T cells which were either CD38 low or negative intact, resulting in very limited fratricide activity and the viability of the transduced T cells remained high in long-term cell culture. Without being bound by theory this preference may be due to the relatively low affinity of the human antibody A2 that was used. Without being bound by theory, a low-affinity human anti-CD38 antibody is effective for the CAR-T cells to exhibit efficient and robust target cell lysis activity in vitro and to eradicate CD38 high expression MM tumors in vivo. Unlike the other anti-CD38 CAR-T cells tested in MM, which were CD38-negative and only temporarily suppressed tumor growth (Drent et al. supra), the foregoing CAR2-AntiCD38 CAR-T cells eradicated the CD38-expressing tumor cells without relapse in animal model. The ability of the foregoing CAR2-AntiCD38 CAR-T cells to discriminate between low and high CD38 expression cells, i.e., to selectively kill the CD38 high expressing tumor cells but not the CD38 low expressing normal cells, provides an important clinical advantage.

EXAMPLES

The following examples are meant to be illustrative and can be used to further understand embodiments of the present disclosure and should not be construed as limiting the scope of the present teachings in any way.

Example 1: Cell Lines, Antibodies and CD38-Fc Fusion Protein

Human plasmacytoma/multiple myeloma cell line RPMI8226 (Dalton et al., 1986 Cancer Research 46:5125-5130), which expresses CD38 at relatively high level (Genty et al., *Leuk Res* 28(3): 307-313 2004) and human chronic myelogenous leukemia cell line K562, which is CD38 negative (Gregorini, Tomasetti et al., 2006 Cell Biology International 30(9):727-732), were purchased from American Type Culture Collection (Rockville, Md.). RPMI8226 cells expressing luciferase and green fluorescent protein fusion protein (Luc-GFP) were created by retroviral-mediated transduction with a Luc-GFP expressing retroviral vector created by us. All cells were grown in RPMI1640 medium supplemented with 10% heat-inactivated fetal calf serum, 100 U/ml penicillin, 100 µg/ml streptomycin.

R-phycoerythrin (PE)-conjugated mouse anti-myc tag monoclonal antibody (mAb) was purchased from R & D Systems (Minneapolis, Minn.). FITC-conjugated goat anti-Myc tag polyclonal antibody was purchased from Abcam (Cambridge, Mass.). Mouse anti-human CD38 mAb was purchased from Biolegend (San Diego, Calif.). PE-conjugated goat anti-human IgG antibody was purchased from Southern Biotech (Birmingham, Ala.). APC-conjugated mouse anti-human CD3 was from BD Bioscience (San Diego, Calif.)

CD38-Fc fusion protein that consists of human CD38 extracellular domain of amino acid 19 to 238 and human IgG1 Fc region at the N-terminus was purchased from Creative BioMart (Shirley, N.Y.)

Example 2: Retroviral Mediated Transduction of T Cells with CAR2-AntiCD38 CAR Retroviral-mediated transduction of T cells with CAR was performed as described in Ma et al., 2004 *The Prostate* 61:12-25; and Ma et al., *The Prostate* 74(3):286-296, 2014 (the disclosure of which is incorporated by reference herein in their entireties). In brief, the retroviral vector DNA was transfected into Phoenix Ecotropic 293 cells using FuGene reagent (Promega, Madison, Wis.) and the transient viral supernatant was used to transduce PG13 packaging cells. Viral supernatant from PG13 cells was used to transduce activated T cells for stable expressing CAR2-AntiCD38 CAR. $5 \times 10^6$ activated human T cells were transduced in 10 µg/ml retronectin (Clontech, Mountain View, Calif.) pre-coated 6-well plate with 3 ml viral supernatant and were centrifuged at 1000 g for 1 hour at 32° C. The transduction procedure was repeated as needed. Activated human T cells were prepared by activating normal healthy donor peripheral blood mononuclear cells (PBMC) with 100 ng/ml mouse anti-human CD3 antibody OKT3 (Orth Biotech, Rartian, N.J.) and 300-1000 U/ml IL2 in AIM-V growth medium (GIBCO-Thermo Fisher scientific, Waltham, Mass.) supplemented with 5% FBS for two days. After transduction, the transduced T cells were expanded in AIM-V growth medium supplemented with 5% FBS and 300-1000 U/ml IL2.

Example 3: Western Blot

The membrane fractions of non-transduced and CAR2-AntiCD38 CAR transduced T cells were extracted using Membrane Extract kit (Thermo Fisher Scientific, Waltham, Mass.). Samples were denatured in sodium dodecyl sulfate (SDS) sample buffer with (reducing conditions) or without (non-reducing conditions) 10% 2-mercaptoethanol (β-ME) and resolved on 4-12% SDS-polyacrylamide gel electrophoresis gels, followed by electro-transferring onto a polyvinyl Dene difluoride (PVDF) membrane (Thermo Fisher Scientific, Waltham, Mass.). The membranes were blocked with 5% no-fat dry milk in Tris-buffered saline (20 mM Tris/500 mM NaCl, pH 7.5) for 1-2 hours. Membranes were washed with TBST (Tris-buffered saline containing 0.05% Tween-20), then incubated with anti-CD3ζ antibody (BD, San Jose, Calif.) at a dilution of 1:1000 for 1 hour, followed by the incubation with horseradish peroxidase (HRP)-conjugated goat anti-mouse IgG antibody (Jackson ImmunoResearch, West Grove, Pa.) at a dilution of 1:5000 for 1 hour, all in 5% non-fat dry milk in TBST. The membrane was developed with ECL chemiluminescent substrate (Thermo Fisher Scientific, Waltham, Mass.) and the chemiluminescent signal was detected by ChemiDoc Imaging Systems (Bio-Rad, Hercules, Calif.) (FIG. 2).

Example 4: Flow Cytometric Analysis

For detecting the expression of CD38 on cell surface, flow cytometric assays were performed. Cells were incubated with mouse anti-human CD38 mAb in 50 µl binding buffer (RPMI 1640 containing 10% horse serum) for 30 minutes with mixing. The cells were then washed with PBS and incubated under the same conditions with APC-conjugated goat anti-mouse IgG antibody. After wash with PBS, the samples were analyzed on an Attune NxT Flow Cytometer (Thermo Fisher Scientific, Waltham, Mass.). For detecting the CAR2-AntiCD38 CAR on the transduced T cells, cells were stained with PE-conjugated mouse anti-myc tag mAb for 30 minutes and analyzed by flow cytometer. For analysis of the antigen binding activity of CAR2-AntiCD38 CAR-T cells, $1\times10^6$ non-transduced control T cells or transduced CAR-T cells were incubated with CD38-Fc fusion protein followed by staining with PE-conjugated goat anti-human IgG antibody and FITC-conjugated goat anti-myc antibody, the samples were analyzed with flow cytometer.

Example 5: T Cell Activation Assays

Non-transduced control T cells and CAR2-AntiCD38 CAR-transduced T cells were stimulated in microtiter plates with K562 or RPMI8226 tumor cells. For cytokine production assay, $1\times10^5$ cells/well non-transduced control T cells or CAR2-AntiCD38 CAR-transduced T cells were mixed with $1\times10^5$ cells/well K562 or RPMI8226 in growth medium. After culturing for 24 hours, culture supernatants were harvested and measured for IL2 and IFNγ with ELISA assay kits from eBioscience (San Diego, Calif.). For CAR-T cells antigen-specific clonal expansion assay, K562 and RPMI8226 tumor cells were first treated with 50 uM of Mitomycin C (MMC, R&D, Minneapolis, Minn.) for 1.5 hours at 37° C. to arrest the cells from proliferation and then seeded in 48-well plate at $2.5\times10^5$ cells/well. $1\times10^6$ cells/well transduced CAR-T cells were added to the tumor cells and co-cultured at 37° C. for seven days with 300 U/ml IL2. Cells were harvested and stained with APC-conjugated anti-CD3 and FITC-conjugated anti-myc antibodies and analysed by flow cytometer for antigen-specific CAR-T cells clonal expansion. All experiments were done in triplicate.

Example 6: T Cell Cytotoxicity Assay

Cytotoxicity of CAR2-AntiCD38 CAR-T cells was measured by DELFIA cytotoxicity assay (PerkinElmer, Waltham, Mass.). K562 and RMPI8622 tumor cells were first loaded with fluorescence enhancing ligand for 25 minutes at 37° C. $2.5\times10^3$ cells/well K562 or $5\times10^3$ cells/well RPMI8226 tumor cells were then mixed with non-transduced control or transduced T cells at different effector:target(E:T) ratios and incubated for 2 hours. 20 µl/well supernatant were harvested and analyzed for the released ligand by adding europium solution to form fluorescent chelate. Time-Resolved Fluorescence (TRF) was measured on the TRF capable plate reader Cytation 5 (BioTek instruments, Winooski, Vt.). The cytotoxicity was calculated by using the following formula: % Specific Lysis=(Experimental−Spontaneous)/(Maximum−Spontaneous)*100.

Example 7: Treatment of MM Xenografts in NSG Mice

All animal experiments were performed in compliance with guideline for care and use of laboratory animal. Eight-week-old female NSG immunodeficient mice purchased from The Jackson Laboratory (Bar Harbor, Me.) were inoculated intravenously (i.v.) with $1\times10^7$ Luc-GFP labelled RPMI8226 cells via tail veil. Tumor burden was measured weekly by bioluminescent imaging using an IVIS Spectrum In Vivo Imaging System (PerkinElmer, Waltham, Mass.). After IVIS measurable systemic tumors formed on day 23, mice were injected i.v. with $1\times10^7$ non-transduced control T cells or transduced CAR-T cells. 1 µg of human IL15 was administrated daily via intraperitoneal injection from the day before T cell injection for 5 consecutive days to enhance the T cell engraftment. Tumor burden was measured weekly. Peripheral blood samples were taken by tail vein bleeding at 3 hours, day 1, day 2, then weekly after T cell injection and were pooled together by groups. T cell engraftment and expansion was measured by flow cytometric assays with APC-conjugated mouse anti-human CD3 and PE-conjugated mouse anti-myc antibodies. Blood levels of human cytokine IFNγ, IL2, and TNFα were measured by using Bio-Rad Luminex Assays (Bio-Rad, Hercules, Calif.). Animals were monitored for signs of disease progression and overt toxicity, such as GVHD, as evidenced by >15% loss in body weight, loss of fur, and moribund. The endpoint for the survival study was the day when the mice lost more than 15% of body weight or became moribund.

The disclosure includes the following embodiments.

Embodiment 1 is a host cell, or a population of host cells, which express an anti-CD38 chimeric antigen receptor (CAR) construct comprising: i) an antigen binding protein that binds to CD38, wherein the antigen binding protein is an scFv antibody comprising a heavy chain variable (VH) domain comprising the amino acid sequence of SEQ ID NO: 1 and a light chain variable (VL) domain comprising the amino acid sequence of SEQ ID NO: 3; ii) a transmembrane domain; and iii) an intracellular domain comprising an amino acid sequence that is at least 95% identical to the amino acid sequence of SEQ ID NO: 9 and an amino acid sequence that is at least 95% identical to the amino acid sequence of SEQ ID NO: 10, wherein the host cell or population of host cells are transduced with an expression vector operably linked to a nucleic acid encoding the anti-CD38 CAR construct, and wherein the expression vector directs expression of the anti-CD38 CAR construct in the host cell; wherein the host cell is a CD38-expressing T host cell or natural killer host cell or the population of host cells is a CD38-expressing population of T host cells or natural killer host cells.

Embodiment 2 is a host cell, or a population of host cells, which express an anti-CD38 chimeric antigen receptor (CAR) construct which comprises: i) an antigen binding protein that binds to CD38, wherein the antigen binding protein is an scFv antibody comprising a heavy chain variable (VH) domain comprising the CDRs set forth in the amino acid sequence of SEQ ID NO: 1 and a light chain variable (VL) domain comprising the CDRs set forth in the amino acid sequence of SEQ ID NO: 3; ii) a transmembrane domain; and iii) an intracellular domain, wherein the host cell or population of host cells are transduced with an expression vector operably linked to a nucleic acid encoding the anti-CD38 CAR construct, and wherein the expression vector directs expression of the anti-CD38 chimeric CAR construct in the host cell; wherein the host cell is a CD38-expressing T host cell or natural killer host cell or the population of host cells is a CD38-expressing population of T host cells or natural killer host cells.

Embodiment 3 is the host cell or population of host cells of embodiment 1 or 2, wherein the expression vector comprises a retroviral expression vector.

Embodiment 4 is the host cell or population of host cells of embodiment 1 or 2, wherein the natural killer host cell or the population of natural killer host cells is a placental derived natural killer host cell or a population thereof, or a cord blood derived natural killer host cell or a population thereof.

Embodiment 5 is the host cell or population of host cells of embodiment 1 or 2, wherein the anti-CD38 chimeric antigen receptor (CAR) construct further comprises a peptide linker between the heavy chain variable (VH) domain and the light chain variable (VL) domain, wherein the peptide linker comprises the amino acid sequence of SEQ ID NO: 5.

Embodiment 6 is the host cell or population of host cells of embodiment 1, wherein the antigen binding protein comprises the amino acid sequence of SEQ ID NO: 12.

Embodiment 7 is the host cell or population of host cells of embodiment 1 or 2, wherein the anti-CD38 chimeric antigen receptor (CAR) construct further comprises a hinge region between the antigen binding protein and the transmembrane domain, wherein the hinge region is a CD8 hinge region comprising the amino acid sequence of SEQ ID NO. 6.

Embodiment 8 is the host cell or population of host cells of embodiment 1, wherein the anti-CD38 chimeric antigen receptor (CAR) construct further comprises a CD28 extracellular domain between the antigen binding protein and the transmembrane domain, wherein the CD28 extracellular domain comprises the amino acid sequence of SEQ ID NO: 7.

Embodiment 9 is the host cell or population of host cells of embodiment 1 or 2, wherein the transmembrane domain is a CD28 transmembrane domain which comprises the amino acid sequence of SEQ ID NO: 8.

Embodiment 10 is the host cell or population of host cells of embodiment 1 or 2, wherein the intracellular domain comprises a CD28 intracellular domain which comprises the amino acid sequence of SEQ ID NO:9 and a CD3-zeta intracellular domain which comprises the amino acid sequence of SEQ ID NO:10.

Embodiment 11 is the host cell or population of host cells of embodiment 1, wherein the anti-CD38 chimeric antigen receptor (CAR) construct comprises an amino acid sequence that is at least 95% identical to the amino acid sequence of SEQ ID NO: 20.

Embodiment 12 is the host cell or population of host cells of embodiment 1 or 2, wherein the anti-CD38 chimeric antigen receptor (CAR) construct further comprises a hinge region between the antigen binding protein and the transmembrane domain, wherein the hinge region is chosen from a CD8 hinge region and a CD8α hinge region.

Embodiment 13 is the host cell or population of host cells of embodiment 1 or 2, wherein the anti-CD38 chimeric antigen receptor (CAR) construct further comprises a hinge region between the antigen binding protein and the transmembrane domain, wherein the hinge region is a CD8 hinge region comprising the amino acid sequence of SEQ ID NO. 17.

Embodiment 14 is the host cell or population of host cells of embodiment 1 or 2, wherein the transmembrane domain is a transmembrane domain of a protein chosen from alpha chain of T-cell receptor, beta chain of T-cell receptor, zeta chain of T-cell receptor, CD28, CD3 epsilon, CD45, CD4, CDS, CD8, CD9, CD16, CD22, CD33, CD37, CD64, CD80, CD86, CD134, CD137, CD154, LFA-1 T-cell co-receptor, CD2 T-cell co-receptor/adhesion molecule, and CD8 alpha.

Embodiment 15 is the host cell or population of host cells of embodiment 1 or 2, wherein the intracellular domain is an intracellular domain of a protein chosen from CD3-zeta, 4-1BB, and a CD28.

Embodiment 16 is the host cell or population of host cells of embodiment 1 or 2, wherein the intracellular domain comprises a co-stimulatory signaling domain of a protein chosen from CD27, CD28, 4-1BB, OX40, CD30, CD40, PD-1, ICOS, lymphocyte function-associated antigen-1 (LFA-1), CD2, CD7, LIGHT, NKG2C, B7-H3, and a CD83 ligand.

Embodiment 17 is the host cell or population of host cells of embodiment 1 or 2, wherein the anti-CD38 chimeric antigen receptor (CAR) construct further comprises a signal sequence, wherein the signal sequence is a signal sequence of a protein chosen from CD8a, CD28, and CD16.

Embodiment 18 is a method of treating a human subject having a disorder associated with detrimental CD38 expression, comprising administering to the subject the host cell or population of host cells of embodiment 1 or 2.

Embodiment 19 is the method of embodiment 18, wherein the disorder is a cancer chosen from hematologic, breast cancer, ovarian cancer, prostate cancer, head and neck cancer, lung cancer, bladder cancer, melanoma, colorectal cancer, pancreatic cancer, lung cancer, liver cancer, renal cancer, esophageal cancer, leiomyoma, leiomyosarcoma, glioma, and glioblastoma.

Embodiment 20 is the method of embodiment 18, wherein the disorder is a hematologic cancer chosen from non-Hodgkin's lymphoma (NHL), Burkitt's lymphoma (BL), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), chronic myeloid leukemia (CML), and multiple myeloma (MM).

Embodiment 21 is the method of embodiment 18, wherein the host cell or population of host cells is autologous to the subject.

Embodiment 21 is the method of embodiment 18, wherein the host cell or population of host cells is not autologous to the subject.

TABLE 1

| SEQ ID NO: | SEQUENCE | DESCRIPTION |
|---|---|---|
| 1 | QVQLVESGGGLVKPGGSLRLSCAASGFTFSDDYMSWIRQAPGKGLEWVASVSNGRPTTYYADSVRGRFTISRDNAKNSLYLQMNSLRAEDTAVYYCAREDWGGEFTDWGRGTLVTVSS | C38A2 variable heavy chain-amino acid |
| 2 | QVQLVESGGGVVQPGGSLRLSCAASGFIVSTNYVHWVRQAPGKGLEWVSGIYSDPYTSYAYSDSVKGRFTISRDMSKNTVYLQMNRLRAEDTAVYYCARETNTGFSNSWYLDFWGQGTLVTVSS | C38D8 variable heavy chain-amino acid |
| 3 | QAGLTQPPSASGTSGQRVTISCSGSSSNIGINFVYWYQHLPGTAPKLLIYKNNQRPSGVPDRFSGSKSGNSASLAISGLRSEDEADYYCAAWDDSLSGYVFGSGTKVTVL | C38A2 variable light chain-amino acid |
| 4 | QPVLTQPPSASGTPGQRVTISCSGSSSNIGRNIVNWYQQLPGTTPKLLIYSNNQRPSGVPDRFSGSKSGTSASLAISGLHSEDEADYYCATWDDSLNGWVFGGGTKLTVL | C38D8 variable light chain-amino acid |
| 5 | GGGGSGGGGSGGGGS | peptide linker connecting VH and VL-amino acid |
| 6 | AKPTTTPAPRPPTPAPTIASQPLSLRPEACRPAAGGAVHTRGLDFA | CD8 hinge region-amino acid |
| 7 | KIEVMYPPPYLDNEKSNGTIIHVKGKHLCPSPLFPGPSKP | CD28 extra-cellular domain/spacer-amino acid |
| 8 | FWVLVVVGGVLACYSLLVTVAFIIFWV | CD28 trans-membrane domain-amino acid |
| 9 | RSKRSRLLHSDYMNMTPRRPGPTRKHYQPYAPPRDFAAYRS | CD28 intra-cellular signaling domain-amino acid |
| 10 | RVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPR | CD3-ζ signaling domain-amino acid |
| 11 | EQKLISEEDL | Myc tag |
| 12 | QVQLVESGGGLVKPGGSLRLSCAASGFTFSDDYMSWIRQAPGKGLEWVASVSNGRPTTYYADSVRGRFTISRDNAKNSLYLQMNSLRAEDTAVYYCAREDWGGEFTDWGRGTLVTVSSGGGGSGGGGSGGGGSQAGLTQPPSASGTSGQRVTISCSGSSSNIGINFVYWYQHLPGTAPKLLIYKNNQRPSGVPDRFSGSKSGNSASLAISGLRSEDEADYYCAAWDDSLSGYVFGSGTKVTVL | C38A2 scFv |
| 13 | FS1 5'-ACACAGTCCTGCTGACCA-3' | Sequencing Primer |
| 14 | FS5 5'-GGGAGTCATGTTCATGTAG-3' | Sequencing Primer |
| 15 | BS2 5'-TGGTGATATTGTTGAGT-3' | Sequencing Primer |
| 16 | QVQLVESGGGVVQPGGSLRLSCAASGFIVSTNYVHWVRQAPGKGLEWVSGIYSDPYTSYAYSDSVKGRFTISRDMSKNTVYLQMNRLRAEDTAVYYCARETNTGFSNSWYLDFWGQGTLVTVSSGGGGSGGGGSGGGGSQPVLTQPPSASGTPGQRVTISCSGSSSNIGRNIVNWYQQLPGTTPKLLIYSNNQRPSGVPDRFSGSKSGTSASLAISGLHSEDEADYYCATWDDSLNGWVFGGGTKLTVL | CD38D8 scFv |
| 17 | AKPTTTPAPRPPTPAPTIASQPLSLRPEACRPAAGGAVHTRGLDFAPRKIEVMYPPPYLDNEKSNGTIIHVKGKHLCPSPLFPGPSKP | Hinge sequence-amino acid |
| 18 | KIEVMYPPPYLDNEKSNGTIIHVKGKHLCPSPLFPGPSKPFWVLVVVGGVLACYSLLVTVAFIIFWVRSKRSRLLHSDYMNMTPRRPGPTRKHYQPYAPPRDFAAYRS | CD28 full length-amino acid |
| 19 | MEWSWVFLFFLSVTTGVHS | Signal peptide from mouse antibody heavy chain |
| 20 | MEWSWVFLFFLSVTTGVHSDIEQKLISEEDLQVQLVESGGGLVKPGGSLRLSCAASGFTFSDDYMSWIRQAPGKGLEWVASVSNGRPTTYYADSVRGRFTISRDNAKNSLYLQMNSLRAEDTAVYYCAREDWGGEFTDWGRGTLVTVSSGGGGSGGGGSGGGGSQAGLTQPPSASGTSGQRVTISCSGSSSNIGINFVYWYQHLPGTAPKLLIYKNNQRPSGVPDRFSGSKSGNSASLAISGLRSEDEADYYCAAWDDSLSGYVFGSGTKVTVLAKPTTTPAPRPPTPAPTIASQPLSLRPEACRPAAGGAVHTRGLDFAKIEVMYPPPYLDNEKSNGTIIHVKGKHLCPSPLFPGPSKPFWVLVVVGGVLACYSLLVTVAFIIFWVRSKRSRLLHSDYMNMTPRRPGPTRKHYQPYAPPRDFAAYRSRVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPR | CD38A2 CAR-amino acid |
| 21 | MEWSWVFLFFLSVTTGVHSDIEQKLISEEDLQVQLVESGGGVVQPGGSLRLSCAASGFIVSTNYVHWVRQAPGKGLEWVSGIYSDPYTSYAYSDSVKGRFTISRDMSKNTVYLQMNRLRAEDTAVYYCARETNTGFSNSWYLDFWGQGTLVTVSSGGGGSGGGGSGGGGSQPVLTQPPSASGTPGQRVTISCSGSSSNIGRNIVNWYQQLPGTTPKLLIYSNNQRPSGVPDRFSGSKSGTSASLAISGLHSEDEADYYCATWDDSLNGWVFGGGTKLTVLAKPTTTPAPRPPTPAPTIASQPLSLRPEACRPAAGGAVHTRGLDFAKIEVMYPPPYLDNEKSNGTIIHVKGKHLCPSPLFPGPSKPFWVLVVVGGVLACYSLLVTVAFIIFWVRSKRSRLLHSDYMNMTPRRPGPTRKHYQPYAPPRDFAAYRSRVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPR | CD38D8 CAR-amino acid |
| 22 | GAGCAGAAGCTTATCTCCGAGGAAGATCTG | DNA sequence encoding human cmyc tag |

We claim:

1. A host cell, or a population of host cells, which express an anti-CD38 chimeric antigen receptor (CAR) construct comprising:
   i) an antigen binding protein that binds to CD38, wherein the antigen binding protein is an scFv antibody comprising a heavy chain variable (VH) domain comprising the amino acid sequence of SEQ ID NO: 1 and a light chain variable (VL) domain comprising the amino acid sequence of SEQ ID NO: 3;
   ii) a transmembrane domain; and
   iii) an intracellular domain comprising an amino acid sequence that is at least 95% identical to the amino acid sequence of SEQ ID NO: 9 and an amino acid sequence that is at least 95% identical to the amino acid sequence of SEQ ID NO: 10,
      wherein the host cell or population of host cells are transduced with an expression vector operably linked to a nucleic acid encoding the anti-CD38 CAR construct, and
      wherein the expression vector directs expression of the anti-CD38 CAR construct in the host cell;
   wherein the host cell is a wild-type-CD38-expressing T host cell or a wild-type-CD38-expressing natural killer host cell or the population of host cells is a wild-type-CD38-expressing population of T host cells or a wild-type-CD38-expressing population of natural killer host cells.

2. A host cell, or a population of host cells, which express an anti-CD38 chimeric antigen receptor (CAR) construct which comprises:
   i) an antigen binding protein that binds to CD38, wherein the antigen binding protein is an scFv antibody comprising a heavy chain variable (VH) domain comprising the CDRs set forth in the amino acid sequence of SEQ ID NO: 1 and a light chain variable (VL) domain comprising the CDRs set forth in the amino acid sequence of SEQ ID NO: 3;
   ii) a transmembrane domain; and
   iii) an intracellular domain,
      wherein the host cell or population of host cells are transduced with an expression vector operably linked to a nucleic acid encoding the anti-CD38 CAR construct, and
      wherein the expression vector directs expression of the anti-CD38 chimeric CAR construct in the host cell;
   wherein the host cell is a wild-type-CD38-expressing T host cell or a wild-type-CD38-expressing natural killer host cell or the population of host cells is a wild-type-CD38-expressing population of T host cells or a wild-type-CD38-expressing population of natural killer host cells.

3. The host cell or population of host cells of claim 1 or 2, wherein the expression vector comprises a retroviral expression vector.

4. The host cell or population of host cells of claim 1 or 2, wherein the natural killer host cell or the population of natural killer host cells is a placental derived natural killer host cell or a population thereof, or a cord blood derived natural killer host cell or a population thereof.

5. The host cell or population of host cells of claim 1 or 2, wherein the anti-CD38 chimeric antigen receptor (CAR) construct further comprises a peptide linker between the heavy chain variable (VH) domain and the light chain variable (VL) domain, wherein the peptide linker comprises the amino acid sequence of SEQ ID NO: 5.

6. The host cell or population of host cells of claim 1, wherein the antigen binding protein comprises the amino acid sequence of SEQ ID NO: 12.

7. The host cell or population of host cells of claim 1 or 2, wherein the anti-CD38 chimeric antigen receptor (CAR) construct further comprises a hinge region between the antigen binding protein and the transmembrane domain, wherein the hinge region is a CD8 hinge region comprising the amino acid sequence of SEQ ID NO. 6.

8. The host cell or population of host cells of claim 1, wherein the anti-CD38 chimeric antigen receptor (CAR) construct further comprises a CD28 extracellular domain between the antigen binding protein and the transmembrane domain, wherein the CD28 extracellular domain comprises the amino acid sequence of SEQ ID NO: 7.

9. The host cell or population of host cells of claim 1 or 2, wherein the transmembrane domain is a CD28 transmembrane domain which comprises the amino acid sequence of SEQ ID NO: 8.

10. The host cell or population of host cells of claim 1 or 2, wherein the intracellular domain comprises a CD28 intracellular domain which comprises the amino acid sequence of SEQ ID NO:9 and a CD3-zeta intracellular domain which comprises the amino acid sequence of SEQ ID NO:10.

11. The host cell or population of host cells of claim 1, wherein the anti-CD38 chimeric antigen receptor (CAR) construct comprises an amino acid sequence that is at least 95% identical to the amino acid sequence of SEQ ID NO: 20.

12. The host cell or population of host cells of claim 1 or 2, wherein the anti-CD38 chimeric antigen receptor (CAR) construct further comprises a hinge region between the antigen binding protein and the transmembrane domain, wherein the hinge region is chosen from a CD8 hinge region and a CD8a hinge region.

13. The host cell or population of host cells of claim 1 or 2, wherein the anti-CD38 chimeric antigen receptor (CAR) construct further comprises a hinge region between the antigen binding protein and the transmembrane domain, wherein the hinge region is a CD8 hinge region comprising the amino acid sequence of SEQ ID NO. 17.

14. The host cell or population of host cells of claim 1 or 2, wherein the transmembrane domain is a transmembrane domain of a protein chosen from alpha chain of T-cell receptor, beta chain of T-cell receptor, zeta chain of T-cell receptor, CD28, CD3 epsilon, CD45, CD4, CD5, CD8, CD9, CD16, CD22, CD33, CD37, CD64, CD80, CD86, CD134, CD137, CD154, LFA-1 T-cell co-receptor, CD2 T-cell co-receptor/adhesion molecule, and CD8 alpha.

15. The host cell or population of host cells of claim 2, wherein the intracellular domain is an intracellular domain of a protein chosen from CD3-zeta, 4-1BB, and a CD28.

16. The host cell or population of host cells of claim 1 or 2, wherein the intracellular domain comprises a co-stimulatory signaling domain of a protein chosen from CD27, CD28, 4-1BB, OX40, CD30, CD40, PD-1, ICOS, lymphocyte function-associated antigen-1 (LFA-1), CD2, CD7, LIGHT, NKG2C, and B7-H3.

17. The host cell or population of host cells of claim 1 or 2, wherein the anti-CD38 chimeric antigen receptor (CAR) construct further comprises a signal sequence, wherein the signal sequence is a signal sequence of a protein chosen from CD8a, CD28, and CD16.

18. The host cell or population of host cells of claim 1 or 2, wherein the host cell or population of host cells exhibits limited fratricide activity.

* * * * *